(12) United States Patent
Nakamura

(10) Patent No.: US 11,771,161 B2
(45) Date of Patent: Oct. 3, 2023

(54) HEADGEAR

(71) Applicant: TAIKI CORP., LTD., Osaka (JP)

(72) Inventor: Koji Nakamura, Osaka-shi (JP)

(73) Assignee: TAIKI CORP., LTD., Osaka (JP)

( * ) Notice: Subject to any disclaimer, the term of this patent is extended or adjusted under 35 U.S.C. 154(b) by 67 days.

(21) Appl. No.: 17/624,646

(22) PCT Filed: Jul. 30, 2020

(86) PCT No.: PCT/JP2020/029285
§ 371 (c)(1),
(2) Date: Jan. 4, 2022

(87) PCT Pub. No.: WO2021/024913
PCT Pub. Date: Feb. 11, 2021

(65) Prior Publication Data
US 2022/0256957 A1    Aug. 18, 2022

(30) Foreign Application Priority Data

Aug. 2, 2019   (JP) ................................ 2019-143226
Dec. 3, 2019   (JP) ................................ 2019-218917
Dec. 27, 2019  (JP) ................................ 2019-238393

(51) Int. Cl.
*A42B 1/00*       (2021.01)
*A42B 1/008*      (2021.01)
(Continued)

(52) U.S. Cl.
CPC ............ *A42B 1/008* (2013.01); *A42B 1/0187* (2021.01); *A42B 1/04* (2013.01); *A42B 1/18* (2013.01); *A61F 7/10* (2013.01)

(58) Field of Classification Search
CPC ......... A42B 1/008; A42B 1/0187; A42B 1/04; A42B 1/18; A61F 7/10
See application file for complete search history.

(56) References Cited

U.S. PATENT DOCUMENTS 3,469,264 A * 9/1969 Harris ...................... A42B 1/06
                                                    2/172
4,180,868 A * 1/1980 Snow ..................... A42B 3/105
                                                    2/205

(Continued)

FOREIGN PATENT DOCUMENTS

JP          6-12434 U       2/1994
JP         11-131316 A      5/1999
(Continued)

OTHER PUBLICATIONS

International Search Report dated Oct. 20, 2020, issued in counterpart International Application No. PCT/JP2020/029285 (3 pages).

*Primary Examiner* — Khaled Annis
(74) *Attorney, Agent, or Firm* — WHDA, LLP

(57) ABSTRACT

Provided is a headgear including first and second holding parts that respectively hold first and second cooling members. In a worn state, the first and second holding parts are respectively positioned laterally to left and right carotid arteries. The headgear includes a headgear main body to be worn on a head and a neck cover that covers a neck, the first and second holding parts are provided in the neck cover, the first holding part is a first pocket that stores the first cooling member, the second holding part is a second pocket that stores the second cooling member, and the headgear includes a coupling part that detachably couples a left end part and a right end part of the neck cover.

18 Claims, 69 Drawing Sheets

(51) Int. Cl.
*A42B 1/0187* (2021.01)
*A42B 1/04* (2021.01)
*A42B 1/18* (2006.01)
*A61F 7/10* (2006.01)

(56) References Cited

U.S. PATENT DOCUMENTS

| | | | | |
|---|---|---|---|---|
| 5,005,374 A | * | 4/1991 | Spitler | F25D 3/08 383/110 |
| 5,153,943 A | * | 10/1992 | Clement | A42B 1/0187 2/418 |
| 5,355,535 A | * | 10/1994 | Bruder | A42B 1/0187 2/172 |
| 5,448,778 A | * | 9/1995 | Phillips | A42B 1/0187 2/172 |
| 5,557,807 A | * | 9/1996 | Hujar | A42B 1/0187 2/209.13 |
| 5,603,120 A | * | 2/1997 | Gifford | A42B 3/105 2/172 |
| 5,655,225 A | * | 8/1997 | Mathers | A42B 1/0187 2/172 |
| 5,669,074 A | * | 9/1997 | Newman, Jr. | A42B 1/0187 2/172 |
| 5,669,075 A | * | 9/1997 | Weeks | A42C 5/04 2/200.1 |
| 5,790,986 A | * | 8/1998 | Hall | A42B 1/06 2/172 |
| 5,840,080 A | * | 11/1998 | Der Ovanesian | A61F 7/02 62/530 |
| 5,875,493 A | * | 3/1999 | MacDonald | A42B 1/205 2/171.1 |
| 5,887,287 A | * | 3/1999 | Potochnik | A42B 1/241 2/172 |
| 6,131,201 A | * | 10/2000 | Chu | A42B 1/0187 2/172 |
| 6,233,745 B1 | * | 5/2001 | Friesen | A42B 1/008 2/172 |
| 6,481,021 B2 | * | 11/2002 | Spell | A42B 1/0186 2/172 |
| 6,857,134 B1 | * | 2/2005 | Cowell | A42C 5/04 2/209.13 |
| 7,310,829 B1 | * | 12/2007 | Engel-Wilson | A42B 1/0187 2/209.13 |
| 8,108,944 B1 | * | 2/2012 | Gilson, Sr. | A42B 1/24 2/209.3 |
| 9,743,699 B2 | * | 8/2017 | Peterson | A42B 1/0187 |
| 10,609,977 B1 | * | 4/2020 | Stir | A42B 1/206 |
| 2002/0035745 A1 | * | 3/2002 | Spell | A61F 7/103 2/209.13 |
| 2003/0074717 A1 | * | 4/2003 | Robinson | A42B 7/00 2/204 |
| 2004/0078877 A1 | * | 4/2004 | Harty | A41D 13/0512 2/468 |
| 2004/0244095 A1 | * | 12/2004 | Sonne | A42B 1/0187 2/175.4 |
| 2005/0034215 A1 | * | 2/2005 | Harrison | A42C 5/04 2/207 |
| 2006/0212995 A1 | * | 9/2006 | Collins | A42B 1/0186 2/175.6 |
| 2006/0253954 A1 | * | 11/2006 | Music | A41D 13/0051 2/115 |
| 2008/0066214 A1 | * | 3/2008 | O'Hare | A42B 1/241 2/243.1 |
| 2008/0066216 A1 | * | 3/2008 | Yun | A42B 1/0187 2/172 |
| 2008/0216211 A1 | * | 9/2008 | Dolby | A42B 1/06 2/209 |
| 2009/0205107 A1 | * | 8/2009 | Coba | A42B 1/008 2/172 |
| 2011/0162131 A1 | * | 7/2011 | Harty | A42B 3/0473 2/413 |
| 2014/0013485 A1 | * | 1/2014 | Parker | A42B 1/0187 2/172 |
| 2014/0298567 A1 | * | 10/2014 | Potts | A42B 1/008 2/171.2 |
| 2015/0059054 A1 | * | 3/2015 | Peterson | A42B 1/0187 2/172 |
| 2016/0128411 A1 | * | 5/2016 | Ayres | A42B 1/008 2/172 |
| 2018/0271195 A1 | * | 9/2018 | Noa | A42B 1/0187 |
| 2019/0090556 A1 | * | 3/2019 | Ayres | A42B 1/241 |
| 2022/0256957 A1 | * | 8/2022 | Nakamura | A42B 1/04 |

FOREIGN PATENT DOCUMENTS

| | | |
|---|---|---|
| JP | 3071066 U | 8/2000 |
| JP | 2001-146621 A | 5/2001 |
| JP | 2006-97209 A | 4/2006 |
| JP | 2012-36533 A | 2/2012 |
| JP | 3190468 U | 5/2014 |
| JP | 3209489 U | 3/2017 |

* cited by examiner

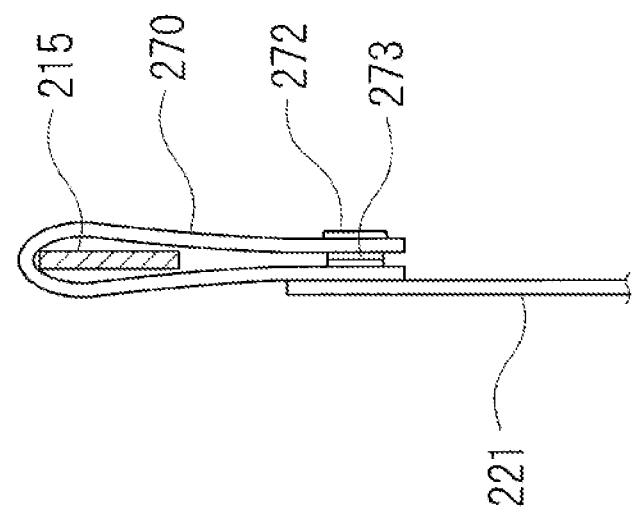
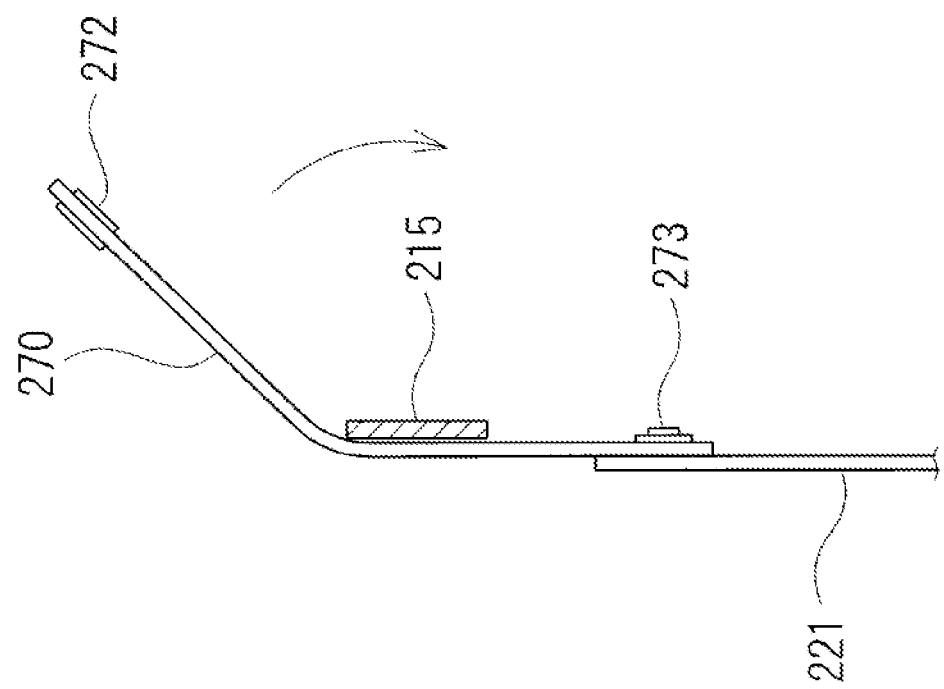
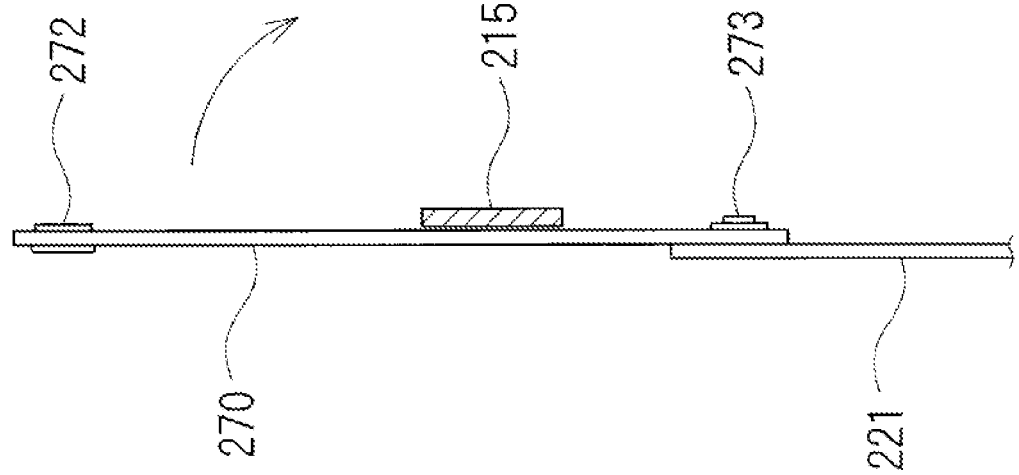

HEADGEAR

TECHNICAL FIELD

The present invention relates to a headgear, and in particular, relates to a headgear effective in preventing heatstroke.

BACKGROUND ART

PTL 1 and 2 mentioned below describe headgears capable of cooling the back of a head. However, these headgears are insufficient for preventing heatstroke.

CITATION LIST

Patent Literature

PTL 1: Japanese Utility Model Application Publication No. H6-12434

PTL 2: Japanese Unexamined Patent Application Publication No. 2001-146621

SUMMARY OF INVENTION

Technical Problem

An object of the present invention is to provide a headgear effective in preventing heatstroke.

Solution to Problem

A headgear according to the present invention includes first and second holding parts. The first and second holding parts can respectively hold first and second cooling members. When the headgear is worn, the first and second holding parts are respectively positioned laterally to the left and right carotid arteries.

According to this configuration, when the headgear is worn, the first cooling member held by the first holding part is positioned laterally to the left carotid artery and the second cooling member held by the second holding part is positioned laterally to the right carotid artery. The left and right carotid arteries are blood vessels leading from the heart to the brain. The left and right carotid arteries are effectively cooled by the first and second cooling members. Furthermore, the first and second cooling members are provided on the left and right side in a distributed manner, and thus, it is possible to prevent excessive weight increase, and the burden on the wearer is reduced.

The headgear preferably includes a headgear main body to be worn on a head and a neck cover that covers a neck. The first and second holding parts are provided in the neck cover. According to this configuration, the neck cover blocks sunlight shining on the neck. The first and second cooling members can be respectively held by the first and second holding parts provided in the neck cover.

The first holding part is preferably a first pocket that stores the first cooling member. The second holding part is a second pocket that stores the second cooling member. According to this configuration, a user can easily set the first and second cooling members such that the first and second cooling members are held by the first and second pockets.

The headgear is preferably provided with a coupling part that detachably couples a left end part and a right end part of the neck cover. According to this configuration, the user can couple the left and right end parts of the neck cover to each other by the coupling part. When the left and right end parts of the neck cover are coupled to each other, the neck cover covers the entire circumference of the neck, and thus, sunlight shining on the neck is surely blocked. Furthermore, positions of the first and second cooling members are stable. For example, even if the user tilts his/her head to the left or right, the first and second cooling members are not likely to laterally move away from the carotid arteries. Therefore, the left and right carotid arteries can be stably cooled by the first and second cooling members.

It is noted that the neck cover may be integrally formed with the headgear main body or may be formed separately from the headgear main body. Furthermore, the neck cover may have a cylindrical shape. For example, the left and right end parts of the neck cover may be sewn and connected to each other. A hole for exposing a face may be formed in a front surface of the neck cover having the cylindrical shape.

Preferably, the neck cover includes a left extension part and a right extension part. The left extension part is provided in the lower part of the left end part of the neck cover. The left extension part extends more to the front than an upper end part of the left end part of the neck cover. The right extension part is provided in the lower part of the right end part of the neck cover. The right extension part extends more to the front than an upper end part of the right end part of the neck cover. The coupling part is capable of detachably coupling the left extension part and the right extension part. A front side edge part of the first pocket is positioned near a region vertically below the upper end part of the left end part of the neck cover. A front side edge part of the second pocket is positioned near a region vertically below the upper end part of the right end part of the neck cover. It is noted that the front side edge part of the first pocket is a side edge part of the two side edge parts of the first pocket that is closer to the left extension part. The front side edge part of the second pocket is a side edge part of the two side edge parts of the second pocket that is closer to the right extension part. According to this configuration, when the left extension part and the right extension part are coupled by the coupling part, the upper end parts of the left and right end parts of the neck cover serve as fixed fulcrums. On the other hand, when the first and second cooling members are stored in the first and second pockets, the positions of the first and second pockets are stabilized by the weight of the first and second cooling members. Therefore, when the left extension part and the right extension part are coupled, the front side edge parts of the first and second pockets serve as pseudo fulcrums. When the front side edge parts of the first and second pockets are positioned near a region vertically below the upper end parts of the left and right end parts of the neck cover, a user can easily grasp and operate the left extension part and the right extension part. The user can easily couple the left extension part and the right extension part.

The headgear main body is preferably a hemispherical inner cap. A rear part of the headgear main body is connected to the neck cover. A front part and left and right side parts of the headgear main body are spaced from the neck cover. According to this configuration, the user can wear the headgear main body on the head and wear, for example, a head protection equipment such as a helmet over the headgear main body. The head protection equipment protects the head and the first and second cooling members cool the left and right carotid arteries. Therefore, the headgear is useful at a construction site, for example. Furthermore, portions of the headgear main body, except for the rear part, are spaced from the neck cover. Therefore, the headgear main body can easily move up, down, left, and right with respect to the neck cover. A user wearing the headgear main body can easily move the head. Even if the user moves the head, the neck cover is not easily displaced from the neck. Therefore, the first and second cooling members are always positioned laterally to the left and right carotid arteries.

The neck cover preferably includes a connection part connected to the rear part of the headgear main body. A length of the connection part in the left-right direction is shorter than a diameter of the headgear main body. According to this configuration, the headgear main body can be easily moved with respect to the neck cover.

The headgear main body preferably includes a major main body part that is a main portion of the headgear main body. The major main body part is made of a first fabric. The neck cover includes a main neck part that is a main portion of the neck cover. The main neck part is made of a second fabric that is thinner than the first fabric. According to this configuration, the headgear main body and the neck cover are formed as separate bodies, and thus, the headgear main body and the neck cover can each be easily manufactured. Furthermore, the second fabric is thinner than the first fabric, and thus, an excellent wearing feeling is obtained when the neck cover is wrapped around the neck.

The second fabric preferably has higher elasticity than the first fabric. According to this configuration, the user can easily wrap the neck cover around the neck. Close contact between the neck cover and the neck can easily be achieved.

The first fabric preferably has higher air permeability than the second fabric. According to this configuration, stuffy feeling of the head can be prevented.

The neck cover is preferably formed separately from the headgear main body. The neck cover includes a protruding part that protrudes upward. First and second attachment parts that detachably attach the neck cover to the headgear main body are provided in an upper end part of the protruding part. The first attachment part is provided above the first holding part, and the second attachment part is provided above the second holding part. According to this configuration, the neck cover is attached to the headgear main body by the first and second attachment parts. When the neck cover is attached to the headgear main body, the neck cover is stabilized. Therefore, when the neck cover is wrapped around the neck, an excellent wearing feeling is obtained. Furthermore, the neck cover includes the protruding part, and thus, the wearing feeling of the neck cover is improved. The first and second attachment parts are provided in the upper end part of the protruding part, and thus, the protruding part can be stably attached to the headgear main body. Therefore, a displacement of the neck cover is prevented, and thus, the wearing feeling is improved and the first and second cooling members are not easily displaced from the left and right carotid arteries. The first and second attachment parts are respectively positioned above the first and second cooling members, and thus, the stability of the first and second cooling members is increased.

Advantageous Effects of Invention

As described above, the left and right carotid arteries are cooled by first and second cooling members, and thus, heatstroke is effectively prevented.

BRIEF DESCRIPTION OF DRAWINGS

FIGS. 67(a) to 67(c) are enlarged views of main parts illustrating a process of attaching the neck cover to the headgear main body.

DESCRIPTION OF EMBODIMENTS

First Embodiment

Below, a headgear according to a first embodiment of the present invention will be described with reference to FIGS. 1 to 15. The headgear includes a headgear main body 1 to be worn on a head of a user and a neck cover 2 to be attached to a neck 610 of the user.

<Headgear Main Body 1>

Figure 1:
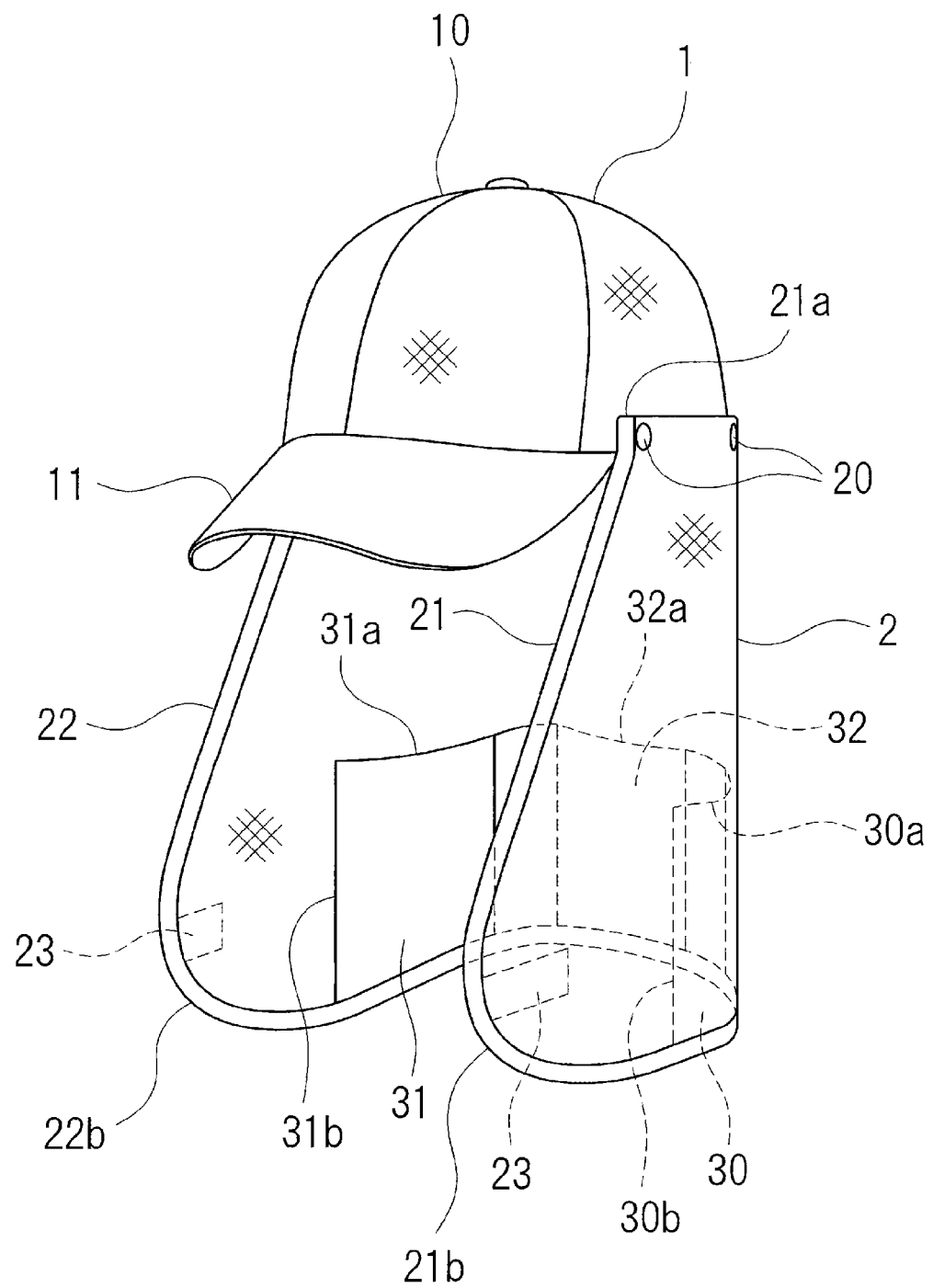
FIG. 1 is a perspective view of a headgear according to a first embodiment of the present invention.
Figure 2:
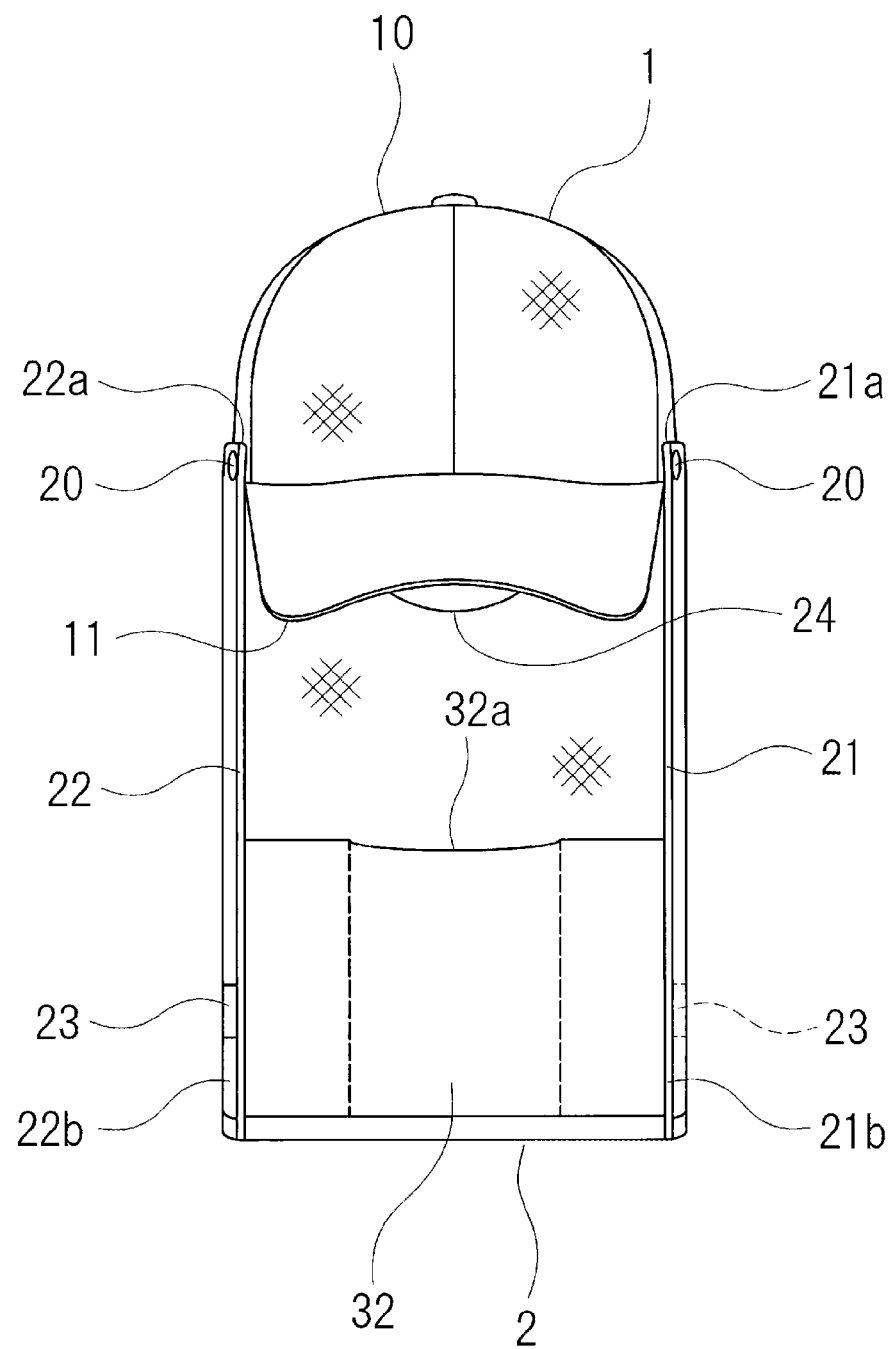
FIG. 2 is a front view of the headgear seen from a front side.
Figure 3:
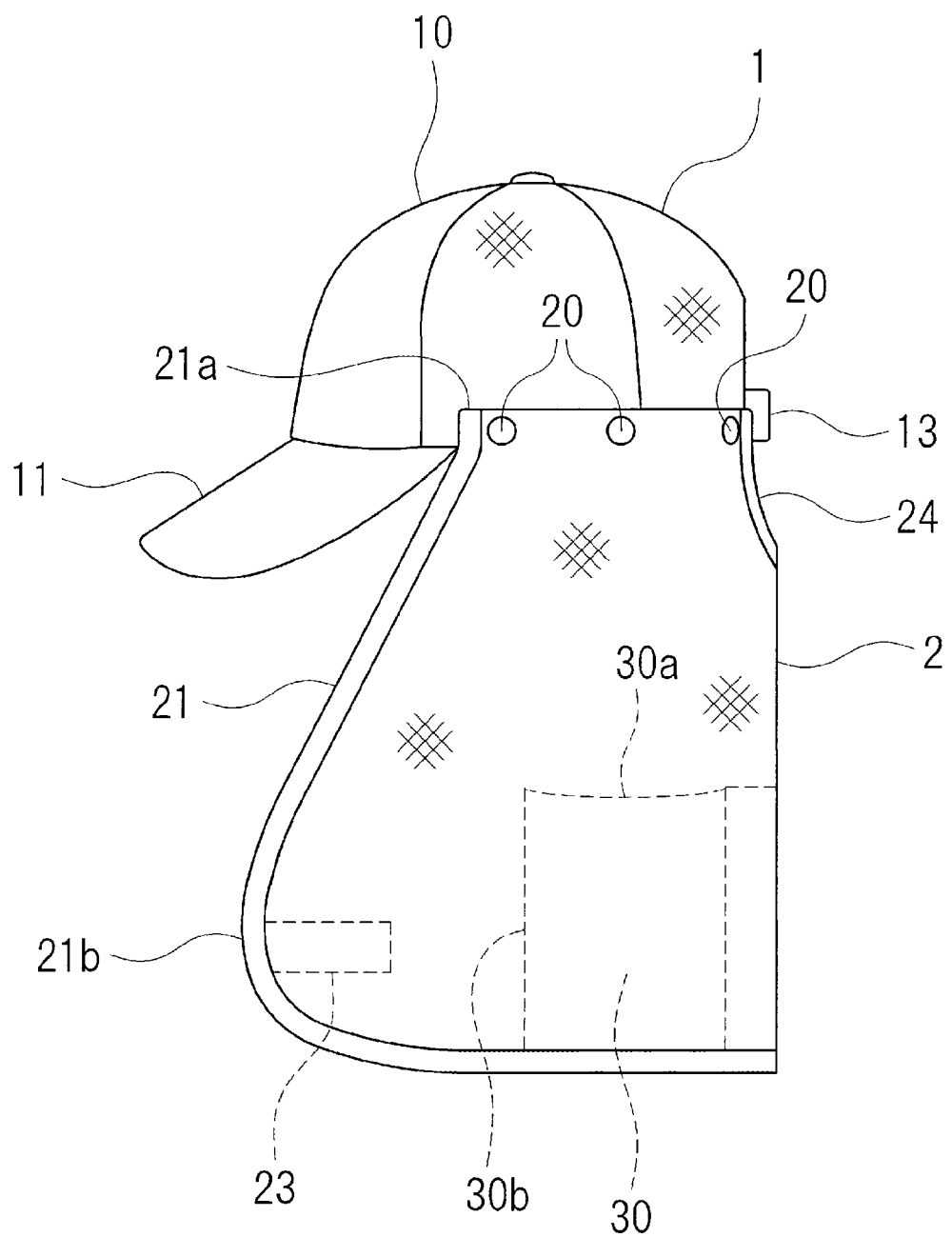
FIG. 3 is a side view of the headgear seen from a left side.
Figure 4:
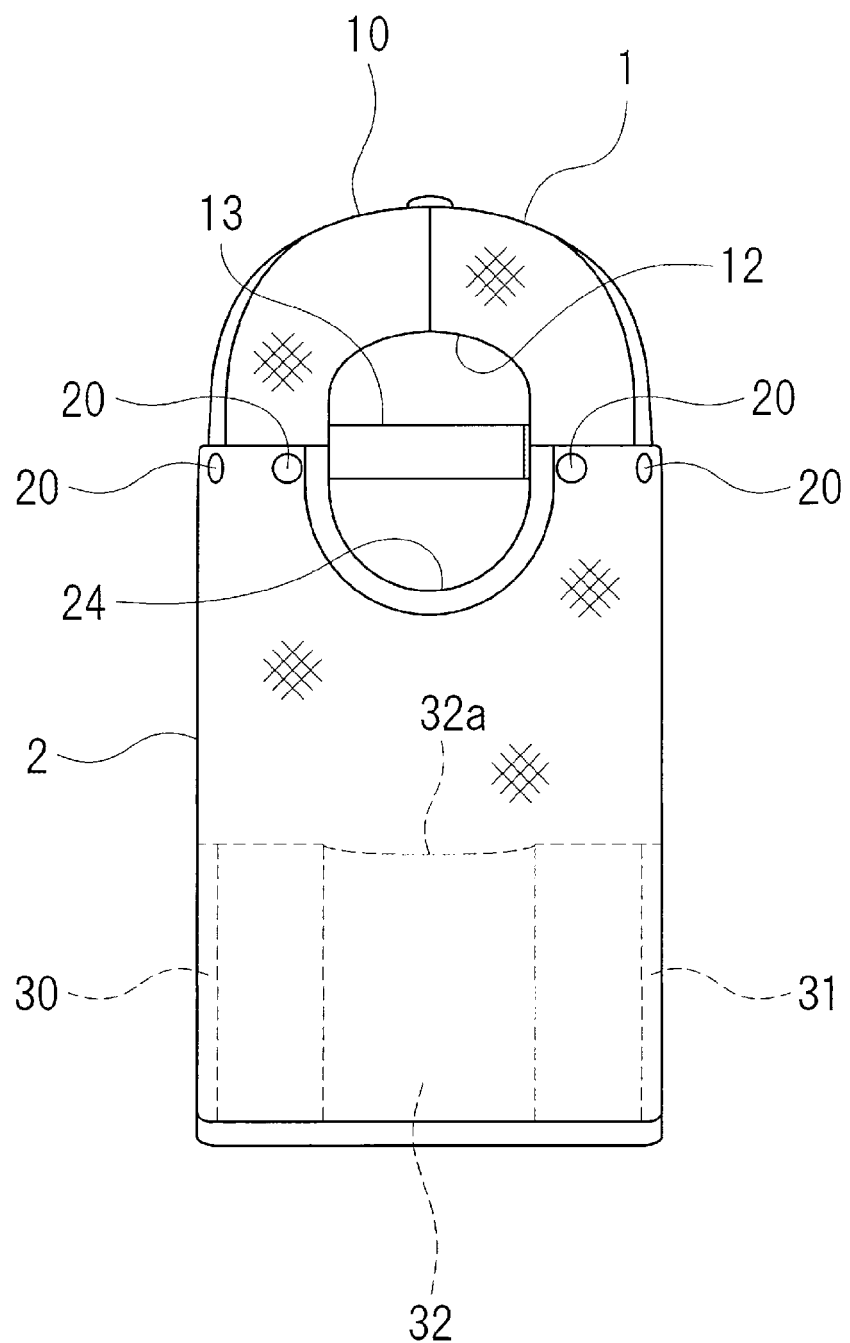
FIG. 4 is a rear view of the headgear seen from a rear side.
Figure 5:
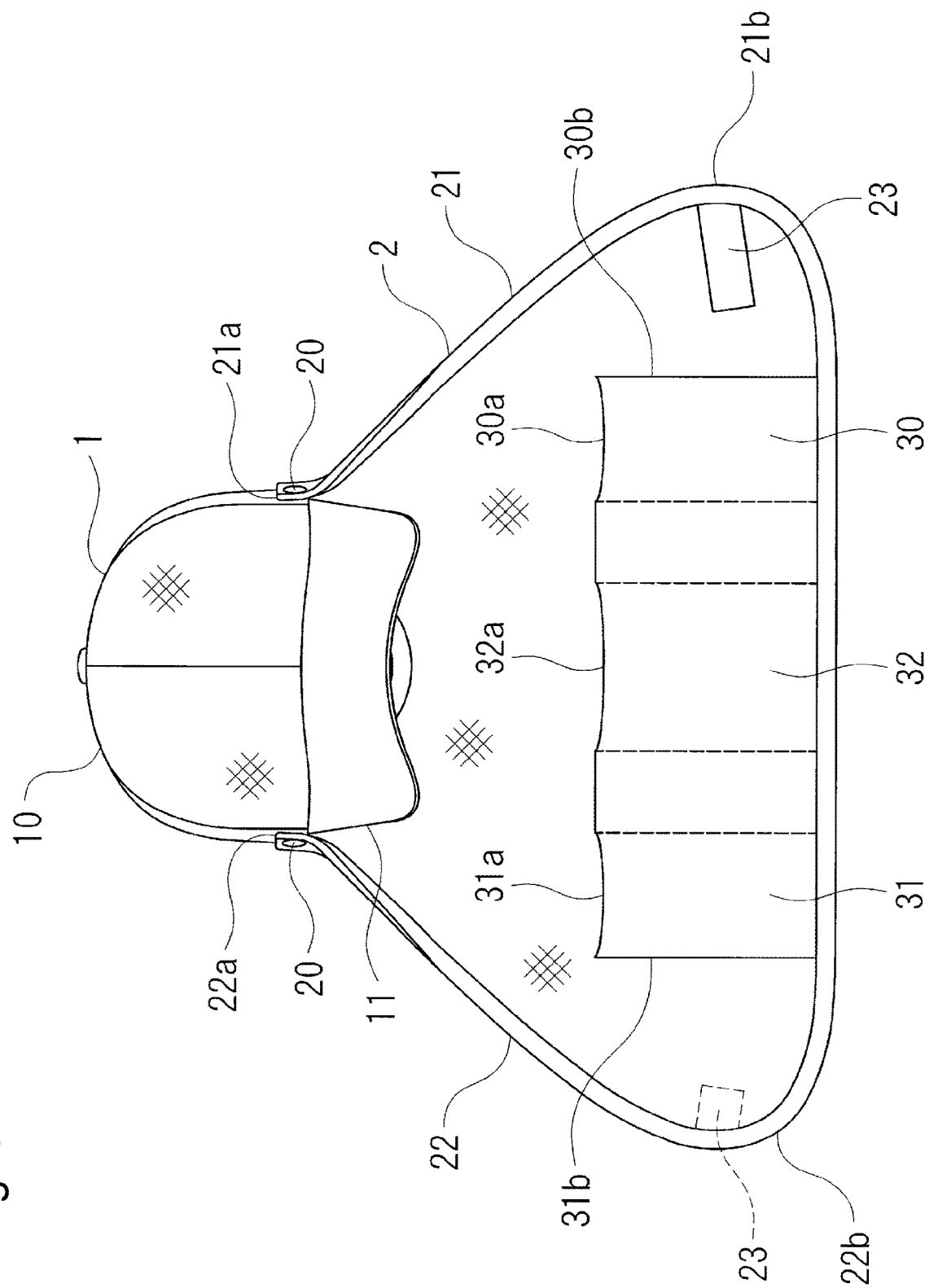
FIG. 5 is a front view of the headgear, illustrating a state where a neck cover is opened outwardly to the left and right.
Figure 6:
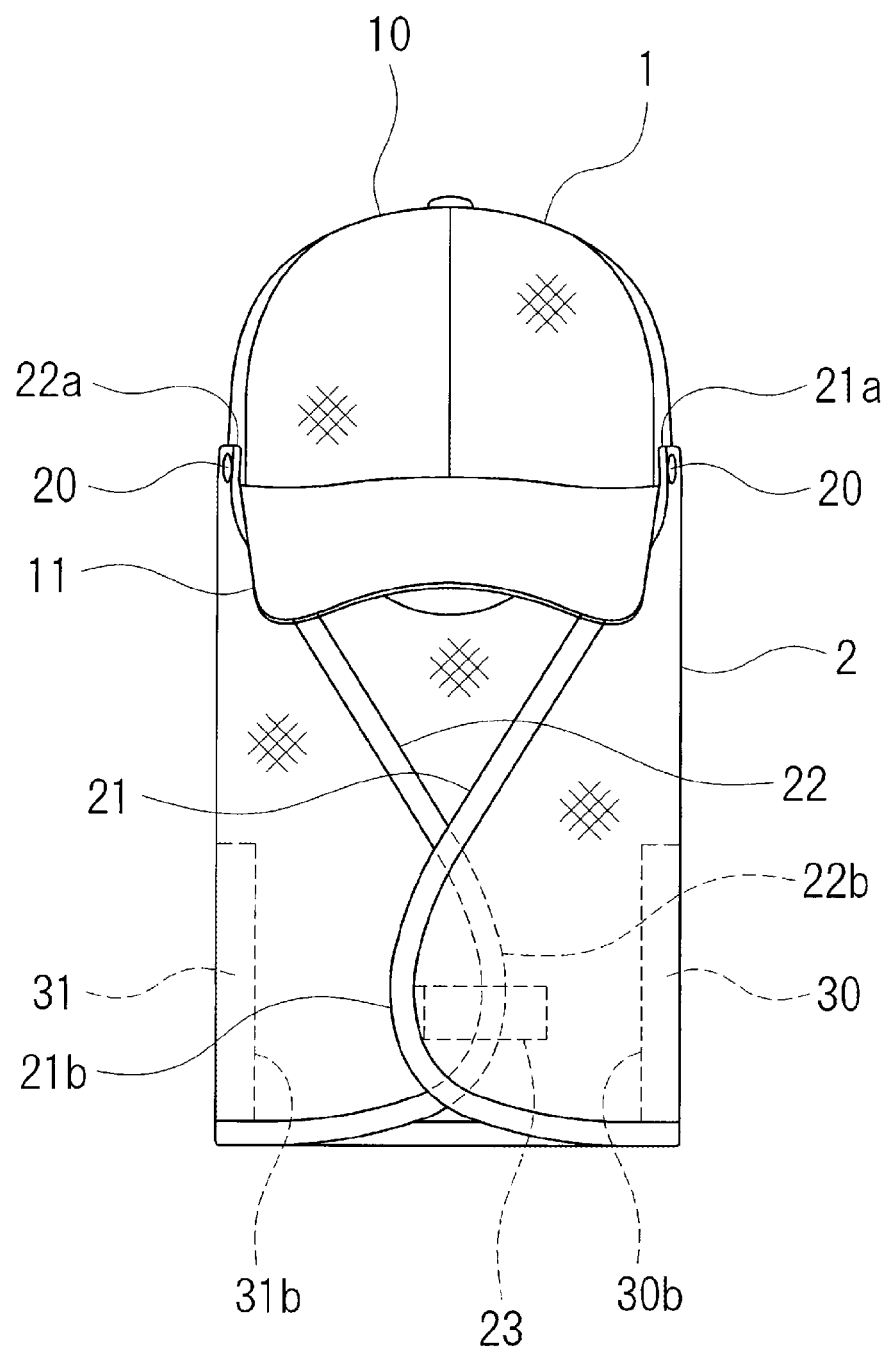
FIG. 6 is a front view of the headgear, illustrating a state where the neck cover is closed.
Figure 7:
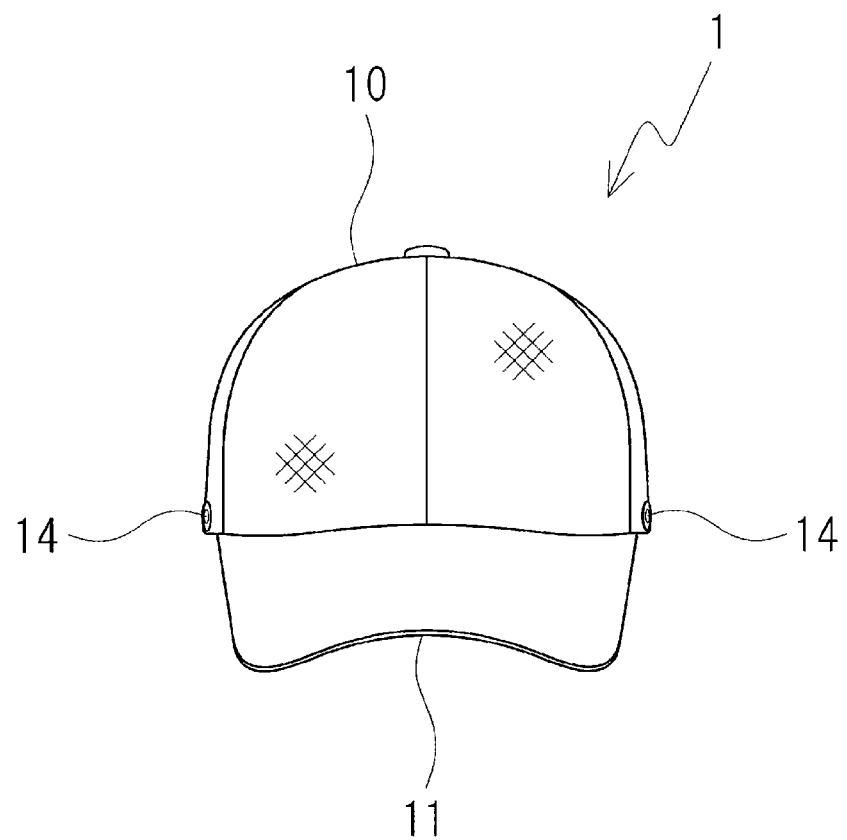
FIG. 7 is a front view of a headgear main body of the headgear.
Figure 8:
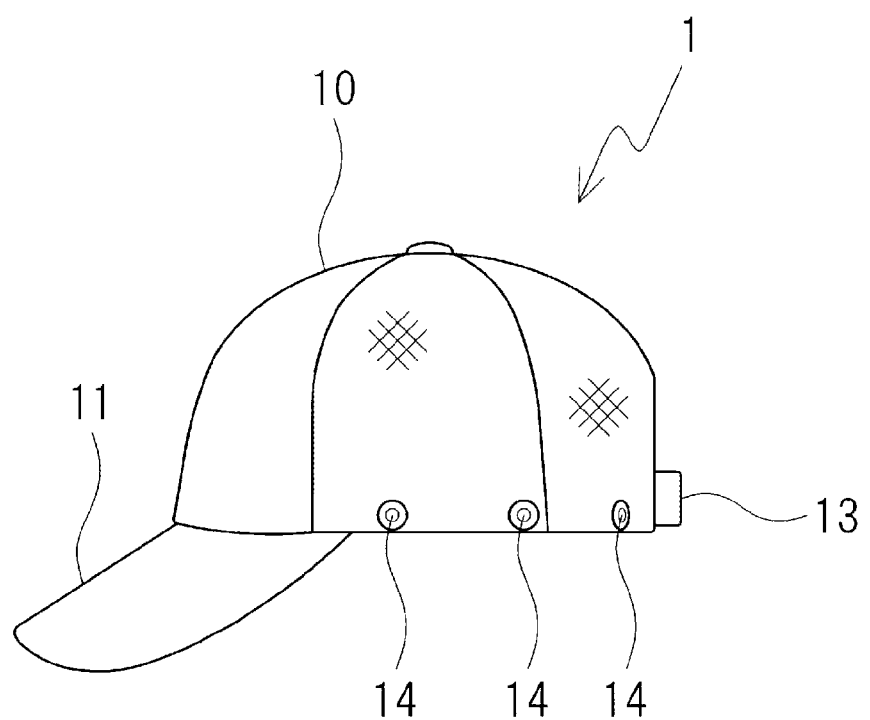
FIG. 8 is a side view of the headgear main body of the headgear.
Figure 9:
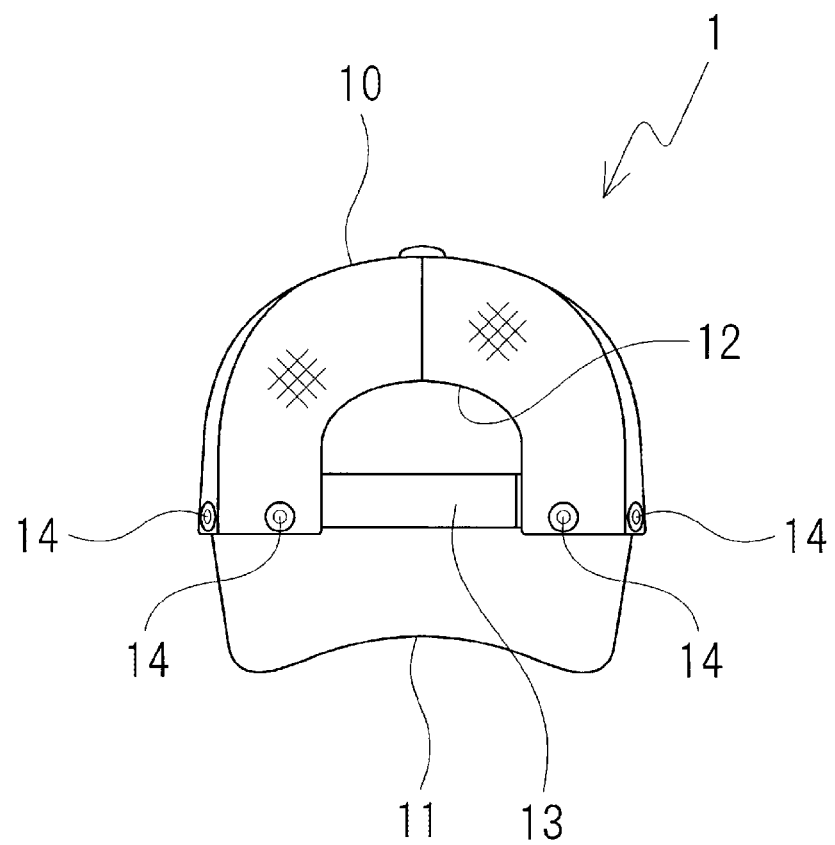
FIG. 9 is a rear view of the headgear main body of the headgear.
Figure 10:
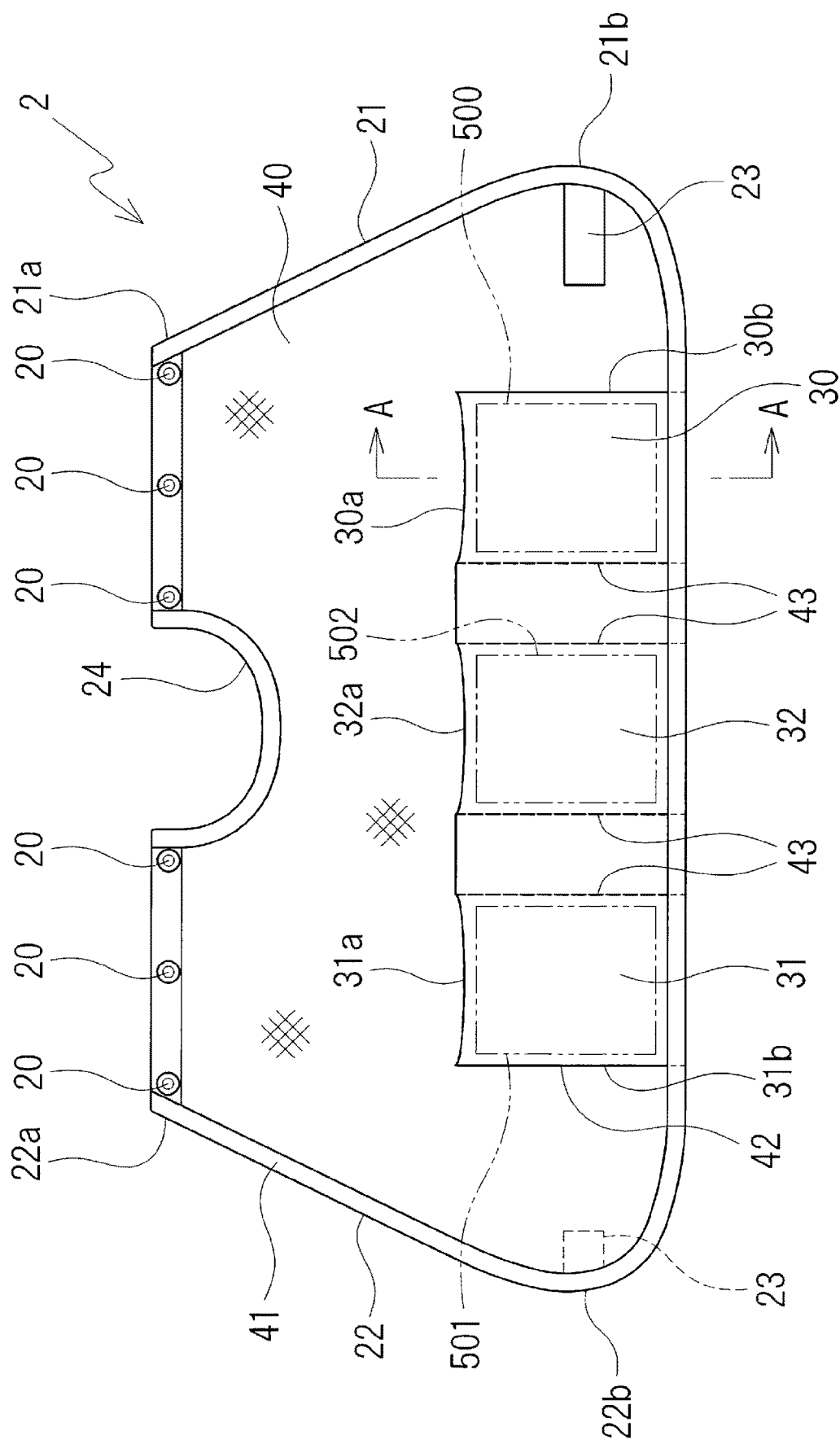
FIG. 10 is a developed view of the neck cover of the headgear, seen from a back surface side.
Figure 11A:
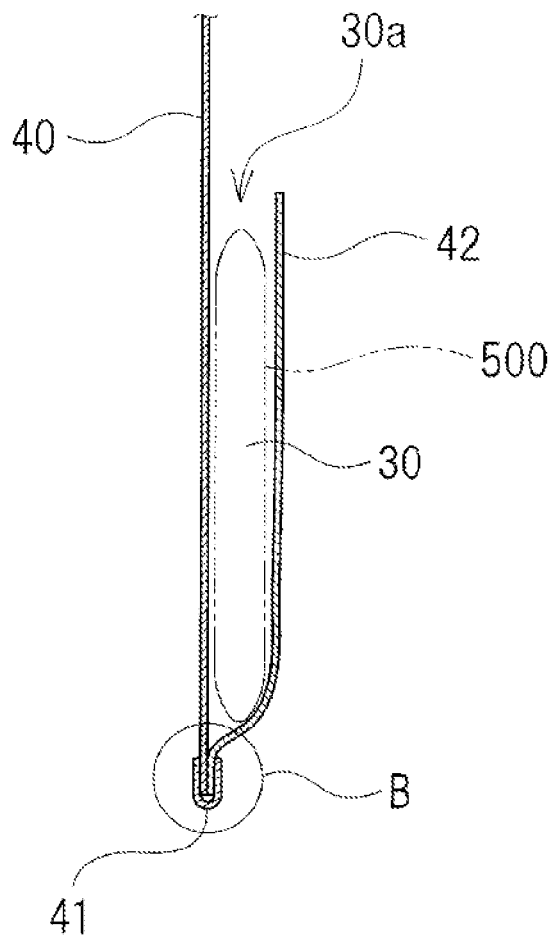
FIG. 11($a$) is a cross-sectional view taken along line A-A in FIG. 10, and FIG. 11($b$) is an enlarged view of a portion B in FIG. 11($a$).
Figure 11B:
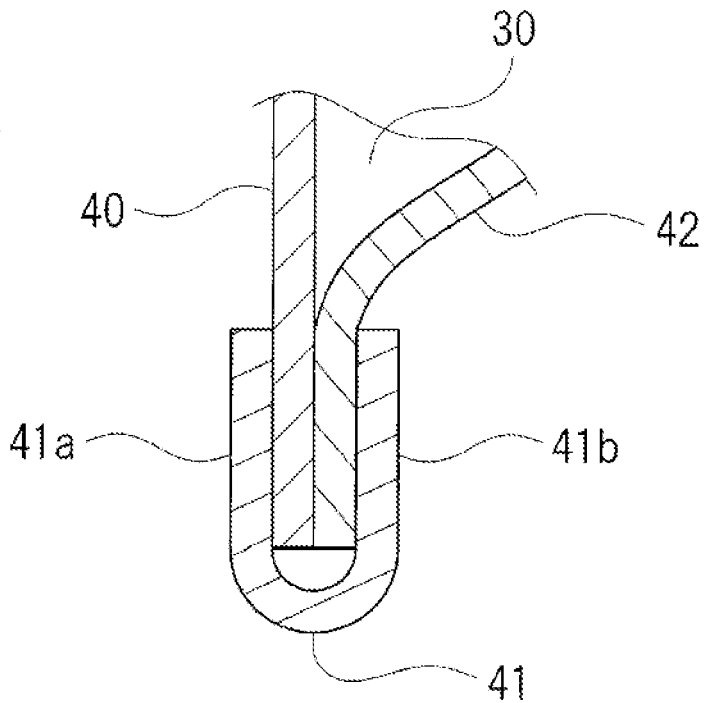

FIGS. 7 to 9 illustrate the headgear main body 1 alone. It is noted that FIGS. 7 to 9 illustrate a state where a lower end part of the headgear main body 1 is substantially horizontal. The headgear main body 1 has the shape of a cap and includes a brim part 11 in a front part. That is, the headgear main body 1 includes a major main body part 10 having a hemispherical shape that opens downward, and the brim part 11 that extends forward from a front part of a lower end part of the major main body part 10. It is noted that an opening part of the major main body part 10 is substantially circular. That is, the lower end part of the major main body part 10 is an opening edge part of the major main body part 10. The major main body part 10 is made of any type of fabrics. Various materials may be used for the fabric and a mesh material is an example of a material that is suitable for the fabric.

A main body notch part 12 that is directed upward is formed in a rear part of the lower end part of the headgear main body 1. The main body notch part 12 has a substantially semicircular shape. The headgear main body 1 is provided with an adjustment band 13 so as to bridge the main body notch part 12 in a left-right direction. The adjustment band 13 is composed of a pair of left and right band pieces. A hook-and-loop fastener (not illustrated) is attached to each of the left and right band pieces in the pair of band pieces. The adjustment band 13 makes it possible to increase and decrease a separation distance of the main body notch part 12 in the left-right direction, and thereby to increase and decrease a diameter of the opening part of the headgear main body 1. It is noted that various adjustment mechanisms may be used in the adjustment band 13. For example, the adjustment band 13 may be elastic. The elastic adjustment band 13 makes it possible to increase and decrease the separation distance of the main body notch part 12 in the left-right direction.

Dot buttons 14 are provided in the lower end part of the headgear main body 1. The dot buttons 14 are arranged at a plurality of locations at intervals in a circumferential direction of the opening part of the headgear main body 1. A plurality of the dot buttons 14 are arranged at equal intervals in each of two left and right sections between left and right end parts of the brim part 11 and the adjustment band 13. Specifically, the dot buttons 14 are arranged at six locations in total, that is, at positions close to both end parts of the adjustment band 13, positions close to the left and right end parts of the brim part 11, and positions between the positions close to the end parts of the adjustment band 13 and the positions close to the left and right end parts of the brim part 11. Accordingly, three of the dot buttons 14 are provided in each of the left and right sections, and the dot buttons 14 are arranged symmetrically. The dot buttons 14 are attached so that a front surface of the headgear main body 1 serves as an attachment surface.

<Neck Cover 2>

The neck cover 2 covers the neck 610. Specifically, the neck cover 2 covers at least a rear half region of the entire circumference of the neck 610. The neck cover 2 is suspended downward from the lower end part of the headgear main body 1. The neck cover 2 may be integrally formed with the headgear main body 1 or may be formed separately from the headgear main body 1. In the present embodiment, the neck cover 2 is formed separately from the headgear main body 1. The neck cover 2 may be sewn inseparably to the headgear main body 1, but in the present embodiment, the neck cover 2 is attachable to and detachable from the headgear main body 1. Attachment and detachment of the neck cover 2 to and from the headgear main body 1 may be realized by various means, but in the present embodiment, the dot buttons 14 and dot buttons 20 are adopted. However, instead of the dot buttons 14 and 20, various types of buttons, hook-and-loop fasteners, slide fasteners, and the like may be used.

The dot buttons 20 of the neck cover 2 are attached to the neck cover 2 so that a back surface of the neck cover 2 serves as an attachment surface. Accordingly, the neck cover 2 is attached to the front surface of the headgear main body 1. The dot buttons 20 of the neck cover 2 are attached to an upper end part of the neck cover 2.

The neck cover 2 is positioned under a region obtained as the entire circumference of the lower end part of the headgear main body 1 excluding a part where the brim part 11 is provided. When the region obtained as the entire circumference of the lower end part of the headgear main body 1 excluding the part where the brim part 11 is provided, is referred to as an open region, the neck cover 2 is positioned under the entire open region. The neck cover 2 is configured to continuously extend in the circumferential direction of the lower end part of the headgear main body 1. When attached to the headgear main body 1, the neck cover 2 is curved along the lower end part of the headgear main body 1.

A left end part 21 and a right end part 22 of the neck cover 2 face the front side when the neck cover 2 is attached to the headgear main body 1. The neck cover 2 extends around a rear side of the neck 610. An upper end part 21a of the left end part 21 and an upper end part 22a of the right end part 22 of the neck cover 2 are positioned near the left and right end parts of the brim part 11. The left end part 21 of the neck cover 2 inclines so as to extend from the upper end part 21a downward and to the front as a whole. A lower part of the left end part 21 of the neck cover 2 extends more to the front than the upper end part 21a of the left end part 21 of the neck cover 2. The lower part of the left end part 21 of the neck cover 2 is provided with a left extension part 21b extending more to the front than the upper end part 21a of the left end part 21. The right end part 22 of the neck cover 2 inclines so as to extend from the upper end part 22a downward and to the front as a whole. A lower part of the right end part 22 of the neck cover 2 extends more to the front than the upper end part 22a of the right end part 22 of the neck cover 2. The lower part of the right end part 22 of the neck cover 2 is provided with a right extension part 22b extending more to the front than the upper end part 22a of the right end part 22.

Hook-and-loop fastener 23 are provided on each of the left extension part 21b and the right extension part 22b of the neck cover 2. The left extension part 21b and the right extension part 22b are detachably coupled by the hook-and-loop fasteners 23. The hook-and-loop fasteners 23 are coupling parts for detachably coupling the left end part 21 and the right end part 22 of the neck cover 2, on the front side of the neck 610.

A length of the upper end part of the neck cover 2 in the left-right direction corresponds to a length of the open region of the headgear main body 1 in the left-right direction. A length of a lower end part of the neck cover 2 in the left-right direction is longer than a length of the upper end part of the neck cover 2 in the left-right direction. The lower end part of the neck cover 2 has a length in the left-right direction allowing for the neck cover 2 to surround the entire circumference of the neck 610. The neck cover 2 has dimensions in an up-down direction allowing for the neck cover 2 to reach a lower neck or a shoulder 611 in a worn state. The dimensions of the neck cover 2 in the up-down direction are larger than dimensions of the headgear main body 1 in the up-down direction, and are about twice the dimensions of the headgear main body 1 in the up-down direction.

A cover notch part 24 is formed in a rear part of the upper end part of the neck cover 2 so as to face downward. The cover notch part 24 has a substantially semicircular shape. The cover notch part 24 corresponds to the main body notch part 12 and is positioned under the main body notch part 12.

<Holding Parts>

The headgear includes first to third pockets 30, 31, and 32 capable of holding first to third cooling members 500, 501, and 502. The first to third pockets 30, 31, and 32 are first to third holding parts for holding the first to third cooling members 500, 501, and 502. The first cooling member 500 is stored in the first pocket 30, the second cooling member 501 is stored in the second pocket 31, and the third cooling member 502 is stored in the third pocket 32.

The first to third pockets 30, 31, and 32 are provided in a lower part of the neck cover 2. The first to third cooling members 500, 501, and 502 may be of various types, and examples thereof include an ice pack and ice. In the present embodiment, as a typical example, a case where the first to third cooling members 500, 501, and 502 are ice packs will be described. The ice pack is used after being cooled in a refrigerator or a freezer. The ice pack has a plate-like rectangular shape, for example. The ice pack is preferably soft and flexible in a chilled state, and particularly preferably is soft and flexible even in a frozen state in a freezer.

The first to third pockets 30, 31, and 32 are positioned in a lower half region of the neck cover 2. The first to third pockets 30, 31, and 32 have a vertically elongated rectangular shape, but may have any shape and size. Any number of pockets may be provided. The first to third pockets 30, 31, and 32 are provided at intervals in the left-right direction. The first to third pockets 30, 31, and 32 have storage spaces that are independent of each other. One of the first to third cooling members 500, 501, and 502 can be stored in each of the first to third pockets 30, 31, and 32. The first to third cooling members 500, 501, and 502 are stored in the first to third pockets 30, 31, and 32 in a vertical orientation, that is, in an orientation in which a long side direction is the up-down direction. The first to third pockets 30, 31, and 32 include opening parts 30*a*, 31*a*, and 32*a* at upper end parts thereof. The first to third cooling members 500, 501, and 502 are introduced into and removed from the first to third pockets 30, 31, and 32 via the opening parts 30*a*, 31*a*, and 32*a* of the first to third pockets 30, 31, and 32. The first to third pockets 30, 31, and 32 are provided on a back surface side (inner surface side) of the neck cover 2. A distance by which the first to third pockets 30, 31, and 32 are separated in the left-right direction is smaller than the dimensions of the first to third pockets 30, 31, and 32 in the left-right direction.

The first to third pockets 30, 31, and 32 are provided symmetrically in the left-right direction. The first pocket 30 is provided on the left side, the second pocket 31 is provided on the right side, and the third pocket 32 is provided between the first pocket 30 and the second pocket 31. The first pocket 30 and the second pocket 31 are arranged symmetrically to each other in the left-right direction. The third pocket 32 is arranged in the middle between the first and second pockets 30 and 31. One of the hook-and-loop fasteners 23 is positioned in front of the first pocket 30 (on a side of the left end part 21), and one of the hook-and-loop fasteners 23 is positioned in front of the second pocket 31 (on a side of the right end part 22). Positions of the hook-and-loop fasteners 23 in the up-down direction are positions corresponding to a region between the upper end part and the lower end part of the first to third pockets 30, 31, and 32.

The first pocket 30 is positioned vertically below a position between the upper end part 21*a* of the left end part 21 of the neck cover 2 and the cover notch part 24. A front side edge part 30*b* of the first pocket 30 is positioned near a region vertically below the upper end part 21*a* of the left end part 21 of the neck cover 2. The front side edge part 30*b* of the first pocket 30 is preferably positioned in a range within 3 cm to the left and right of the region vertically below the upper end part 21*a* of the left end part 21 of the neck cover 2. Specifically, the front side edge part 30*b* of the first pocket 30 is positioned slightly rearward of the position of the region vertically below the upper end part 21*a* of the left end part 21 of the neck cover 2. The first pocket 30 is positioned so as to face a side of a left carotid artery 600 of a wearer in a worn state where the headgear is worn on a head. It is noted that left and right carotid arteries 600 and 601 are positioned below the ears.

The second pocket 31 is positioned vertically below the position between the upper end part 22*a* of the right end part 22 of the neck cover 2 and the cover notch part 24. A front side edge part 31*b* of the second pocket 31 is positioned near a region vertically below the upper end part 22*a* of the right end part 22 of the neck cover 2. The front side edge part 31*b* of the second pocket 31 is preferably positioned in a range within 3 cm in the left-right direction of the region vertically below the upper end part 22*a* of the right end part 22 of the neck cover 2. Specifically, the front side edge part 31*b* of the second pocket 31 is positioned slightly rearward of the position of the region vertically below the upper end part 22*a* of the right end part 22 of the neck cover 2. The second pocket 31 is positioned so as to face a side of the right carotid artery 601 of the wearer in the worn state. The third pocket 32 is positioned vertically below the cover notch part 24. The third pocket 32 is positioned so as to face the rear of a rear center part of the lower neck of the wearer in the worn state.

The neck cover 2 is made of any type of fabrics. For example, a mesh material is suitable as the fabric. The neck cover 2 can be made of the same fabric as the headgear main body 1. The neck cover 2 includes a first piece 40, a second piece 41 bordering an edge part of the first piece 40, and a third piece 42 used for forming the first to third pockets 30, 31, and 32. The first piece 40 generally forms the neck cover 2. The first piece 40 is made of any type of fabrics. The first piece 40 is preferably made of a mesh material, for example. The second piece 41 is sewn to the edge part of the first piece 40. The second piece 41 extends along the edge part of the first piece 40. The second piece 41 is made of any type of fabrics. The second piece 41 can be made of the same fabric as the first piece 40, for example. The second piece 41 is band-shaped. The second piece 41 is folded in half in a width direction. The second piece 41 is composed of a front piece 41*a* and a back piece 41*b* that have the same width. The front piece 41*a* of the second piece 41 is positioned on a front surface side of the first piece 40. The back piece 41*b* of the second piece 41 is positioned on a back surface side of the first piece 40. The second piece 41 sandwiches the edge part of the first piece 40 in a front-back direction.

The third piece 42 is sewn to the back surface side of the first piece 40. The third piece 42 is made of any type of fabrics. The third piece 42 can be made of the same fabric as the first piece 40. Furthermore, the third piece 42 is preferably thicker than the first piece 40. That is, it is preferable that the fabric positioned on the front side of the cooling members is thicker than the fabric positioned on the back side of the cooling members. When a mesh material such as described above is used for the first piece 40 to obtain good air permeability, no mesh material may be used for the third piece 42 and the third piece 42 may have lower air permeability than the first piece 40. That is, it is preferable that the fabric positioned on the front side of the cooling members has higher air permeability than the fabric positioned on the back side of the cooling members. Accommodation spaces of the first to third pockets 30, 31, and 32 are formed between the first piece 40 and the third piece 42. In the present embodiment, the third piece 42 is formed of a single piece of fabric that is elongated in the left-right direction (horizontal direction). Predetermined locations of the third piece 42 in the left-right direction are sewn to the first piece 40 along the up-down direction (vertical direction). The space between the third piece 42 and the first piece 40 is divided in the left-right direction by sewn parts 43 in the vertical direction, and thus, the first to third pockets 30, 31, and 32 are partitioned and formed.

A lower end part of the third piece 42 and the first piece 40 are bordered by the second piece 41. The lower end part of the third piece 42 overlaps with the back surface side of the lower end part of the first piece 40. The lower end part of the third piece 42 is positioned at the lower end part of the neck cover 2. That is, the lower end parts of the first to third pockets 30, 31, and 32 are positioned at the lower end part of the neck cover 2. In the lower end part of the neck cover 2, the front piece 41*a* of the second piece 41, the first piece 40, the third piece 42, and the back piece 41*b* of the second piece 41 are positioned in this order from the front surface side. The front piece 41*a* of the second piece 41, the first piece 40, the third piece 42, and the back piece 41*b* of the second piece 41 overlap each other. The lower end parts of the first to third pockets 30, 31, and 32 have a multi-layered structure in which the front piece 41*a* of the second piece 41, the first piece 40, the third piece 42, and the back piece 41*b* of the second piece 41 overlap in the front-back direction.

Figure 12:
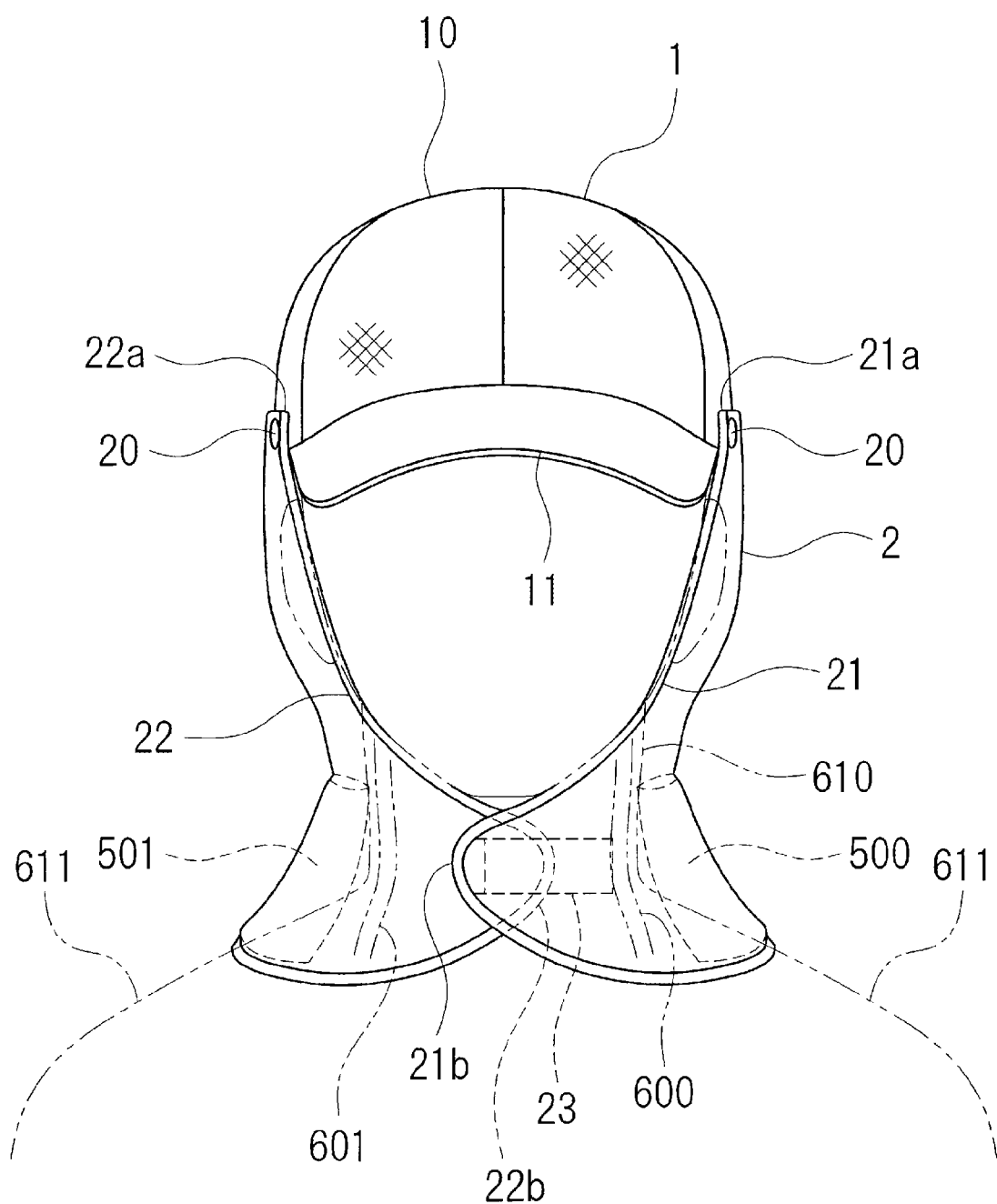
FIG. 12 is a front view illustrating a worn state of the headgear.
Figure 13:
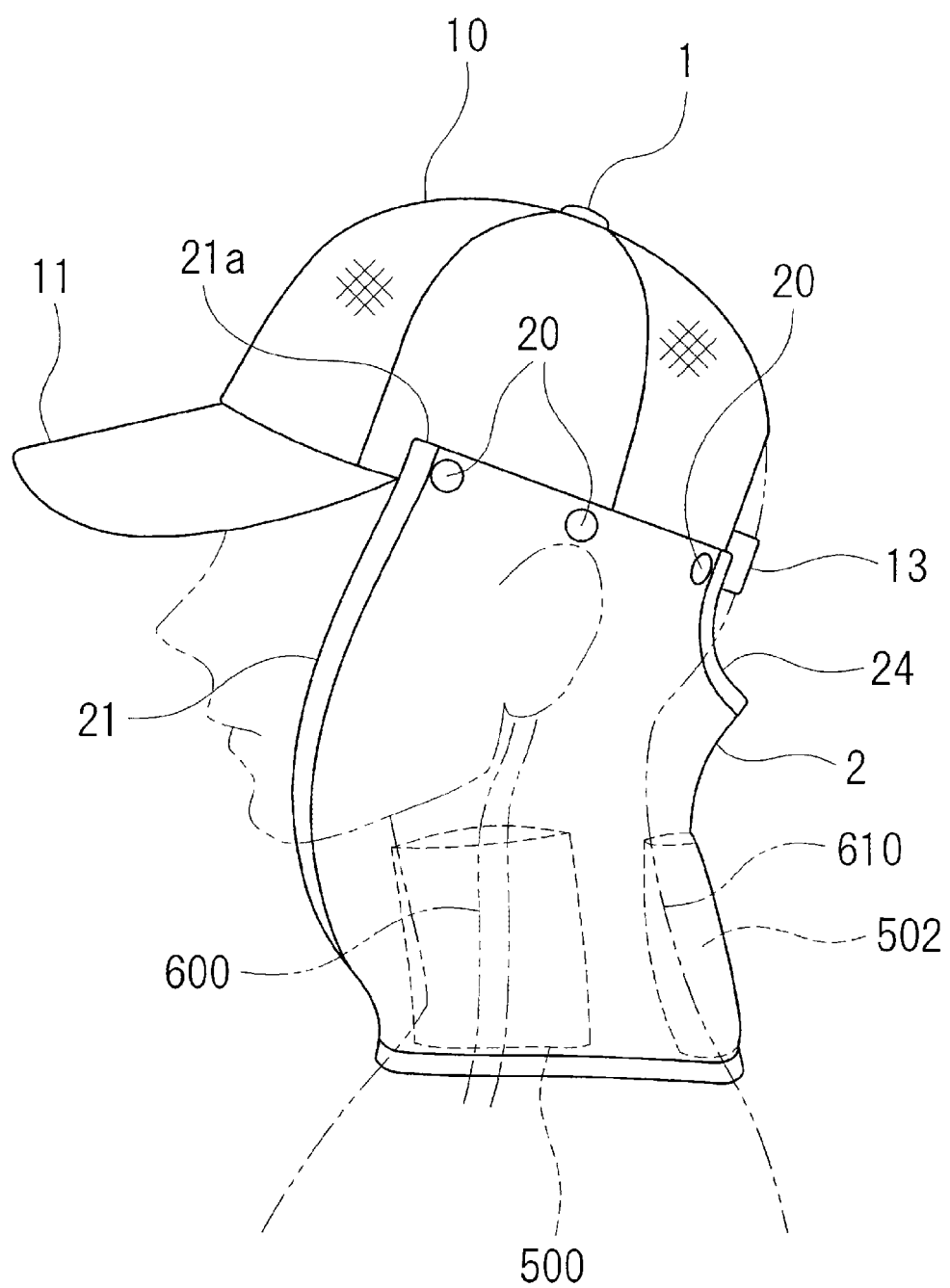
FIG. 13 is a side view illustrating the worn state of the headgear.
Figure 14:
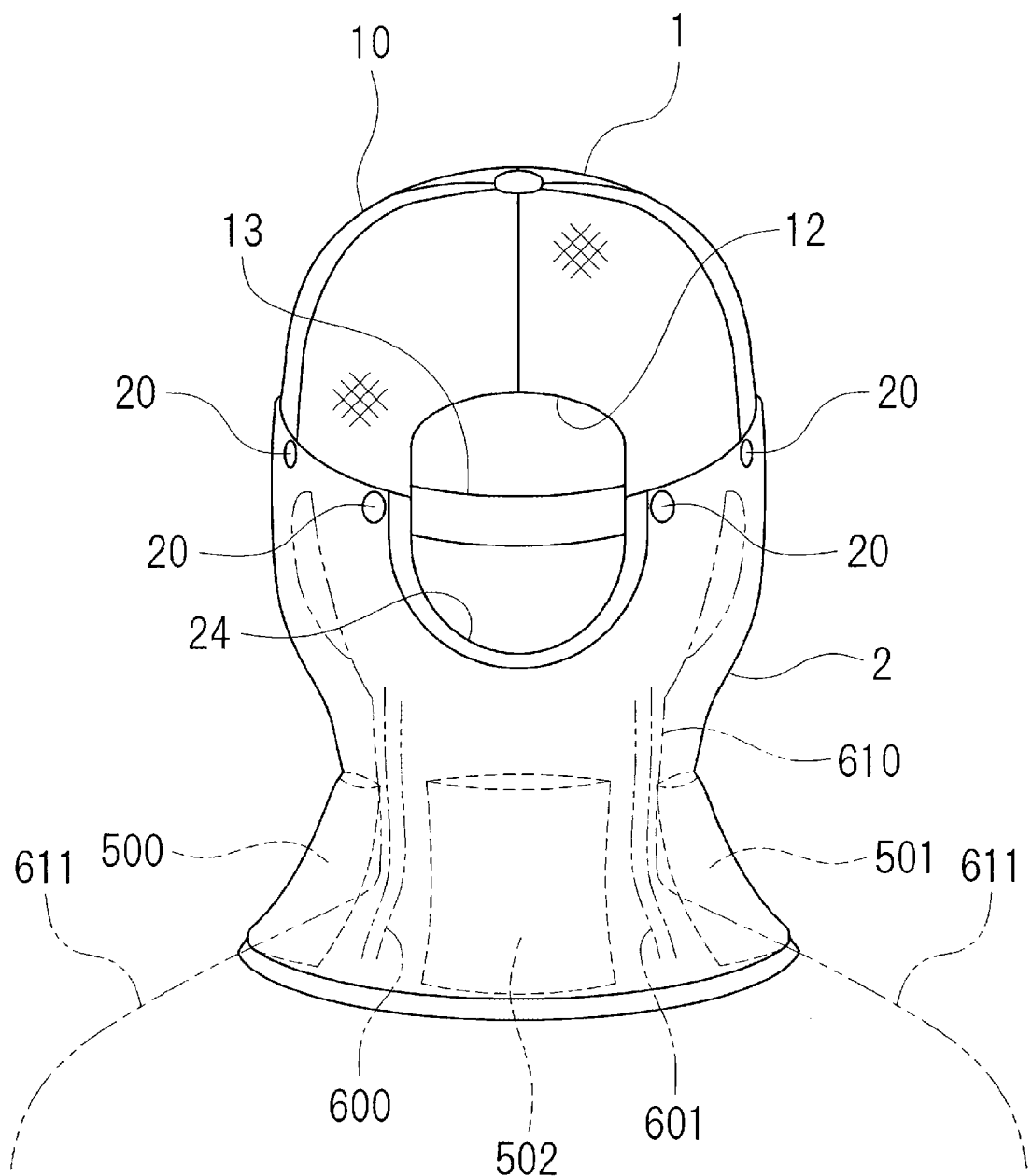
FIG. 14 is a rear view illustrating the worn state of the headgear.

FIGS. 12 to 14 illustrate a worn state of the headgear. It is noted that, in FIGS. 12 to 14, the first to third pockets 30, 31, and 32 are not illustrated. When the headgear is worn, the first to third cooling members 500, 501, and 502 are stored in the first to third pockets 30, 31, and 32. The drawings illustrate a state where the first to third cooling members 500, 501, and 502 having a rectangular shape are each individually stored in a vertical orientation in the first to third pockets 30, 31, and 32. However, a plurality of the first to third cooling members 500, 501, and 502 having a smaller size than those illustrated in the drawings may be stored in the first to third pockets 30, 31, and 32.

The headgear main body 1 is worn on a head. As illustrated in FIG. 13, in general, the lower end part of the headgear main body 1 is slightly inclined to the rear side in the worn state. In the worn state, the lower end part of the neck cover 2 reaches the shoulder 611. The hook-and-loop fasteners 23 can couple the left extension part 21b and the right extension part 22b of the neck cover 2 at a position on the front side of the neck 610, for example. When the left extension part 21b and the right extension part 22b of the neck cover 2 are coupled, the neck cover 2 covers the entire circumference of the neck 610.

As illustrated in FIGS. 12 to 14, the first cooling member 500 faces the left carotid artery 600 in the worn state. Similarly, the second cooling member 501 faces the right carotid artery 601. The third cooling member 502 faces, from the rear, a rear part of the lower neck. It is noted that the first to third cooling members 500, 501, and 502 may contact the neck 610 or may be spaced from the neck 610. A stop position of the hook-and-loop fasteners 23 can be adjusted to adjust a distance by which the neck 610 and the first to third cooling members 500, 501, and 502 are separated. Furthermore, the lower end parts of the first and second cooling members 500 and 501 respectively contact the left and right shoulders 611 or the lower neck. The first and second cooling members 500 and 501 are supported by the left and right shoulders 611 or the lower neck, and are placed on the left and right shoulders 611 or the lower neck. The lower end part of the third cooling member 502 contacts a region from the rear part of the lower neck to an upper part of a back, and the third cooling member 502 is supported by the region from the rear part of the lower neck to the upper part of the back.

Figure 15:
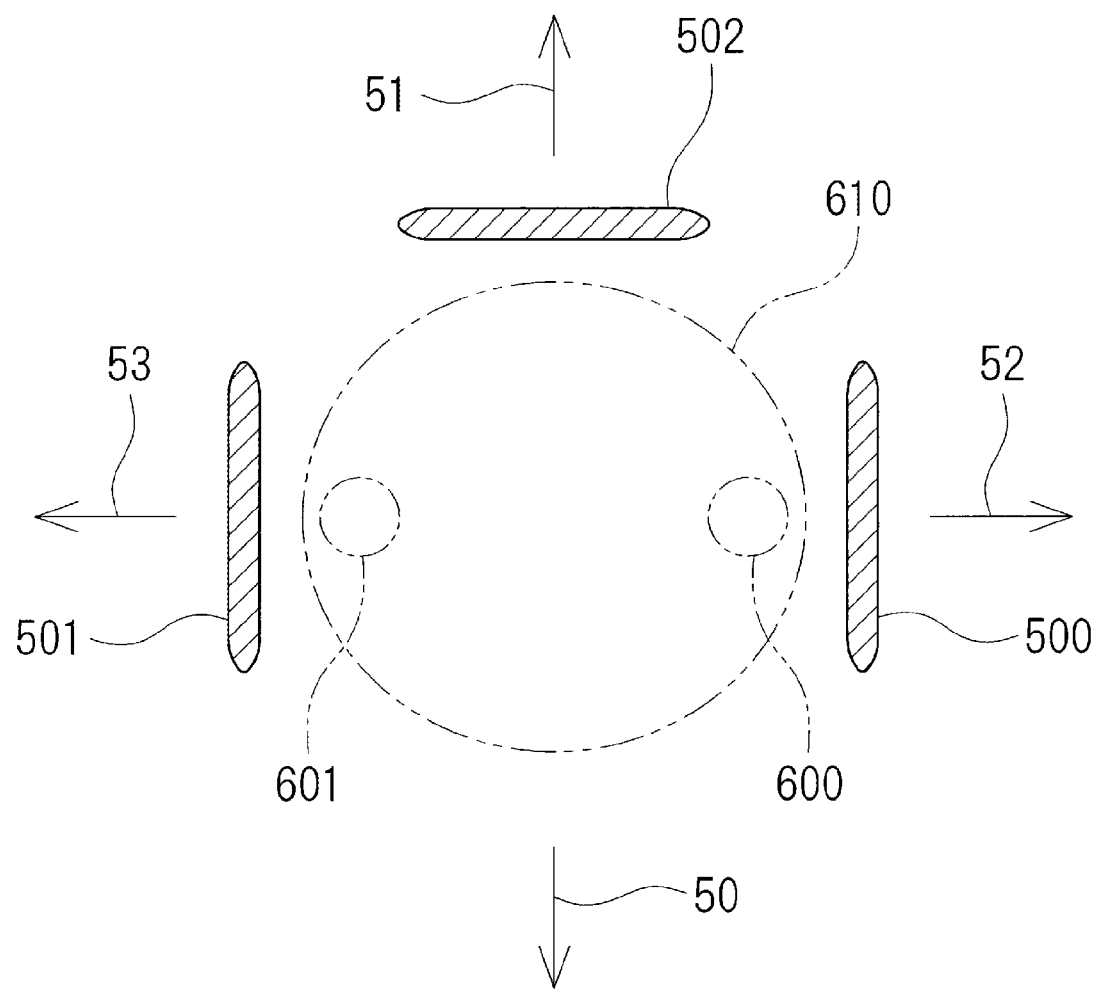
FIG. 15 is a cross-sectional view schematically illustrating, in a plane view, an arrangement of cooling members in the worn state of the headgear.

FIG. 15 schematically illustrates an arrangement of the neck 610 and the first to third cooling members 500, 501, and 502. In FIG. 15, front, back, left, and right directions are indicated by arrows. The front side is indicated by an arrow 50, the rear side is indicated by an arrow 51, the left side is indicated by an arrow 52, and the right side is indicated by an arrow 53. In the worn state, the first and second cooling members 500 and 501 face each other in the left-right direction. The thickness direction of the first and second cooling members 500 and 501 is substantially the left-right direction. One side of the two sides of the first cooling member 500 and one side of the two sides of the second cooling member 501 face the carotid artery 600 and the carotid artery 601, respectively. The thickness direction of the third cooling member 502 is substantially the front-rear direction. The first to third cooling members 500, 501, and 502 cool the lower neck from the left, right, and rear sides, that is, from three sides.

As described above, it is possible to simultaneously cool the left and right carotid arteries 600 and 601 by the first and second cooling members 500 and 501. The left and right carotid arteries 600 and 601 are blood vessels leading from the heart to the brain. Therefore, heatstroke can be effectively prevented by cooling the left and right carotid arteries 600 and 601 with the first and second cooling members 500 and 501. The first and second cooling members 500 and 501 are positioned on the left and right, respectively, and thus, the left-right balance of the headgear is excellent, the headgear is easily stabilized, and the burden on the wearer is reduced. The first and second cooling members 500 and 501 having a relatively small size can be arranged in a distributed manner to the left and right, and thus, it is possible to prevent excessive weight increase and reduce the burden on the wearer. If the first and second cooling members 500 and 501 are oriented vertically, as in the present embodiment, it is possible to cool the left and right carotid arteries 600 and 601 in a long section. Furthermore, the rear part of the lower neck can also be cooled at the same time by the third cooling member 502. The neck cover 2 covers the left and right side parts of the face, the ears, and further, covers the neck 610 over the entire circumference, and thus, it is possible to surely block sunlight shining on these locations. The first to third cooling members 500, 501, and 502 are arranged at three locations, that is, at locations on the left, right, and rear, respectively, and thus, a suspended state of the neck cover 2 can be stabilized by the weight of the first to third cooling members 500, 501, and 502. For example, even in strong wind, the lower part of the neck cover 2 is prevented from rolling up, and sunlight shining on the lower neck can be surely blocked. On the other hand, the first to third cooling members 500, 501, and 502 are supported by the shoulders 611, the lower neck, and the upper part of the back, and thus, the postures and positions of the first to third cooling members 500, 501, and 502 are stable. Moreover, the first to third cooling members 500, 501, and 502, which are heavy objects, are supported by the shoulders 611 and the like, and thus, the burden on the neck 610 and the head is small. Furthermore, the first to third cooling members 500, 501, and 502 are spaced from each other to the left and right, and thus, when the first piece 40 and the third piece 42 are both made of mesh material, a portion between adjacent ones of the sewn parts 43 functions as an air-permeable part.

It is possible to couple the left extension part 21b and the right extension part 22b of the neck cover 2 by the hook-and-loop fasteners 23, and thus, the left extension part 21b and the right extension part 22b of the neck cover 2 are less likely to flutter due to wind or the like. When the left extension part 21b and the right extension part 22b of the neck cover 2 are coupled by the hook-and-loop fasteners 23, the positions and postures of the first to third cooling members 500, 501, and 502 are also stabilized. Furthermore, positioning the first to third cooling members 500, 501, and 502 close to the neck 610 can be easily achieved, and the positions and postures of the first to third cooling members 500, 501, and 502 can be easily maintained. Even if the hook-and-loop fasteners 23 are disengaged and the left extension part 21b and the right extension part 22b are separated from each other, the suspended state of the neck cover 2 is easily stabilized by the weight of the first and second cooling members 500 and 501. Furthermore, if the third cooling member 502 is also arranged on the rear side and a total of three cooling members, that is, the first to third cooling members 500, 501, and 502 are provided, the suspended state of the neck cover 2 can even more easily be stabilized. When the suspended state of the neck cover 2 is stable, the positions of the first to third cooling members 500, 501, and 502 are stabilized. In particular, when the positions of the first and second cooling members 500 and 501 are stable, it is possible to stably cool the left and right carotid arteries 600 and 601. Furthermore, the front side edge part 30b of the first pocket 30 and the front side edge part 31b of the second pocket 31 are positioned near regions vertically below the upper end part 21a of the left end part 21 and the upper end part 22a of the right end part 22 of the neck cover 2. Therefore, the left extension part 21b and the right extension part 22b of the neck cover 2 can be easily coupled, using the front side edge part 30b of the first pocket 30 and the front side edge part 31b of the second pocket 31 as fulcrums.

Second Embodiment

Figure 16:
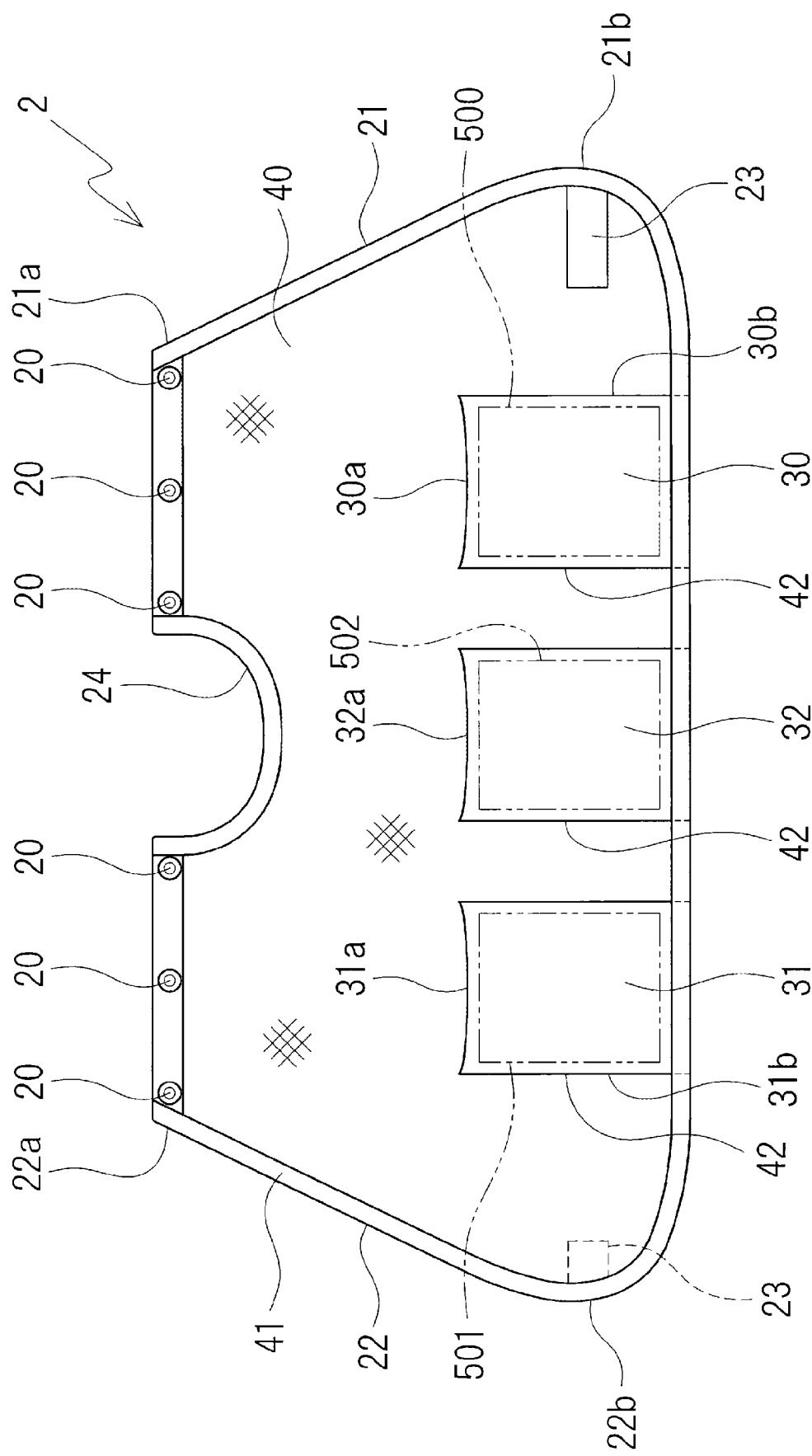
FIG. 16 is a developed view of a neck cover of a headgear according to a second embodiment of the present invention, seen from a back surface side.

It is noted that, in the first embodiment, the third piece 42 is formed of a single piece of fabric. However, as illustrated in FIG. 16, the third piece 42 may be provided as an individual piece for each of the first to third pockets 30, 31, and 32.

Third Embodiment

Figure 17:
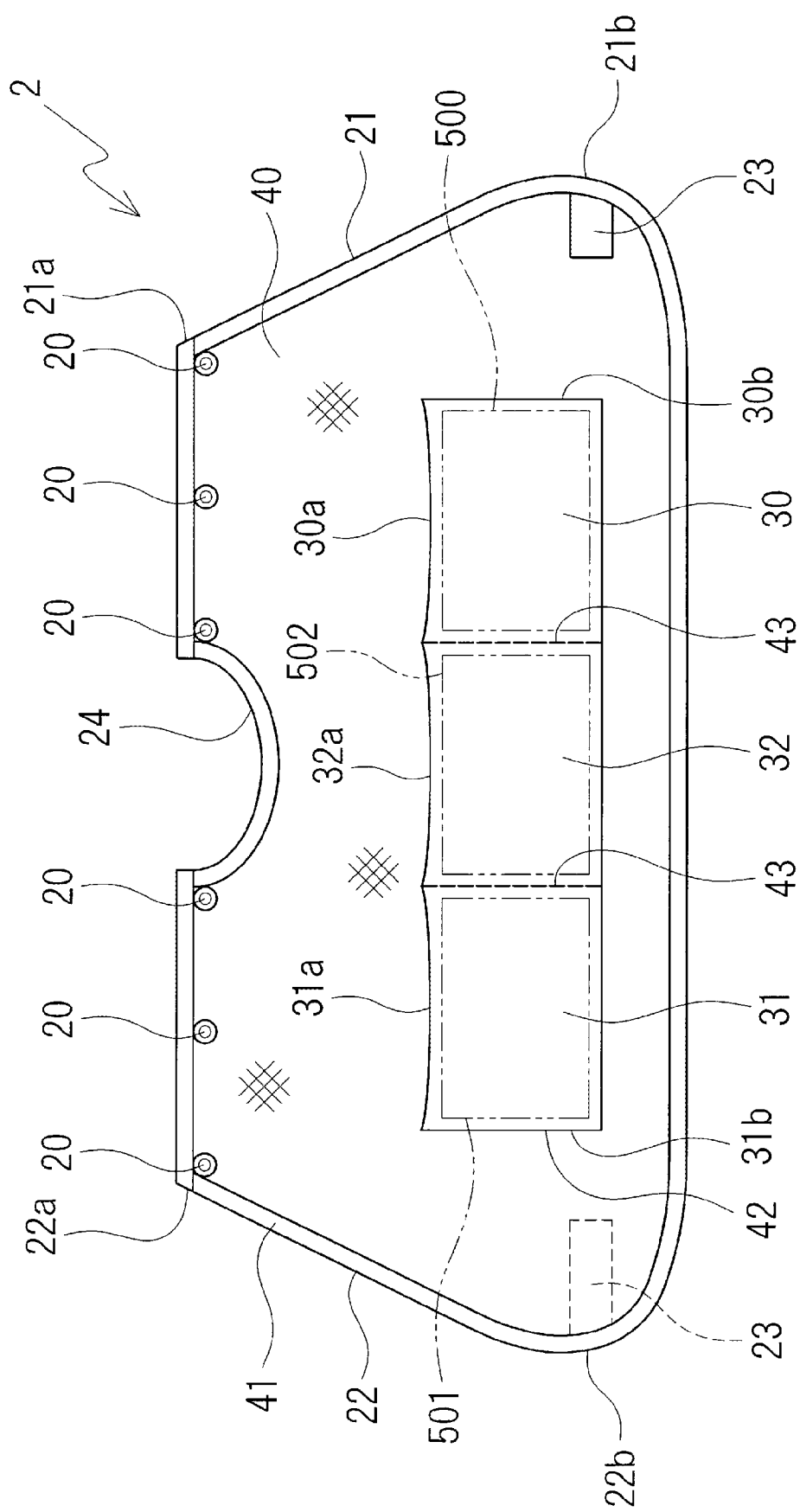
FIG. 17 is a developed view of a neck cover of a headgear according to a third embodiment of the present invention, seen from the back surface side.

Furthermore, as illustrated in FIG. 17, the first to third pockets 30, 31, and 32 may be continuously arranged side by side via one of the sewn parts 43 without a gap in the left-right direction (horizontal direction). That is, the first pocket 30 and the second pocket 31, and the second pocket 31 and the third pocket 32, that are adjacent to each other, are each partitioned by one of the sewn parts 43. The first to third pockets 30, 31, and 32 are arranged side by side with the sewn parts 43 therebetween. As illustrated in FIG. 17, the first to third pockets 30, 31, and 32 may have a horizontally elongated rectangular shape, and the first to third pockets 30, 31, and 32 may be arranged side by side in the long side direction. Each of the first to third pockets 30, 31, and 32 stores one of the first to third cooling members 500, 501, and 502 in a horizontal orientation, that is, in an orientation in which the long side direction is the left-right direction. Furthermore, the first to third pockets 30, 31, and 32 may be spaced upward from the lower end part of the neck cover 2. That is, the lower end parts of the first to third pockets 30, 31, and 32 may be spaced upward from the lower end part of the neck cover 2. The lower end part of the third piece 42 may be spaced upward from the lower end part of the neck cover 2. The lower end part of the third piece 42 may be spaced from the second piece 41.

Figure 18:
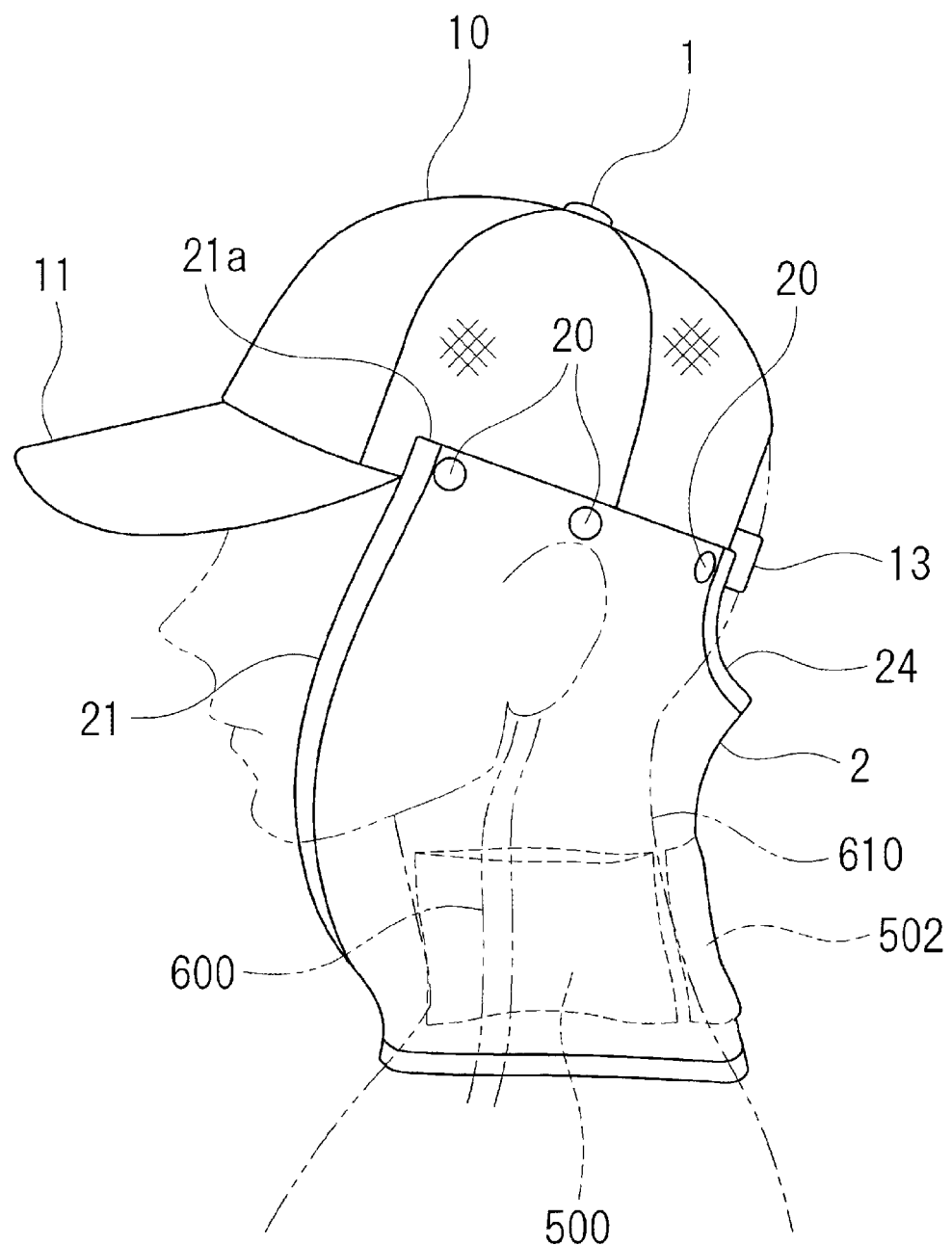
FIG. 18 is a side view illustrating a worn state of the headgear.
Figure 19:
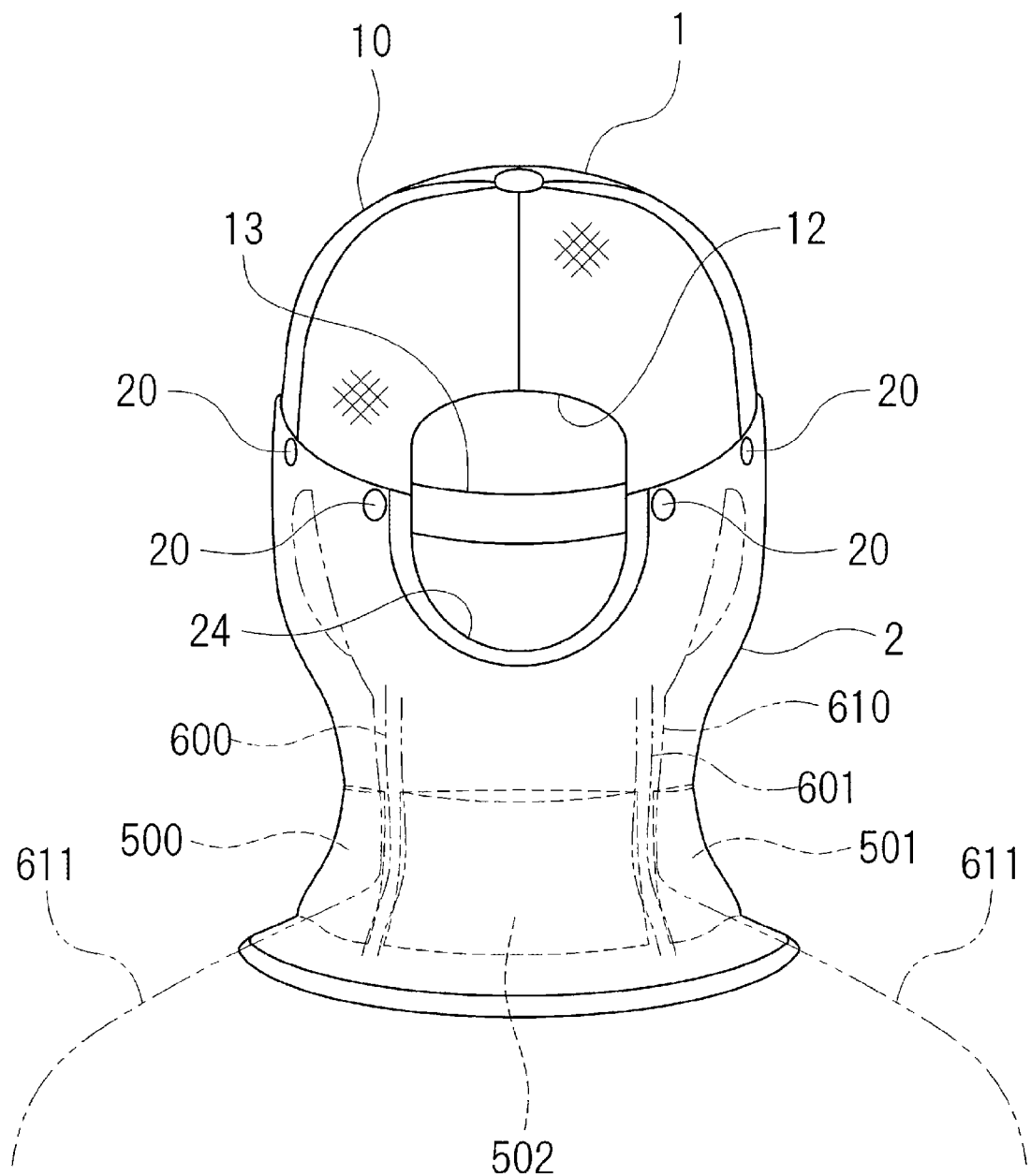
FIG. 19 is a rear view illustrating the worn state of the headgear.
Figure 20:
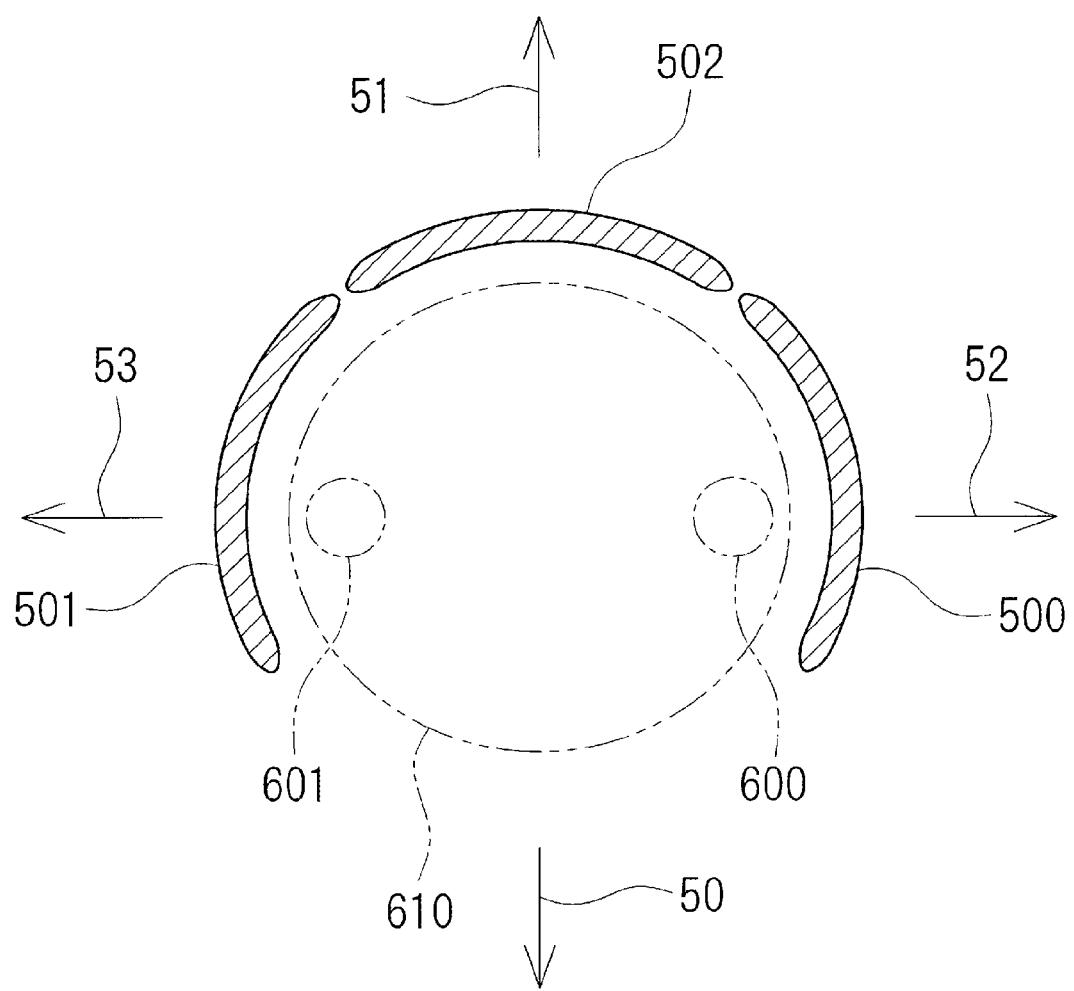
FIG. 20 is a cross-sectional view schematically illustrating, in a plane view, an arrangement of cooling members in the worn state of the headgear.
Figure 21:
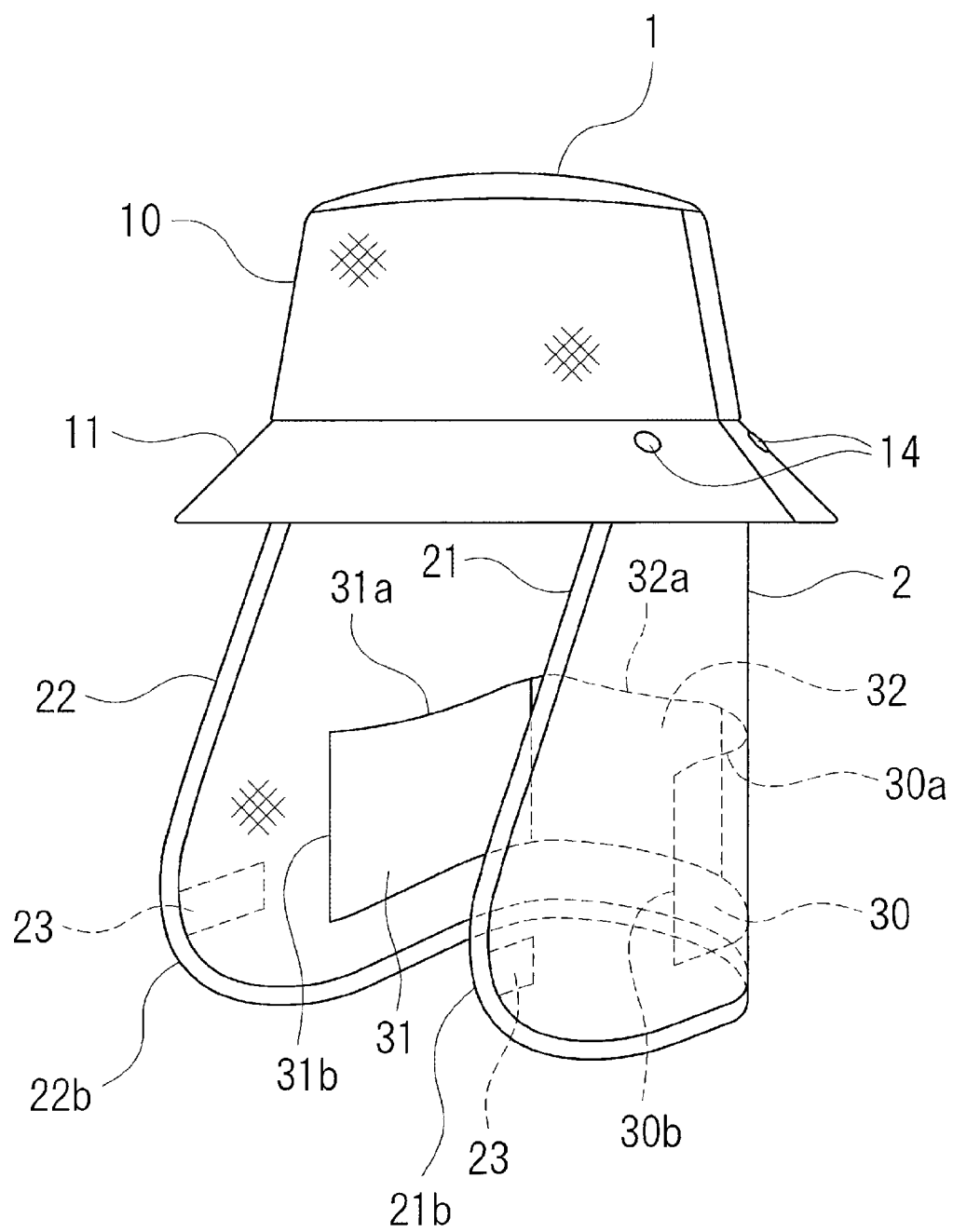
FIG. 21 is a perspective view of a headgear according to a fourth embodiment of the present invention.

FIGS. 18 and 19 illustrate a worn state of a headgear. The neck cover 2 illustrated in FIG. 17 is used for the headgear. Furthermore, FIG. 20 schematically illustrates an arrangement of the neck 610 and the first to third cooling members 500, 501, and 502. Similarly to FIG. 15, front, back, left, and right directions are also indicated by arrows in FIG. 20. In the present embodiment, a state is illustrated where the first to third cooling members 500, 501, and 502 are curved outwardly in a convex shape along the circumferential direction of the neck 610, but the first to third cooling members 500, 501, and 502 may be in a flat state without being curved. The first to third cooling members 500, 501, and 502 are oriented horizontally, and thus, it is possible to cool the neck 610 in a long section in the circumferential direction. Furthermore, the first to third cooling members 500, 501, and 502 are oriented horizontally, and thus, the first to third cooling members 500, 501, and 502 are even more easily stabilized. The first to third cooling members 500, 501, and 502 are arranged in a horizontal orientation and are arranged side by side in the left-right direction with almost no gap therebetween. Therefore, it is possible to effectively cool a wide range, that is, the entire circumference of the lower neck excluding a front portion. Furthermore, the lower end parts of the first to third pockets 30, 31, and 32 are spaced upward from the lower end part of the neck cover 2. Therefore, when the first piece 40 is made of a mesh material, a portion between the lower end parts of the first to third pockets 30, 31, and 32 and the lower end part of the neck cover 2 functions as an air-permeable part.

Fourth Embodiment

Figure 22:
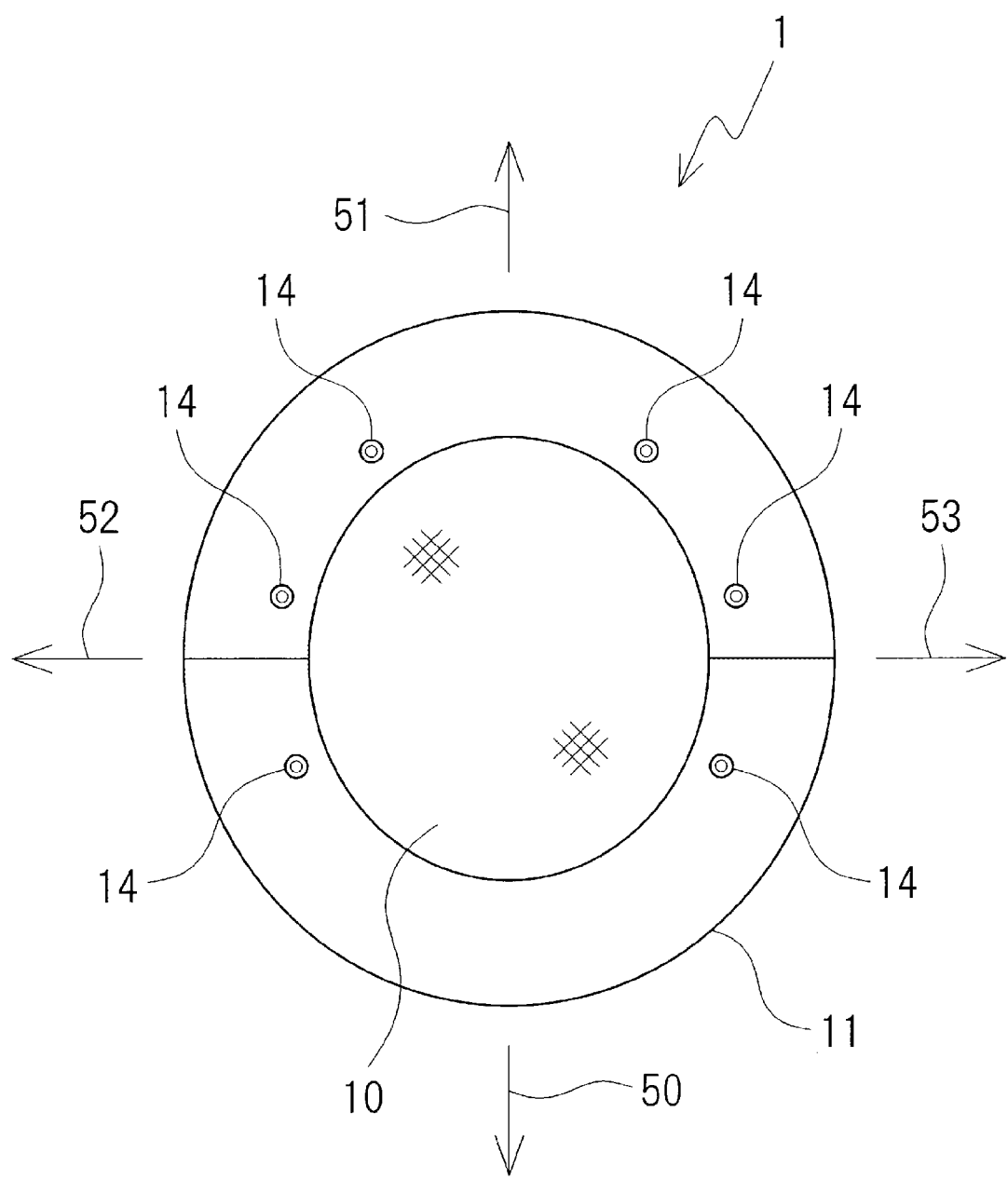
FIG. 22 is a bottom view of a headgear main body of the headgear.
Figure 23:
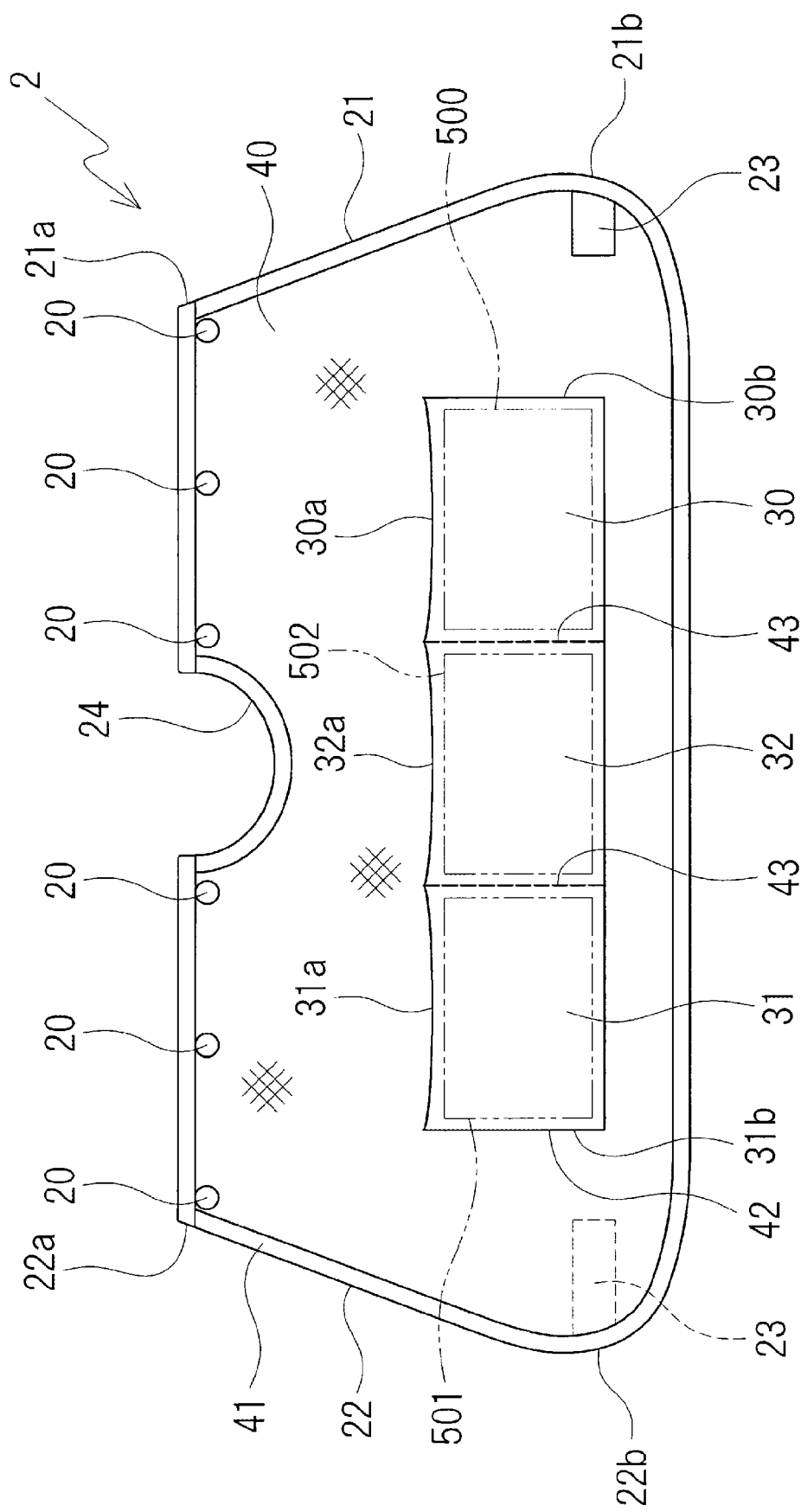
FIG. 23 is a developed view of a neck cover of the headgear, seen from a back surface side.
Figure 24:
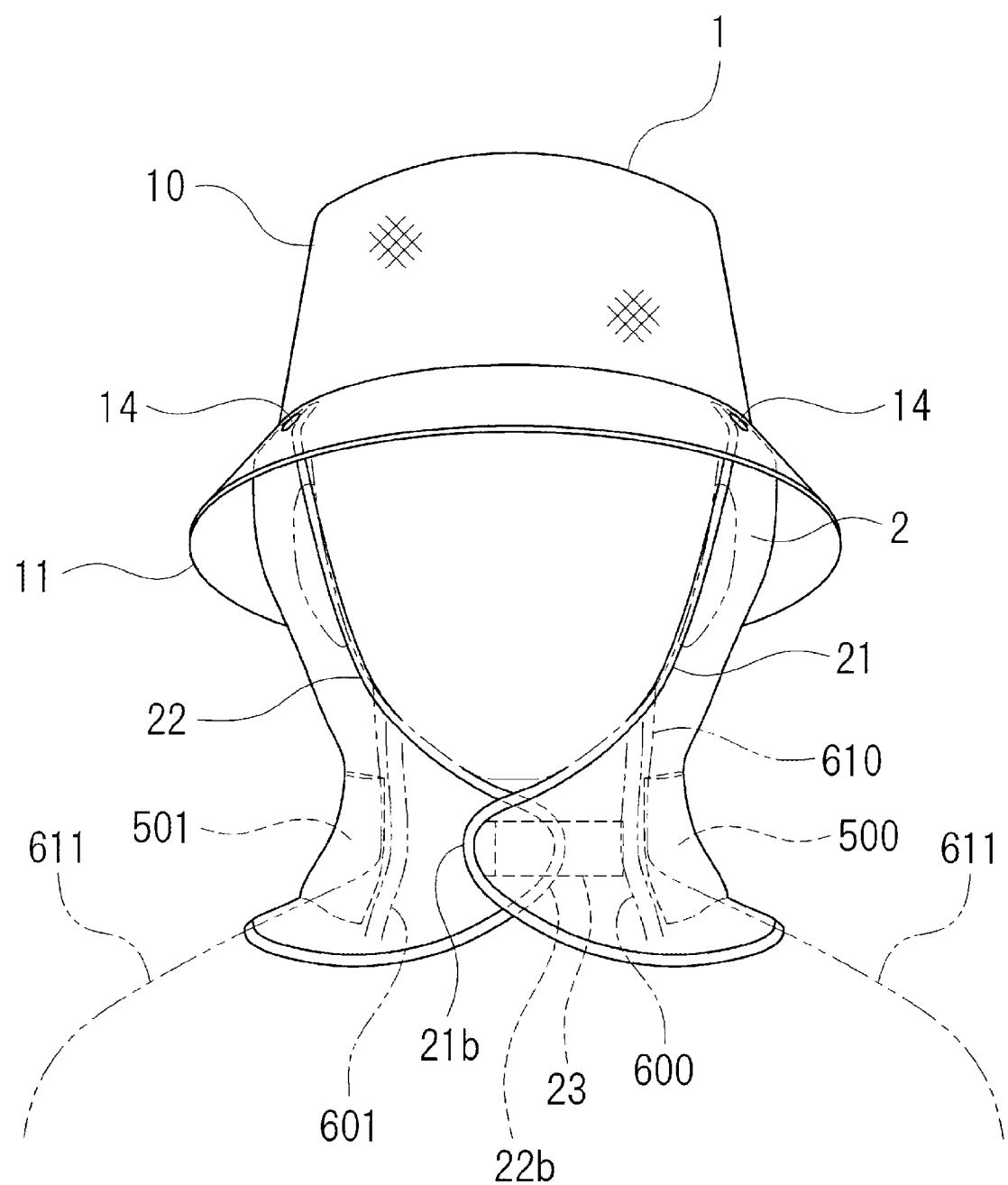
FIG. 24 is a front view illustrating a worn state of the headgear.
Figure 25:
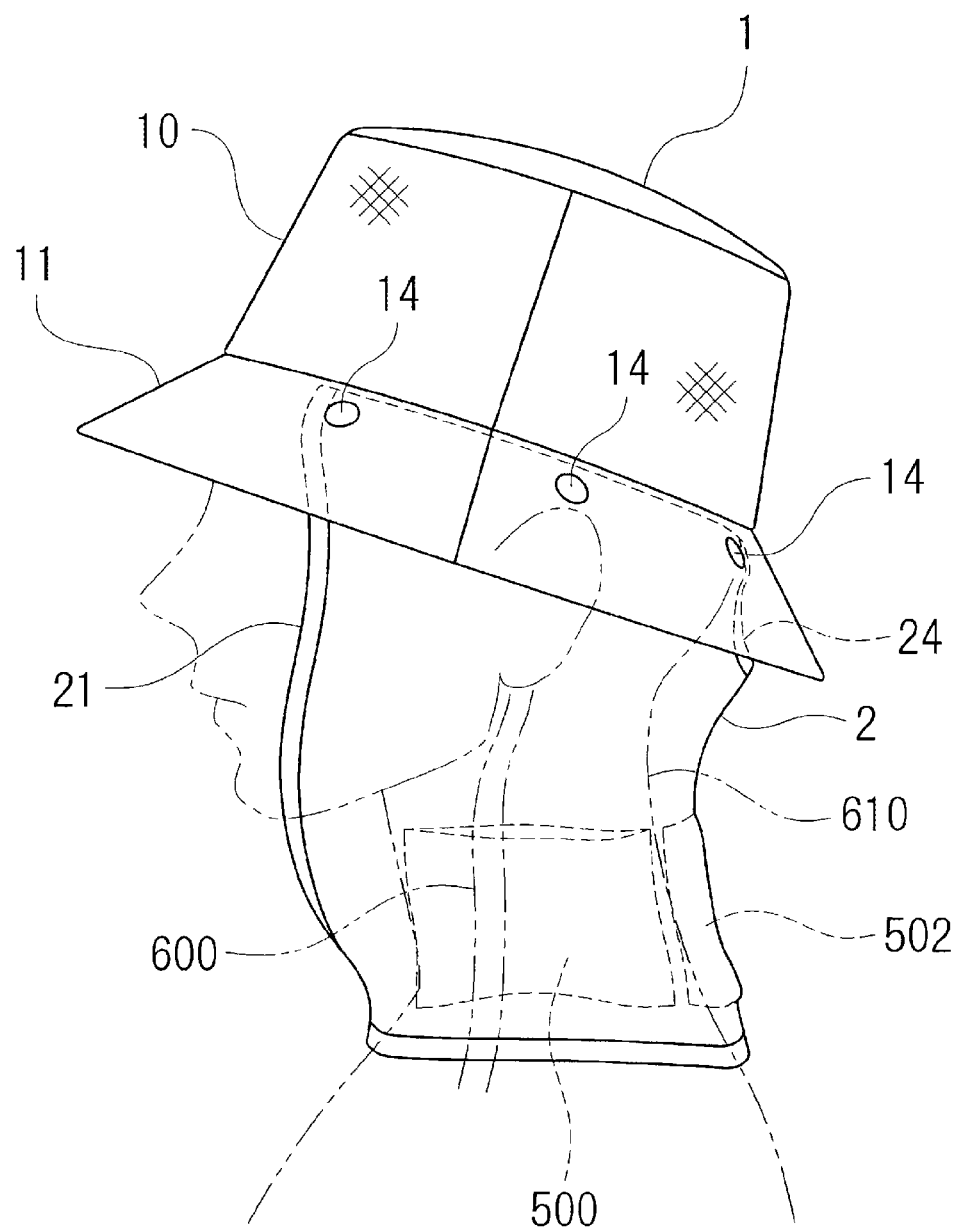
FIG. 25 is a side view illustrating the worn state of the headgear.
Figure 26:
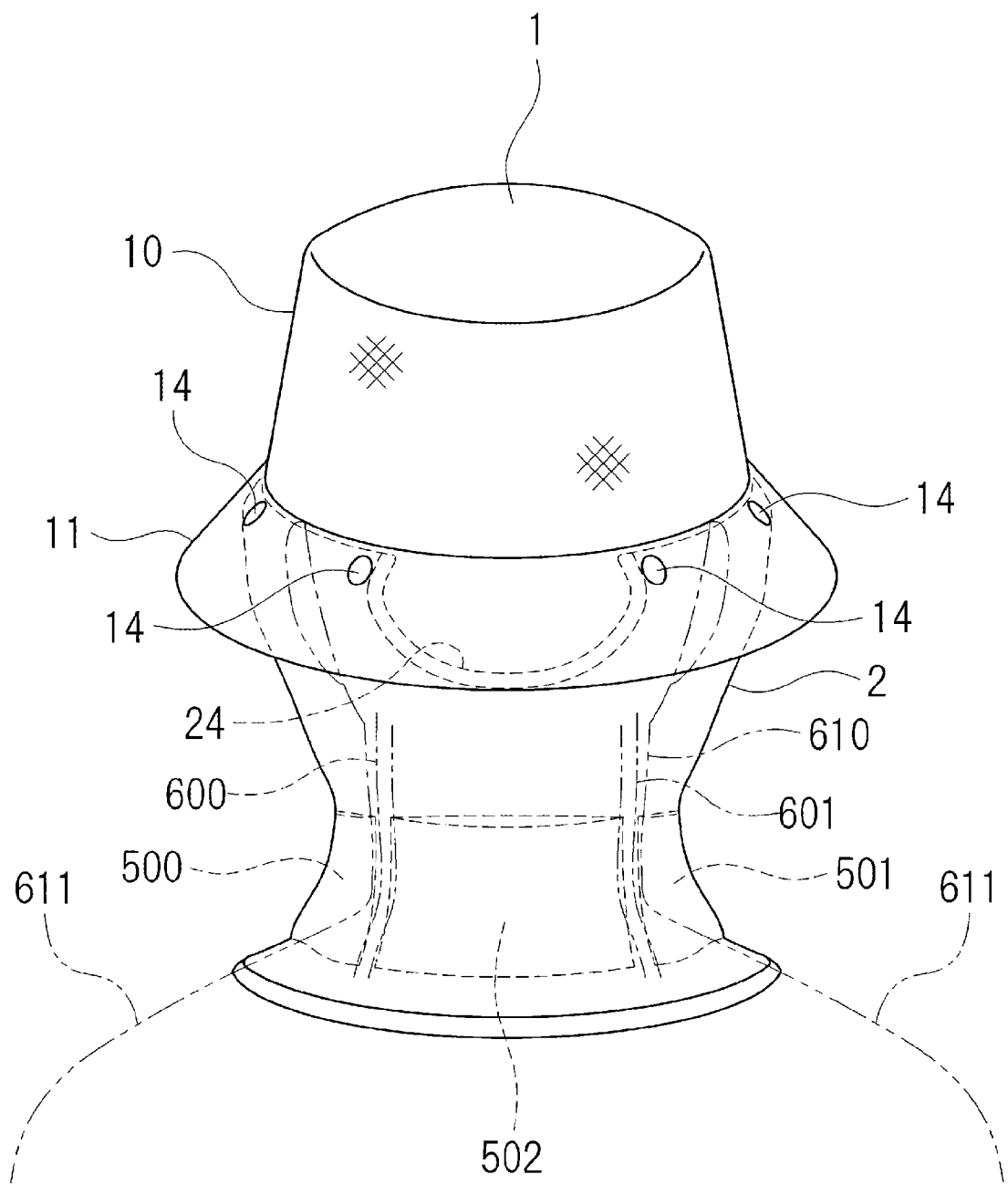
FIG. 26 is a rear view illustrating the worn state of the headgear.
Figure 27:
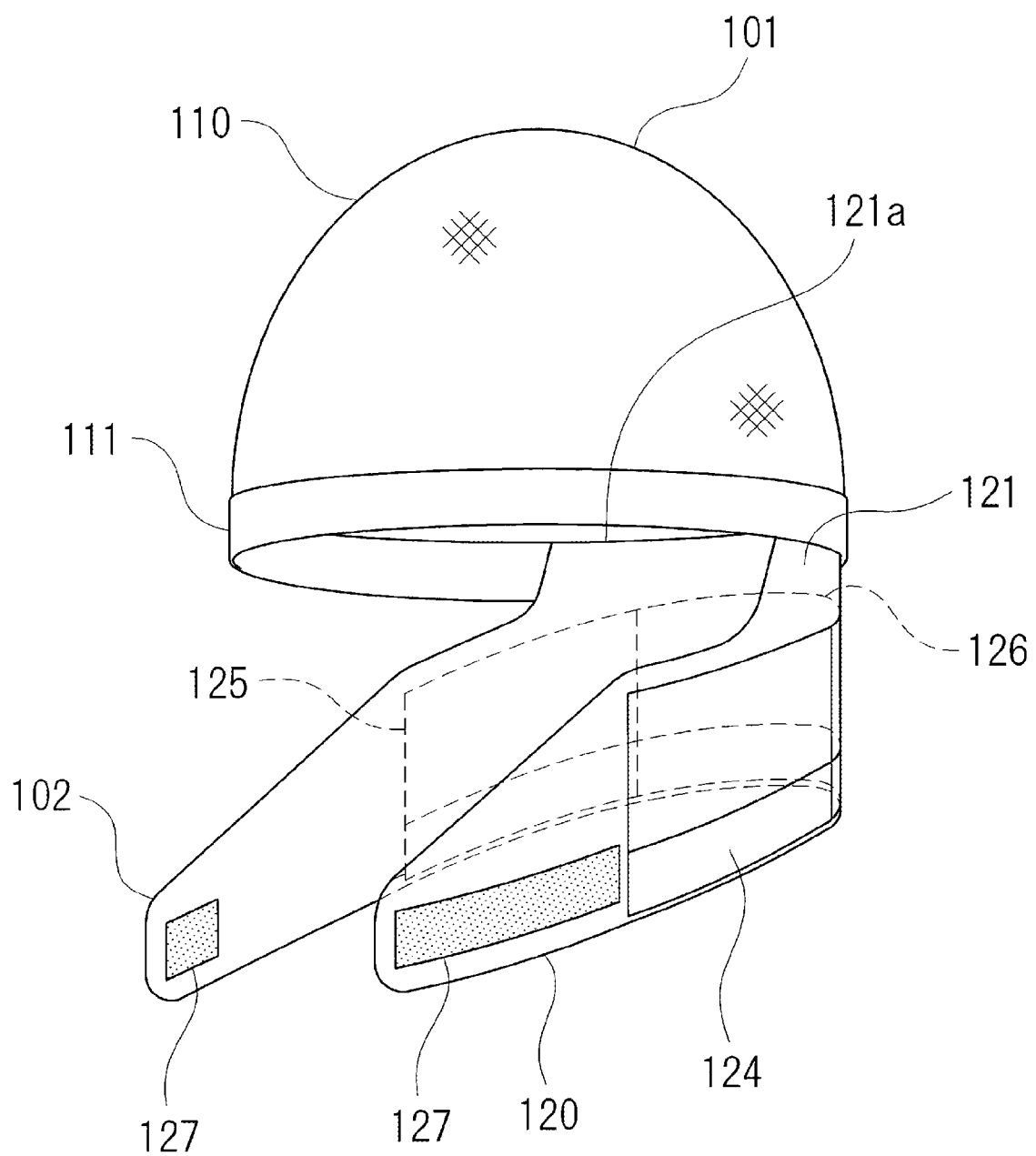
FIG. 27 is a perspective view of a headgear according to a fifth embodiment of the present invention.
Figure 28:
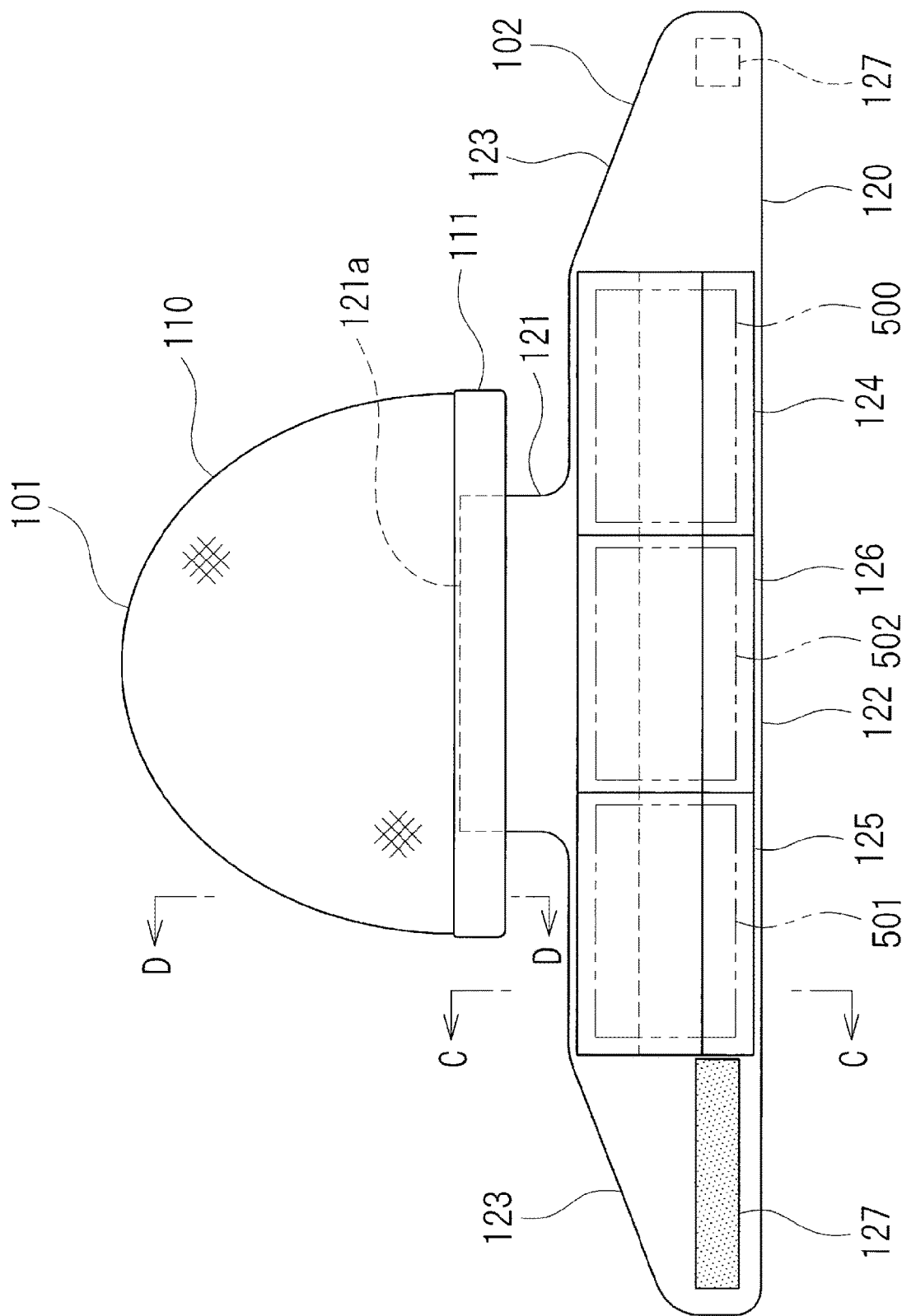
FIG. 28 is a front view of the headgear seen from the front side.

In the above-described embodiment, a case where the headgear main body 1 has the shape of a cap is illustrated as an example, but the headgear main body 1 may have the shape of a hat. A case where the headgear main body 1 has the shape of a hat is illustrated in FIGS. 21 to 26. The brim part 11 is provided along the entire circumference of the headgear main body 1. The major main body part 10 of the headgear main body 1 has a truncated cone shape. FIG. 22 illustrates a bottom view of the headgear main body 1, seen from below. The brim part 11 of the headgear main body 1 has an annular shape and extends radially outward from the lower end part of the major main body part 10. The brim part 11 has a substantially constant width over the entire circumference. The brim part 11 is provided with the dot buttons 14 for detachably attaching the neck cover 2 to the headgear main body 1. Specifically, the dot buttons 14 are arranged on a base end side (side of the major main body part 10) among the entire width of the brim part 11. Furthermore, the dot buttons 14 are provided so that the back surface (lower surface) of the brim part 11 serves as an attachment surface. FIG. 23 illustrates the neck cover 2. A basic structure of the neck cover 2 is similar to the one illustrated in FIG. 17, but the mode of attaching the dot buttons 20 is reversed with respect to the front and back. That is, the dot buttons 20 of the neck cover 2 are attached so that the front surface of the neck cover 2 serves as the attachment surface. Accordingly, the neck cover 2 is attached to the back surface (lower surface) of the brim part 11 of the headgear main body 1.

In the first to fourth embodiments, a total of three pockets are provided. However, only a pair of left and right pockets, four or more pockets, or only one pocket on the left or right side may be provided. Although a configuration is described where each of the cooling members are separately stored in one of the pockets, a large pocket having an elongated shape in the left-right direction may be used to collectively store a plurality of cooling members. Furthermore, instead of a configuration including a plurality of small cooling members, a configuration including one large cooling member (not illustrated) having an elongated shape in the left-right direction may be adopted. For example, a configuration in which the left and right carotid arteries 600 and 601 are cooled by left and right end parts of a cooling member having an elongated shape in the left-right direction may be adopted.

The pocket may be provided on the front surface side of the neck cover 2. The position of the opening part of the pocket is not limited to the upper end part of the pocket and may be provided on the left and right side edge parts of the pocket. The opening part of the pocket may be provided with opening/closing means such as a slide fastener, a hook-and-loop fastener, and a dot button for openably closing the opening part. A condensation prevention member (not illustrated) may be provided in the pocket. For example, the condensation prevention member may be provided separately from the third piece 42, and may be made of a towel cloth or a non-woven fabric, for example. It is noted that the third piece 42 may also be made of a condensation prevention member.

In addition to the cap, the shape of the headgear main body 1 may be a hat including the brim part 11 on the entire circumference, or a shape that does not include the brim part 11. For example, the brim part 11 may be removed from the headgear illustrated in FIG. 1 so that the headgear main body 1 includes only the major main body part 10. The headgear main body 1 may be a so-called inner cap that is worn inside a helmet. When a helmet is worn over the inner cap, the head is protected and the carotid arteries 600 and 601 and the like can be cooled by the cooling member of the headgear, so that the helmet and the headgear can be used at a construction site, for example. The holding part is not limited to the pocket, and the holding part may have various configurations.

Fifth Embodiment

Next, a headgear according to a fifth embodiment of the present invention will be described with reference to FIGS. 27 to 40. A headgear main body 101 of the present embodiment is an inner cap. The headgear main body 101 has a hemispherical shape. A neck cover 102 is band-shaped. The headgear main body 101 is worn on a head of a user. The neck cover 102 is wrapped around a neck of a user. Only a rear part of the lower end part of the headgear main body 101 is connected to the neck cover 102. A front part and left and right side parts of the lower end part of the headgear main body 101 are not connected to the neck cover 102. The front part and the left and right side parts of the lower end part of the headgear main body 101 are spaced upward from the neck cover 102. Portions of the lower end part of the headgear main body 101, except for the rear part, are spaced upward from the neck cover 102.

<Headgear Main Body 101>

The headgear main body 101 is open downward. The headgear main body 101 includes a major main body part 110 and a sweat stopper part 111. The major main body part 110 is a main part of the headgear main body 101. The major main body part 110 forms the greater part of the headgear main body 101. The major main body part 110 has a hemispherical shape. The sweat stopper part 111 is provided at a lower part of the major main body part 110. The sweat stopper part 111 is band-shaped. The dimensions of the sweat stopper part 111 in the up-down direction are constant. The sweat stopper part 111 has an annular shape. The sweat stopper part 111 is sewn to a lower end part, that is, to an opening edge part of the major main body part 110. The sweat stopper part 111 is folded in half in the up-down direction. The opening edge part of the major main body part 110 and the side edge parts of the sweat stopper part 111 are sewn together by a bordering piece 112.

Figure 31:
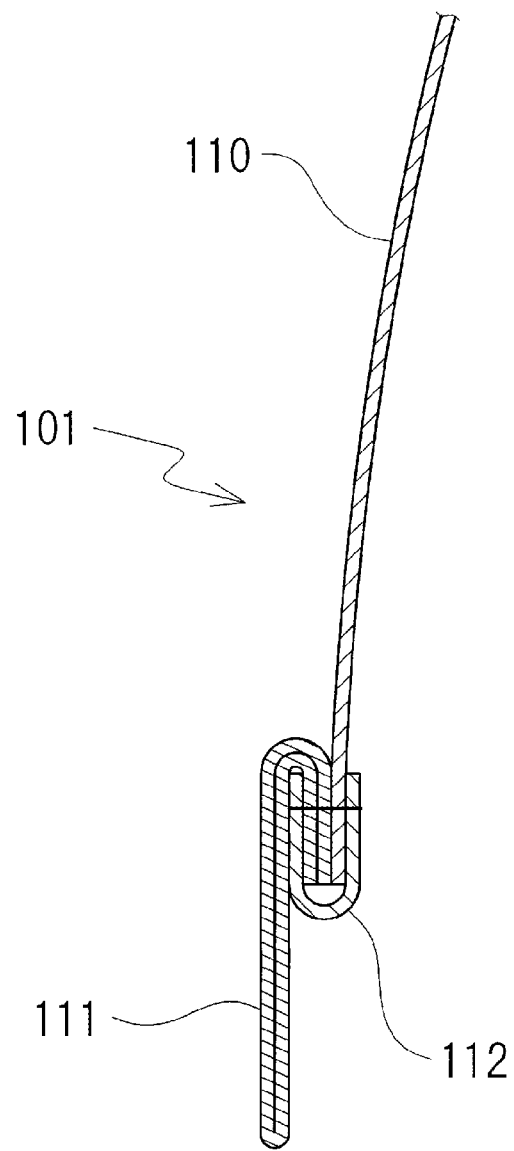
FIG. 31 is a cross-sectional view taken along line D-D in FIG. 28.
Figure 32:
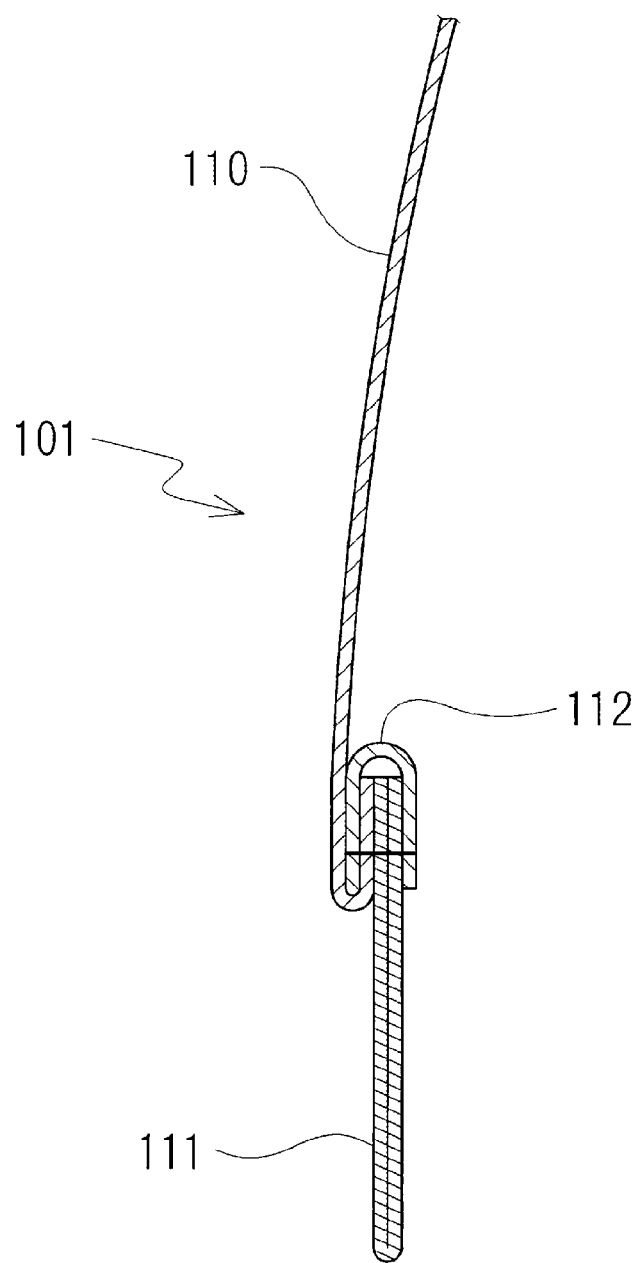
FIG. 32 is a cross-sectional view taken along line D-D in FIG. 28 and illustrates another state different from that of FIG. 31.
Figure 33:
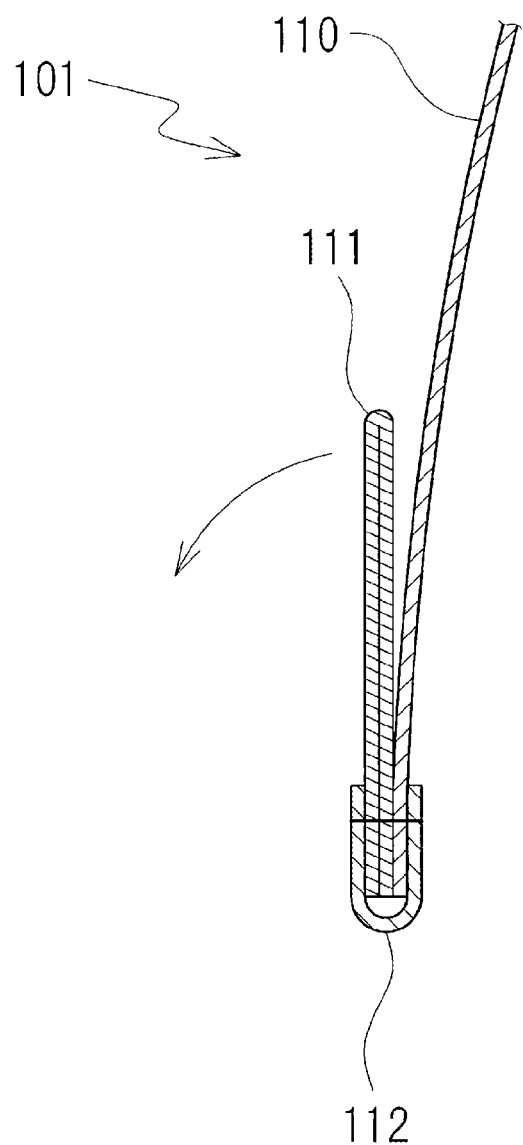
FIG. 33 is a cross-sectional view corresponding to FIG. 31 illustrating a state before a sweat stopper part of the headgear is folded downward.

FIG. 33 illustrates a state where the sweat stopper part 111 is sewn to the major main body part 110. As illustrated in FIG. 33, the sweat stopper part 111 extends upward when being sewn to the major main body part 110. During use, as indicated by an arrow in FIG. 33, the user rotates the sweat stopper part 111 downward around the bordering piece 112 as a fulcrum. FIGS. 31 and 32 illustrate usage states. As illustrated in FIG. 31, the sweat stopper part 111 is positioned on a front side of the lower end part of the major main body part 110. The sweat stopper part 111 extends upward from the bordering piece 112, and then, is folded downward and extends downward. Furthermore, as illustrated in FIG. 32, the bordering piece 112 may be positioned on a back side of the lower end part of the major main body part 110. In the mode of FIG. 32, the lower end part of the major main body part 110 is folded toward the back side of the major main body part 110. The sweat stopper part 111 extends downward from the bordering piece 112 without being folded.

The major main body part 110 is made of a first fabric. The first fabric is preferably a fabric which is excellent in air permeability. The first fabric has preferably higher air permeability than a later-described second fabric. For example, a mesh fabric is suitable as the first fabric. In particular, it is preferable to use an elastic fabric as the first fabric. The sweat stopper part 111 is made of a third fabric. The third fabric is preferably different from the first fabric. For example, a towel cloth or a quick-drying fabric is suitably used as the third fabric. It is noted that the sweat stopper part 111 may be provided only on a part of the entire circumference of the lower end part of the major main body part 110. Furthermore, the sweat stopper part 111 may overlap with the back side of the lower end part of the major main body part 110.

<Neck Cover 102>

A configuration in which the neck cover 102 and the headgear main body 101 are integrally formed may be adopted, but in the present embodiment, the neck cover 102 and the headgear main body 101 are formed as separate bodies. The neck cover 102 has a band shape extending in the left-right direction. The dimensions of the neck cover 102 in the left-right direction are set so that the neck cover 102 can surround the entire circumference of the neck of the user. The neck cover 102 includes a main neck part 120 and a protruding part 121. The main neck part 120 is a main part of the neck cover 102. The main neck part 120 includes a straight part 122 positioned at the center in the left-right direction and a pair of tapered parts 123 positioned on both the left and right sides of the main neck part 120. The straight part 122 has constant dimensions in the up-down direction. The dimensions of the tapered parts 123 in the up-down direction gradually decrease with the distance from the straight part 122.

The straight part 122 is provided with first to third pockets 124, 125, and 126. The first to third pockets 124, 125, and 126 occupy almost the entire straight part 122. The dimensions of the straight part 122 in the left-right direction are identical to the total length of the first to third pockets 124, 125, and 126 in the left-right direction. The dimensions of the straight part 122 in the up-down direction are slightly smaller than the dimensions of the first to third pockets 124, 125, and 126 in the up-down direction.

The first to third pockets 124, 125, and 126 have a horizontally elongated rectangular shape. The first to third pockets 124, 125, and 126 have storage spaces that are independent of each other. The first to third cooling members 500, 501, and 502 are respectively stored in the first to third pockets 124, 125, and 126. The first to third cooling members 500, 501, and 502 may be of various types. For example, the first to third cooling members 500, 501, and 502 are an ice pack or ice. The ice pack is stored in the first to third pockets 124, 125, and 126 so that the long side direction of the ice pack is the left-right direction. That is, an ice pack having a rectangular shape is stored in the first to third pockets 124, 125, and 126 in a horizontal orientation.

Figure 30:
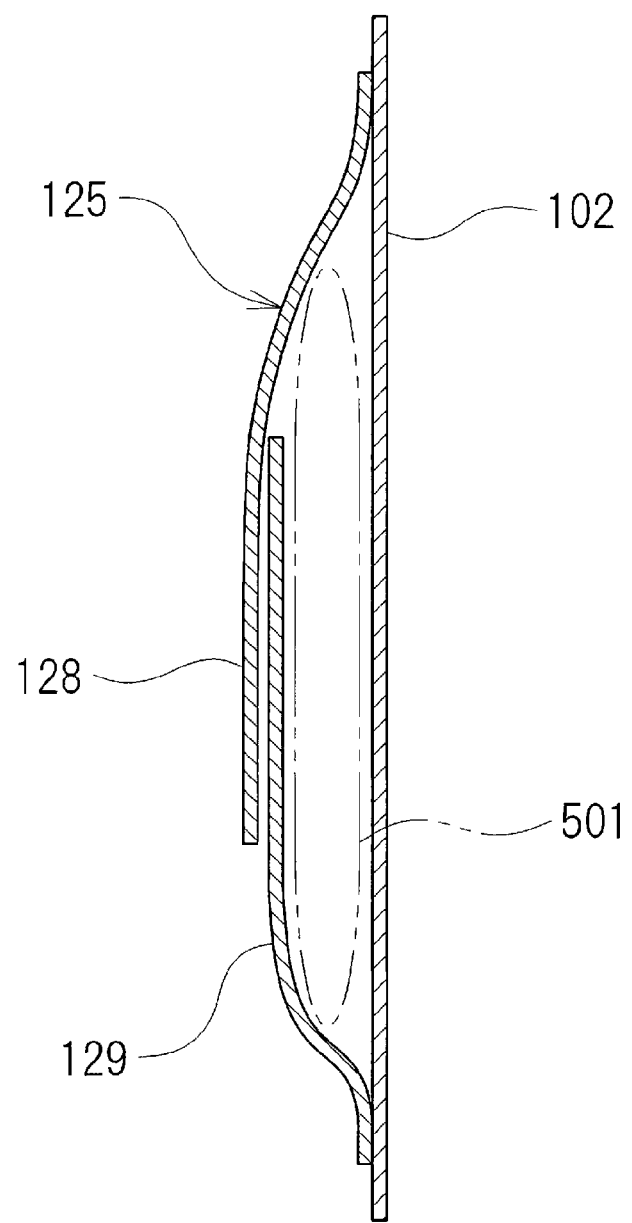
FIG. 30 is a cross-sectional view taken along line C-C in FIG. 28.

The first to third pockets 124, 125, and 126 may have various configurations. In the present embodiment, the first to third pockets 124, 125, and 126 are provided on a front surface (outer surface) of the straight part 122. However, the first to third pockets 124, 125, and 126 may be provided on a back surface (inner surface) of the straight part 122. As illustrated in FIG. 30, the first to third pockets 124, 125, and 126 are composed of an upper piece 128 and a lower piece 129. The upper piece 128 and the lower piece 129 are sewn to an outer surface of the neck cover 102. A lower part of the upper piece 128 overlaps the front side of an upper part of the lower piece 129. Opening parts of the first to third pockets 124, 125, and 126 are formed between the lower part of the upper piece 128 and the upper part of the lower piece 129. The first to third cooling members 500, 501, and 502 are introduced and removed through the opening parts of the first to third pockets 124, 125, and 126.

Upper end parts of the tapered parts 123 are inclined. Lower end parts of the tapered parts 123 are arranged in line with a lower end part of the straight part 122. Hook-and-loop fasteners 127 are provided on the tapered parts 123. The hook-and-loop fasteners 127 are coupling parts that detachably couple a left end part and a right end part of the neck cover 102. The left end part and the right end part of the neck cover 102 are coupled by the hook-and-loop fasteners 127 in an overlapping manner.

The protruding part 121 protrudes upward from a center part of the main neck part 120 in the left-right direction. The protruding part 121 protrudes upward from an upper end part of the straight part 122 of the main neck part 120. An upper end part 121a of the protruding part 121 is sewn to the headgear main body 101. Specifically, as illustrated in FIGS. 34 to 37, the upper end part 121a of the protruding part 121, the opening edge part of the major main body part 110, and the side edge parts of the sweat stopper part 111 are sewn together by the bordering piece 112.

Figure 34:
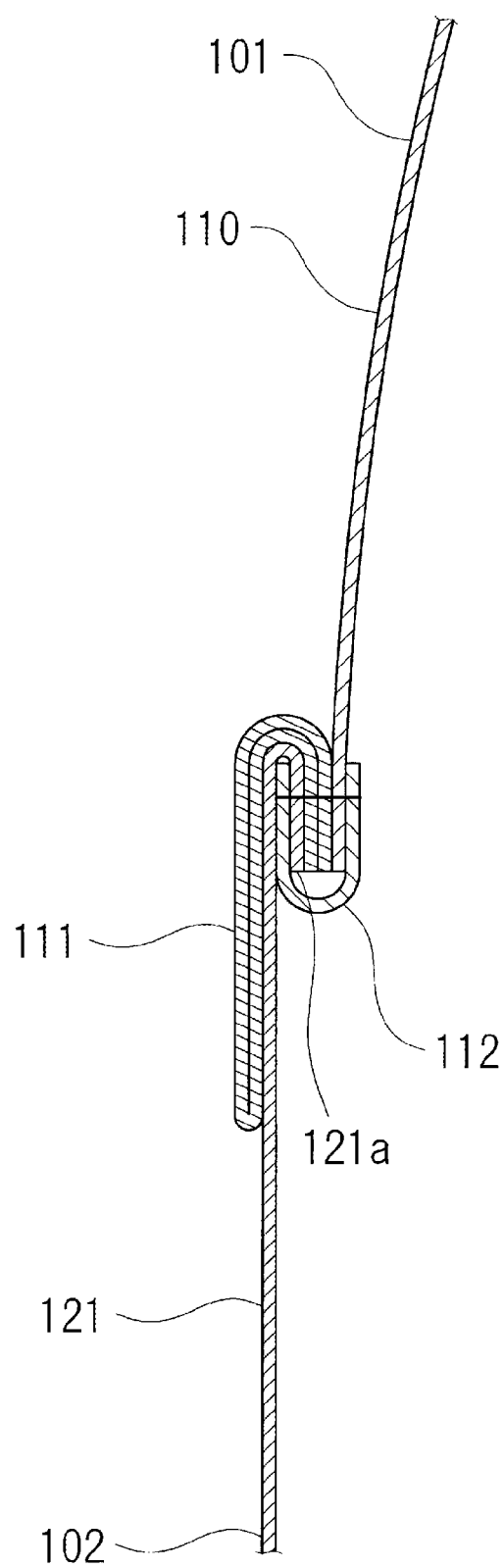
FIG. 34 is a cross-sectional view taken along line E-E in FIG. 29.
Figure 35:
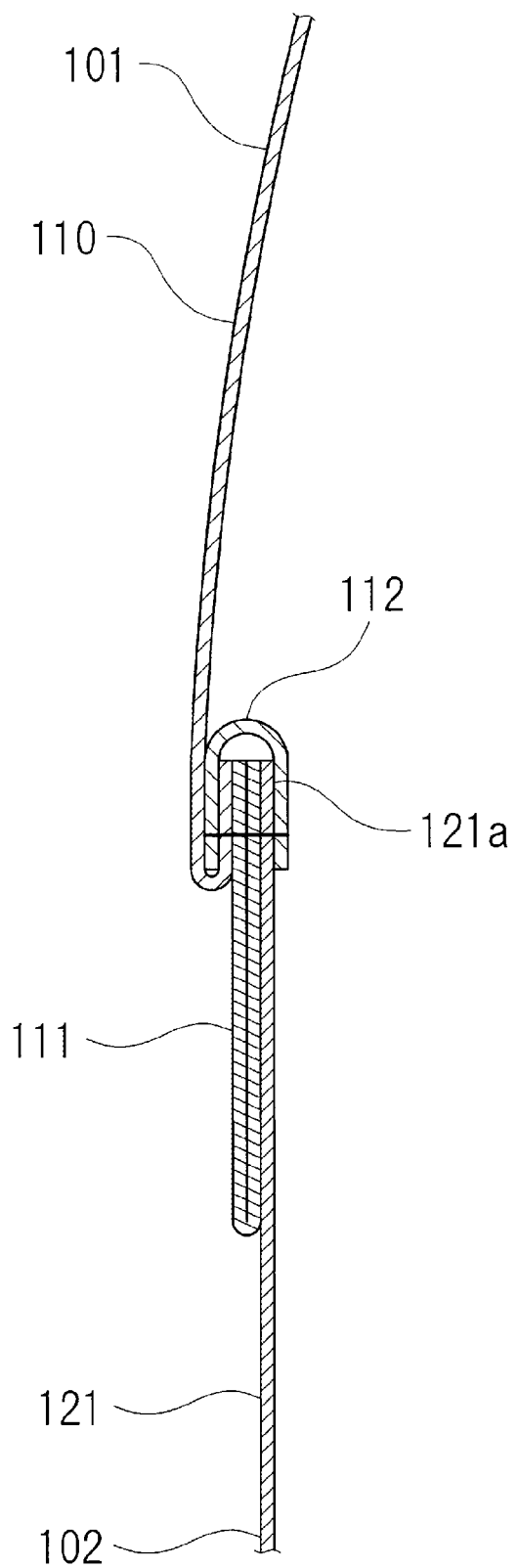
FIG. 35 is a cross-sectional view taken along line E-E in FIG. 29 and illustrates another state different from that of FIG. 34.
Figure 36:
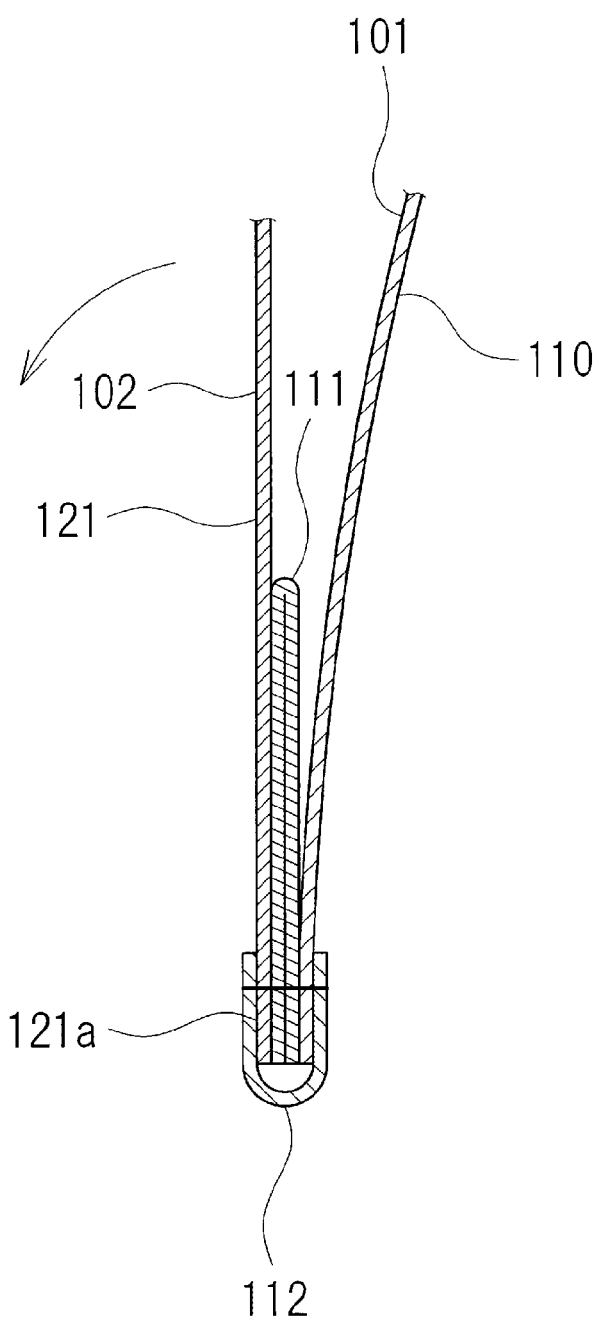
FIG. 36 is a cross-sectional view corresponding to FIG. 34 illustrating a state before the neck cover of the headgear is folded downward.
Figure 37:
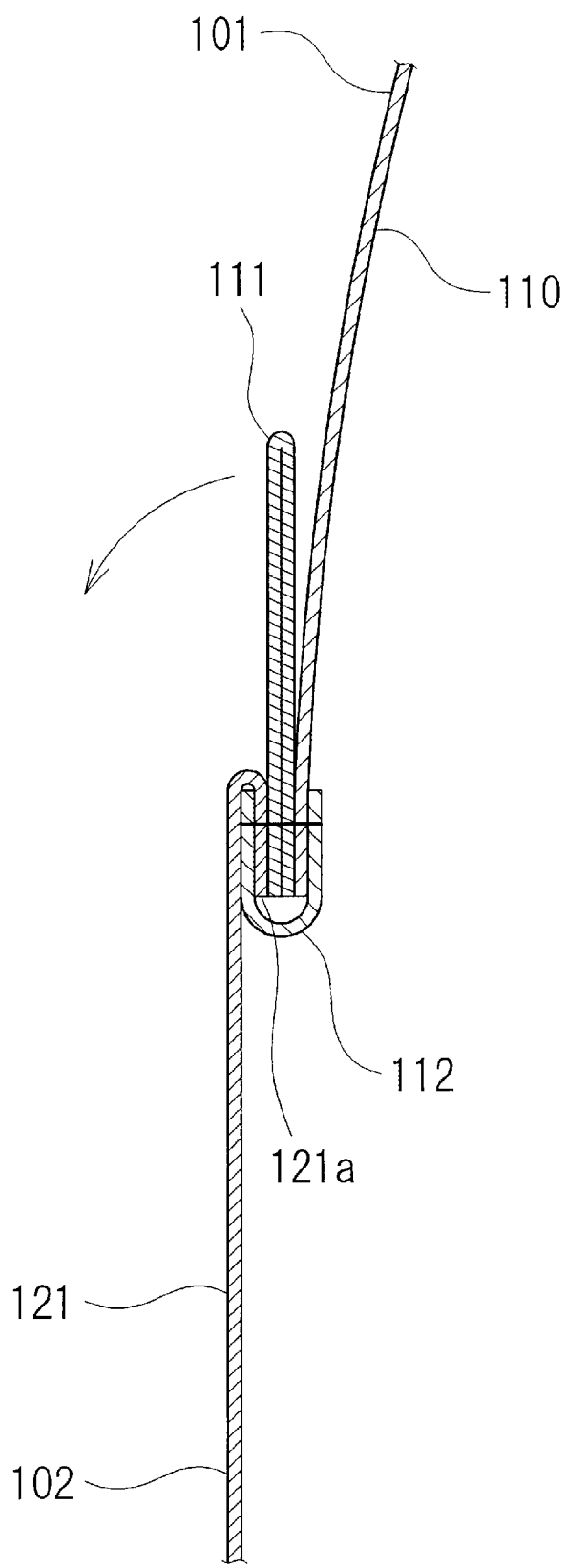
FIG. 37 is a cross-sectional view corresponding to FIG. 34 illustrating a state before the sweat stopper part of the headgear is folded downward.

FIG. 36 illustrates a state where the sweat stopper part 111, the major main body part 110, and the protruding part 121 are sewn together. That is, FIG. 36 illustrates a state where the sweat stopper part 111, the major main body part 110, and the neck cover 102 are sewn together. As illustrated in FIG. 36, the protruding part 121 and the sweat stopper part 111 extend upward when the sweat stopper part 111, the major main body part 110, and the neck cover 102 are sewn together. After that, as indicated by an arrow in FIG. 36, the protruding part 121 is rotated downward around the bordering piece 112 as a fulcrum. The protruding part 121 extends upward from the bordering piece 112, and then, is folded downward and extends downward. FIG. 37 illustrates a state where the protruding part 121 is rotated downward. During use, as indicated by an arrow in FIG. 37, the user rotates the sweat stopper part 111 downward around the bordering piece 112 as a fulcrum. FIGS. 34 and 35 illustrate usage states. As illustrated in FIG. 34, the sweat stopper part 111 is positioned on the front side of the lower end part of the major main body part 110 and in front of the protruding part 121. The sweat stopper part 111 overlaps the front side of the protruding part 121. The sweat stopper part 111 extends upward from the bordering piece 112, and then, is folded downward and extends downward. Furthermore, as illustrated in FIG. 35, the bordering piece 112 may be positioned on the back side of the lower end part of the major main body part 110. In the mode of FIG. 35, the lower end part of the major main body part 110 is folded toward the back side of the major main body part 110. The sweat stopper part 111 and the protruding part 121 extend downward from the bordering piece 112 without being folded.

Figure 29:
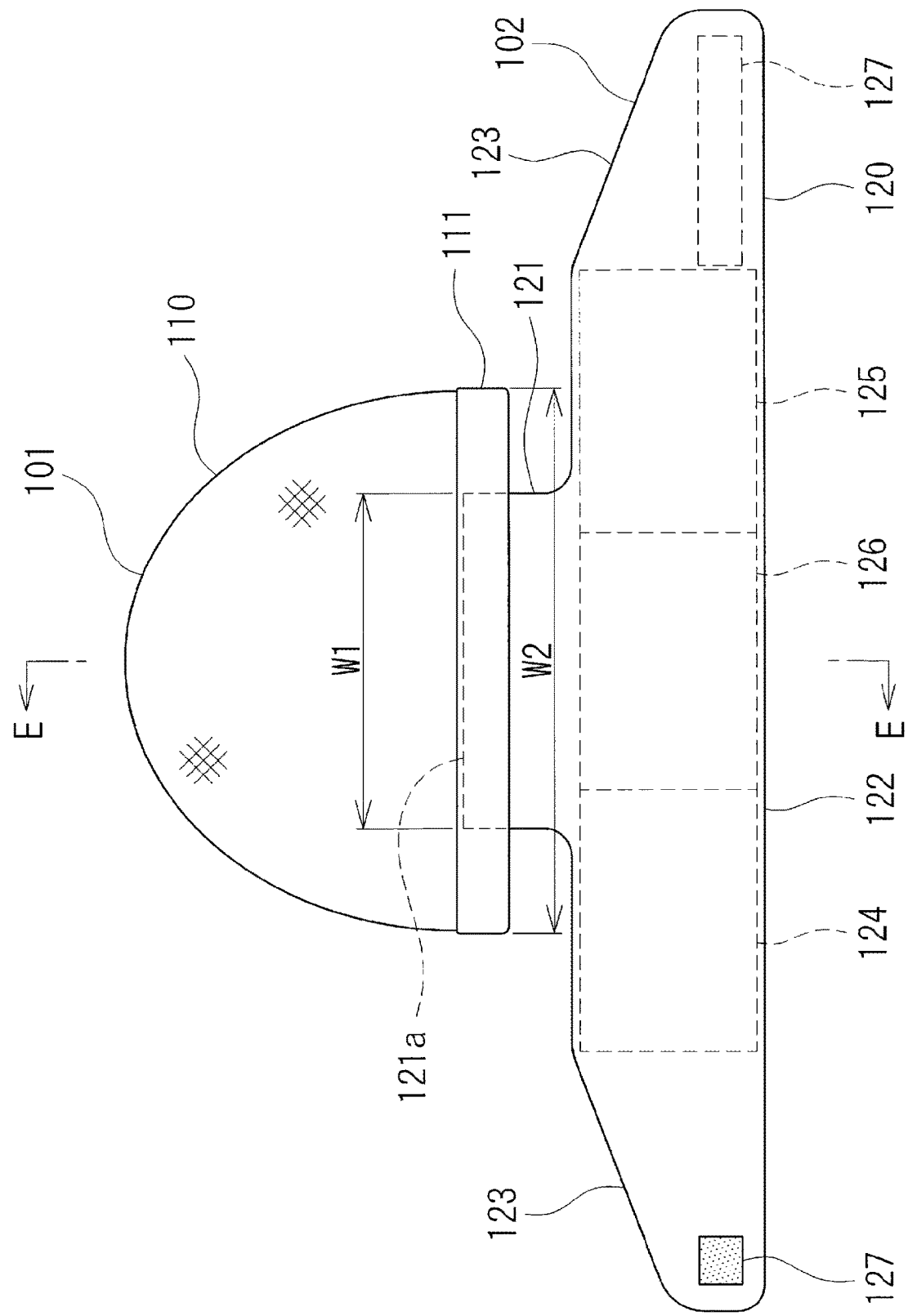
FIG. 29 is a rear view of the headgear seen from the rear side.

The protruding part 121 is connected to the rear part of the headgear main body 101. The dimensions of the protruding part 121 in the up-down direction correspond to the amount of protrusion of the protruding part 121 from the main neck part 120. Increase in the amount of protrusion of the protruding part 121 results in increase in a distance by which the headgear main body 101 and the main neck part 120 are separated. The upper end part 121a of the protruding part 121 is sewn to the rear part of the headgear main body 101. The upper end part 121a of the protruding part 121 is a connection part in which the neck cover 102 is connected to the headgear main body 101. As illustrated in FIG. 29, a length W1 of the upper end part 121a of the protruding part 121 in the left-right direction is shorter than a diameter W2 of the headgear main body 101. The diameter W2 of the headgear main body 101 is a diameter of the opening part of the headgear main body 101. The length W1 of the upper end part 121a of the protruding part 121 in the left-right direction is a length in the left-right direction of a portion where the headgear main body 101 and the neck cover 102 are connected. As described above, when the length W1 of the upper end part 121a of the protruding part 121 in the left-right direction is shorter than the diameter W2 of the headgear main body 101, it is possible to easily sew together the protruding part 121 and the headgear main body 101.

It is preferable that the second fabric forming the neck cover 102 is different from the first fabric. The second fabric is preferably thinner than the first fabric. It is preferable to use an elastic fabric as the second fabric. It is preferable that the second fabric has higher elasticity than the first fabric. A material imparting a cooling sensation is suitable to be used as the second fabric. It is noted that the upper piece 128 and the lower piece 129 are preferably formed from the same fabric as the second fabric, but may also be formed from a different fabric. The main neck part 120 and the protruding part 121 are formed from a single piece of the second fabric, but may also be formed from different fabrics.

<Worn State>

Figure 38:
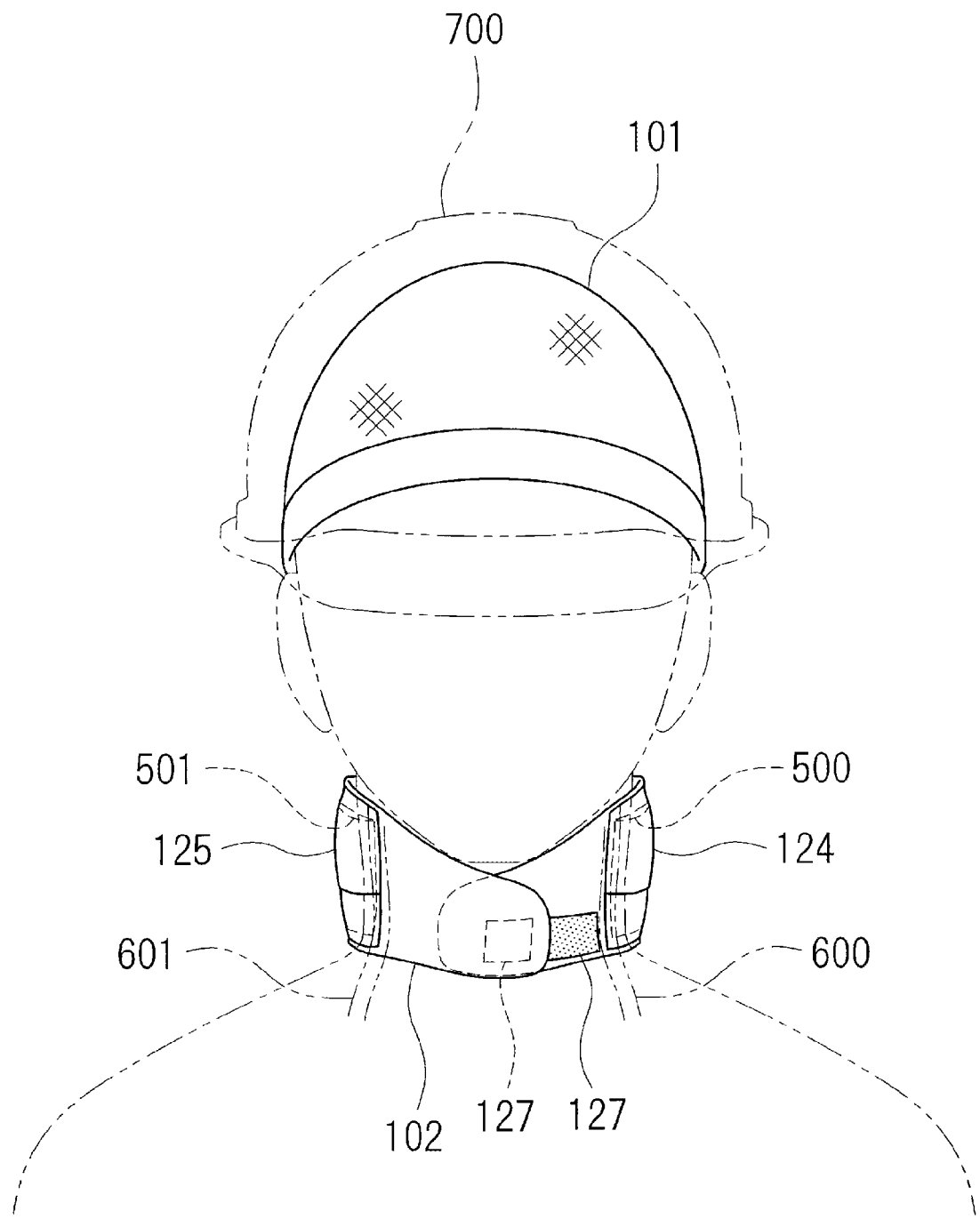
FIG. 38 is a front view illustrating a worn state of the headgear.
Figure 39:
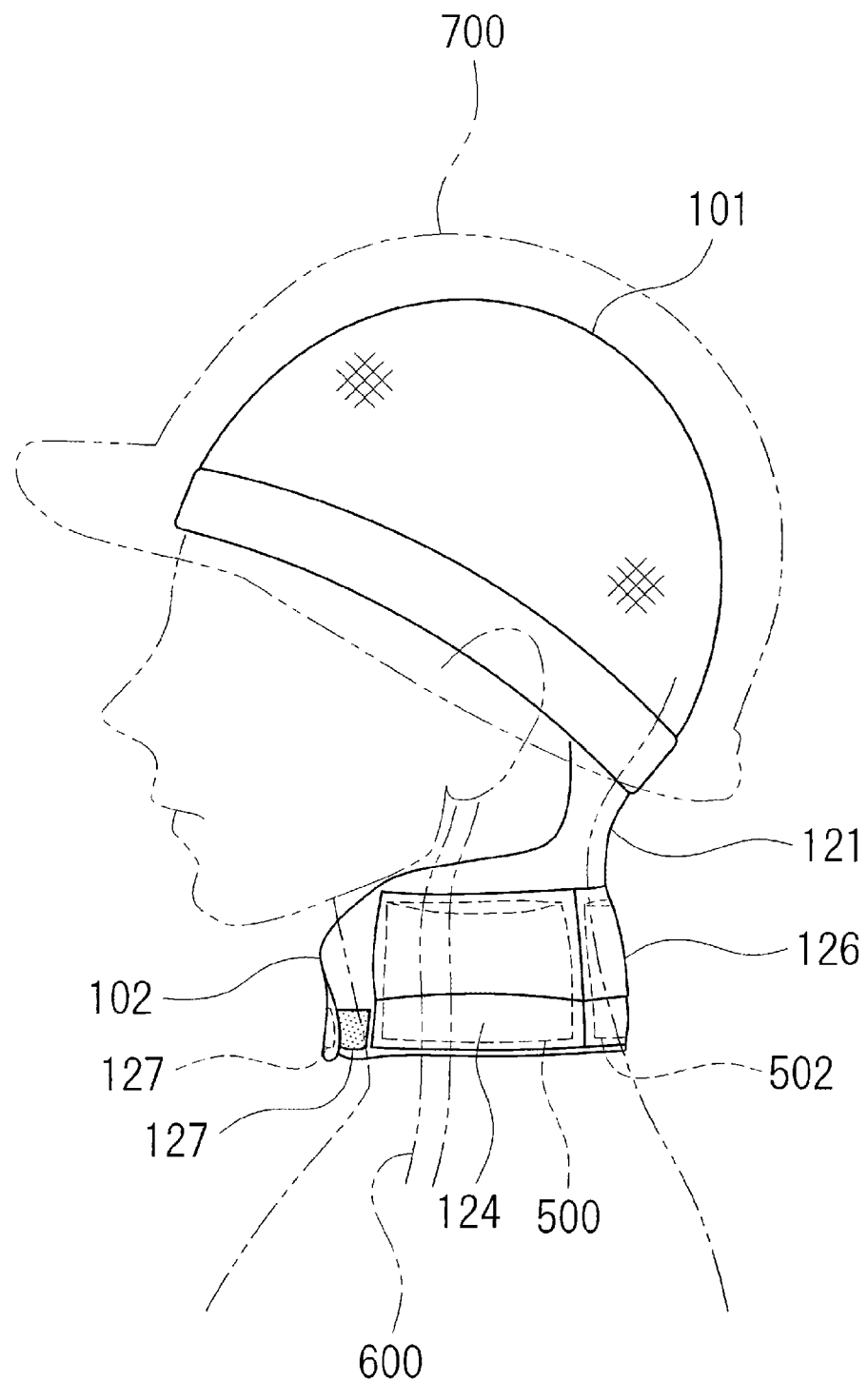
FIG. 39 is a side view illustrating the worn state of the headgear.
Figure 40:
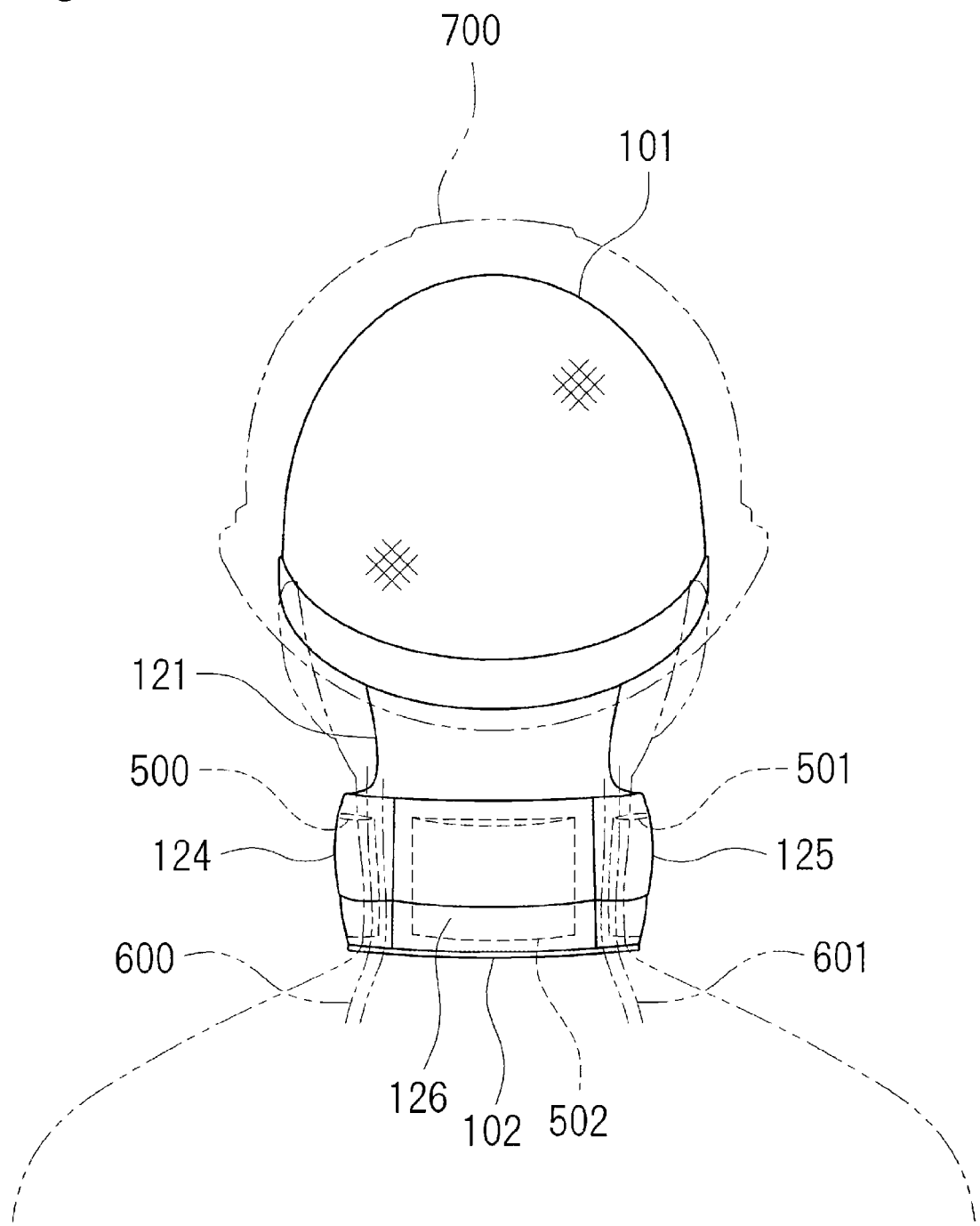
FIG. 40 is a rear view illustrating the worn state of the headgear.
Figure 41:
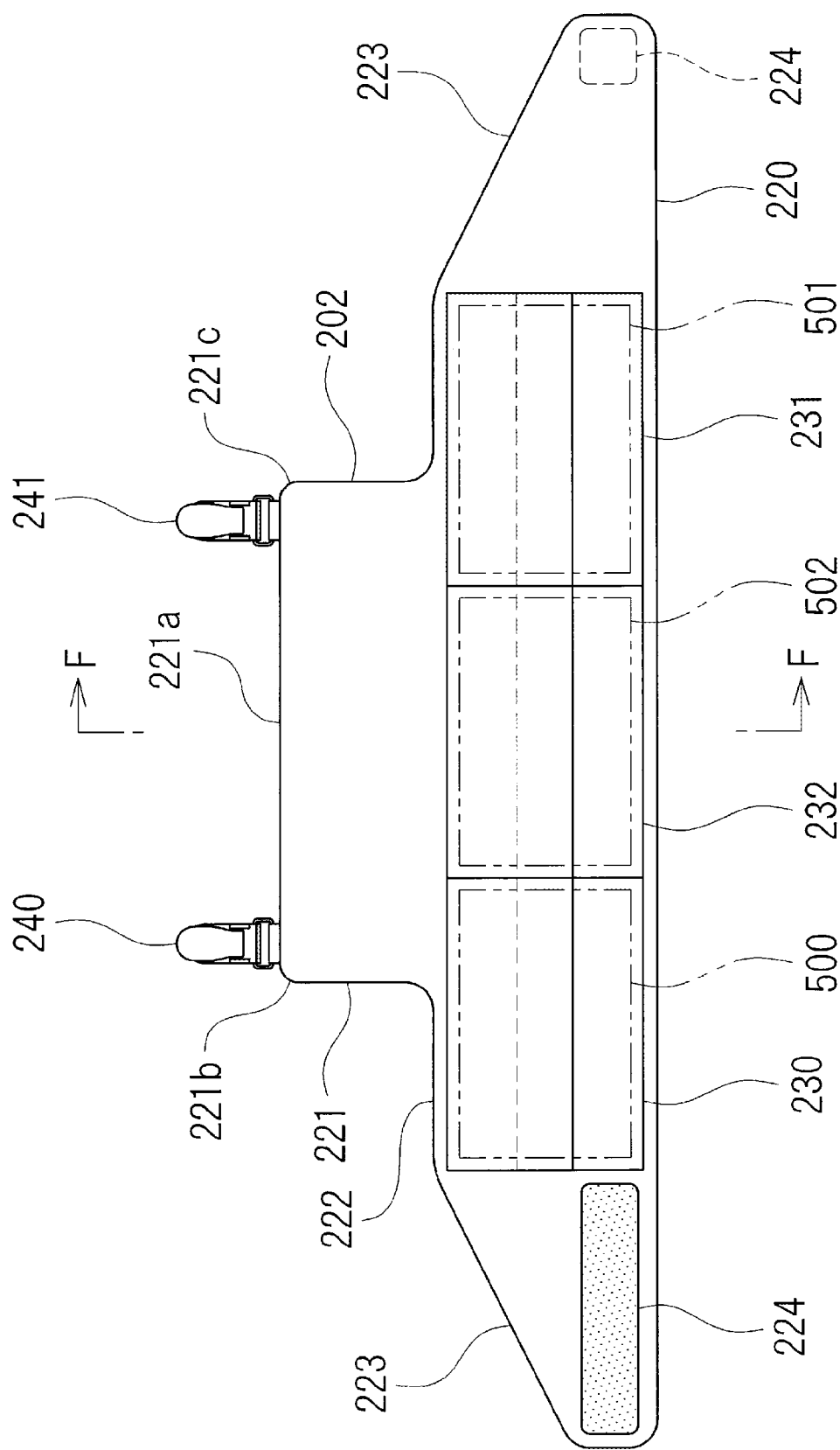
FIG. 41 is a front view of a neck cover of a headgear according to a sixth embodiment of the present invention, seen from a front surface side.
Figure 42:
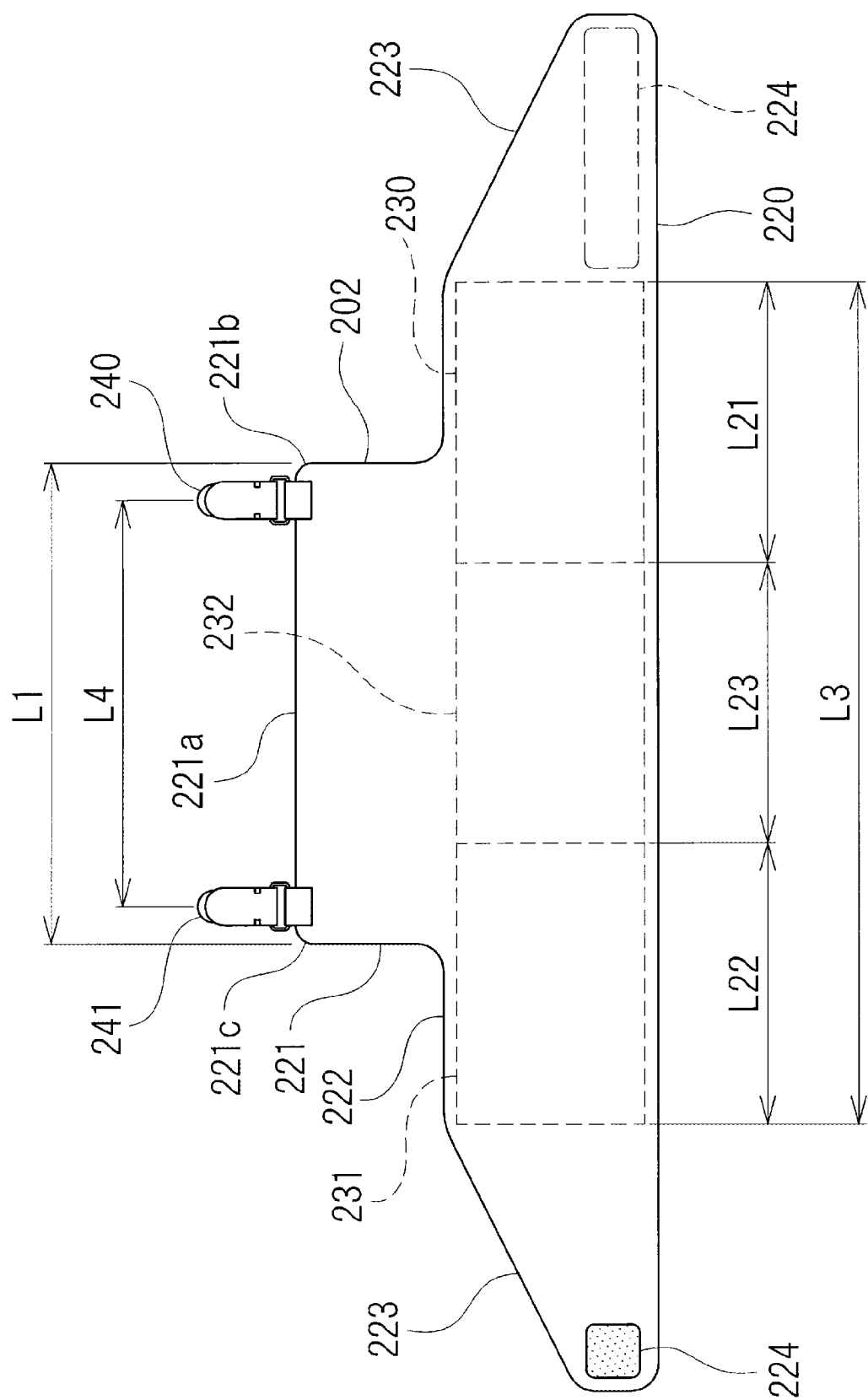
FIG. 42 is a rear view of the neck cover, seen from a back surface side.

FIGS. 38 to 40 illustrate a worn state of the headgear. A user wears the headgear main body 101 and further wears a helmet 700 over the headgear main body 101. Before wearing the headgear main body 101, the user respectively places the first to third cooling members 500, 501, and 502 in advance in the first to third pockets 124, 125, and 126. The user puts the headgear main body 101 on a head of the user. In the worn state, the headgear main body 101 is inclined backward with the rear side of the headgear main body 101 being the lower side. The user wraps the neck cover 102 around the neck. The neck cover 102 is positioned below the ears. The user uses the hook-and-loop fasteners 127 to couple the left end part and the right end part of the neck cover 102. The left end part and the right end part of the neck cover 102 are coupled at a position in front of the neck. A coupling portion of the neck cover 102 is positioned below the chin. When the left end part and the right end part of the neck cover 102 are coupled, the neck cover 102 takes an annular shape, and the neck cover 102 surrounds the neck. The band-like shape of the neck cover 102 allows the user to easily wrap the neck cover 102 around the neck.

When the neck cover 102 is attached to the neck, the first cooling member 500 is positioned on a left side of the neck, the second cooling member 501 is positioned on a right side of the neck, and the third cooling member 502 is positioned on a rear side of the neck. The band-like shape of the neck cover 102 allows the first to third cooling members 500, 501, and 502 to be in close contact with the neck with the neck cover 102 therebetween. The first cooling member 500 faces the left carotid artery 600, and the second cooling member 501 faces the right carotid artery 601.

As described above, it is possible to directly cool the left and right carotid arteries 600 and 601 by the first and second cooling members 500 and 501 stored in the first and second pockets 124 and 125. The carotid arteries 600 and 601 are blood vessels leading from the heart to the brain. Therefore, heatstroke can be effectively prevented by cooling the carotid arteries 600 and 601 with the first and second cooling members 500 and 501. The first and second cooling members 500 and 501 are symmetrically positioned on the left side and the right side of the neck, and thus, the left-right balance of the headgear is excellent. Therefore, the neck cover 102 is not easily displaced, and the burden on the user is small. Furthermore, the rear part of the neck can be cooled by the third cooling member 502. The first to third cooling members 500, 501, and 502 having a rectangular shape are stored in a horizontal orientation in the first to third pockets 124, 125, and 126, and thus, the user experiences an excellent feeling of stability. The dimensions of the neck cover 102 in the up-down direction are reduced, compared to a configuration in which the first to third cooling members 500, 501, and 502 are stored in a vertical orientation in the first to third pockets 124, 125, and 126. Therefore, the user can stably wrap the neck cover 102 around the neck.

The neck cover 102 is sewn to the headgear main body 101, and thus, a displacement of the neck cover 102 in the circumferential direction can be easily prevented. Moreover, the neck cover 102 is connected only to the rear part of the headgear main body 101, and thus, the user can easily move the head up, down, left, and right. Even if the user moves the head, the neck cover 102 is not easily displaced from the neck. Therefore, the first and second cooling members 500 and 501 are not easily displaced in the circumferential direction from the carotid arteries 600 and 601. In particular, the length W1 of the upper end part 121a of the protruding part 121 in the left-right direction is shorter than the diameter W2 of the headgear main body 101, and thus, the headgear main body 101 can be easily moved with respect to the neck cover 102. The neck cover 102 includes the protruding part 121, and thus, the front part and the left and right side parts of the headgear main body 101 can be easily spaced from the neck cover 102 upward.

Sixth Embodiment

Below, a headgear according to a sixth embodiment of the present invention will be described with reference to FIGS. 41 to 53. The headgear includes a headgear main body 201 to be worn on a head, a neck cover 202 to be wrapped around the neck, first and second attachment parts for detachably attaching the neck cover 202 to the headgear main body 201, and first to third holding parts for holding the first to third cooling members 500, 501, and 502.

Figure 47:
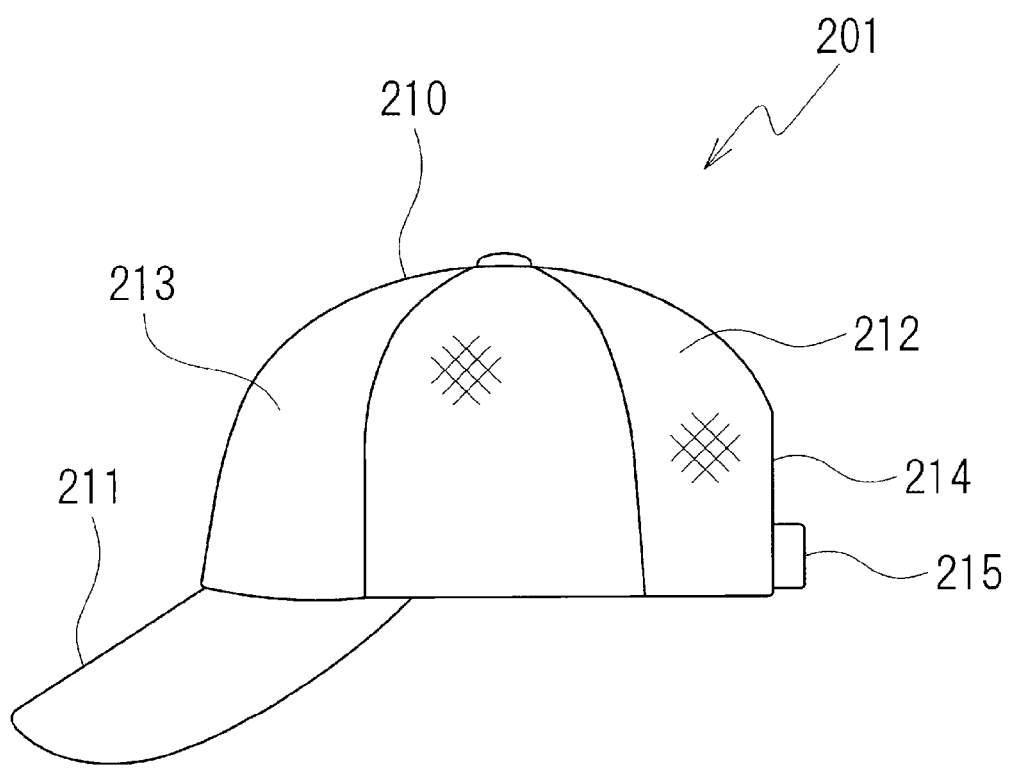
FIG. 47 is a side view illustrating a headgear main body of the headgear.
Figure 48:
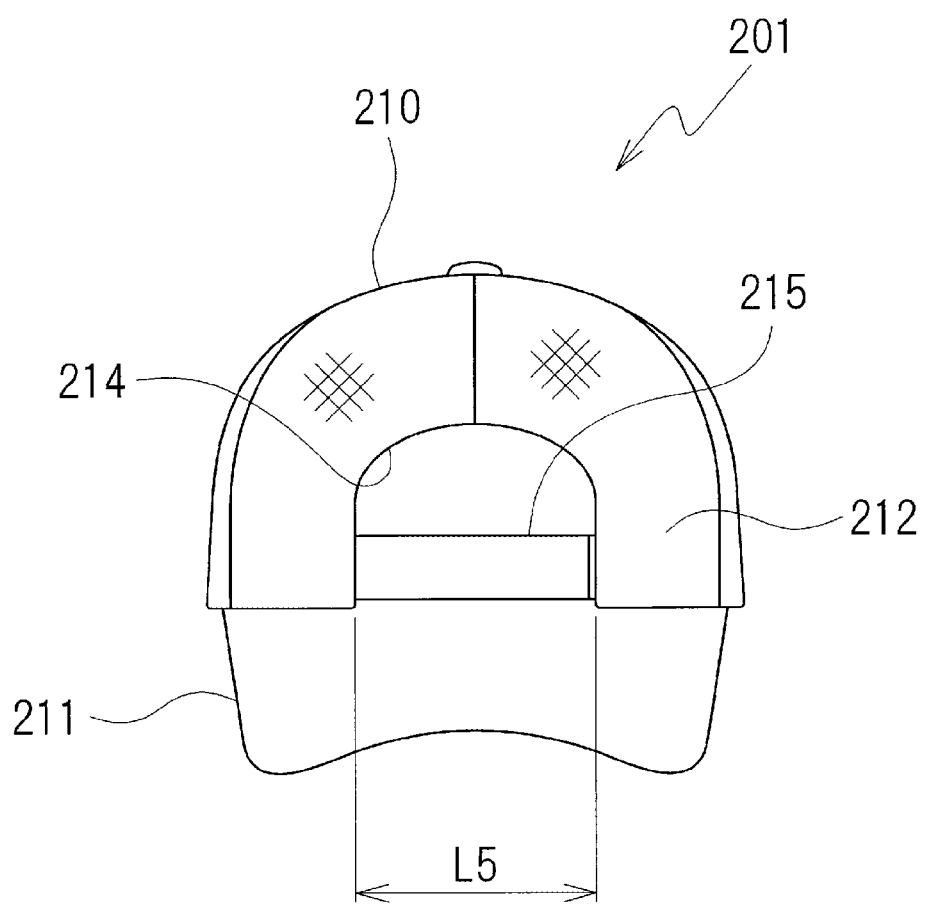
FIG. 48 is a view of the headgear main body seen from the rear side.

FIGS. 47 and 48 illustrate an example of the headgear main body 201. The headgear main body 201 has the shape of a cap. The headgear main body 201 includes a major main body part 210 having a hemispherical shape that opens downward, and a brim part 211 that extends to the front from a front part of a lower end part of the major main body part 210. The major main body part 210 is worn on a head of a user. An opening part of the major main body part 210 has a substantially circular shape. The major main body part 210 is made of any type of fabrics. Various materials may be used for the fabric and a porous material such as a mesh material is an example of a material that is suitable for the fabric. It is preferable that a porous material is used for at least a part of the major main body part 210. In particular, it is preferable that a rear part of the major main body part 210 is made of a porous material. That is, it is preferable that an air-permeable part 212 made of a porous material is provided at least in the rear part of the major main body part 210. A base part of the brim part 211 is sewn to a front part of the opening part of the major main body part 210. A portion of the opening part of the major main body part 210 excluding the base part of the brim part 211 is the air-permeable part 212. It is noted that, in the present embodiment, the front part of the major main body part 210 is an air-impermeable part 213 made of an air-impermeable material. However, the entire major main body part 210 may be the air-permeable part 212, or the entire major main body part 210 may be the air-impermeable part 213.

A main body notch part 214 extending upward is formed in a rear part of a lower end part of the headgear main body 201. The main body notch part 214 has a substantially semicircular shape, for example. The main body notch part 214 is formed in the air-permeable part 212 of the major main body part 210. A length of a lower end part of the main body notch part 214 is an opening length L5 of the main body notch part 214. The headgear main body 201 is provided with an adjustment band 215 so as to bridge the main body notch part 214 in the left-right direction. The adjustment band 215 is composed of a pair of left and right band-shaped pieces. The band-shaped pieces in the pair of left and right band-shaped pieces are detachably coupled to each other. The adjustment band 215 makes it possible to increase and decrease a separation distance of the main body notch part 214 in the left-right direction, and thereby to increase and decrease a diameter (an opening size) of the opening part of the headgear main body 201. The band-shaped pieces in the pair of band-shaped pieces may be coupled to each other by various structures. For example, a plurality of engaging holes may be formed in a first band-shaped piece, and a plurality of engaging protrusions that can be engaged with the engaging holes may be formed in a second band-shaped piece. Furthermore, the band-shaped pieces in the pair of band-shaped pieces may be coupled to each other by a hook-and-loop fastener, for example. Moreover, the adjustment band 215 may be elastic. The elastic adjustment band 215 makes it possible to increase and decrease the separation distance of the main body notch part 214 in the left-right direction.

The neck cover 202 is made of any type of fabrics. The neck cover 202 has a shape extending in the left-right direction. The dimensions of the neck cover 202 in the left-right direction are set so that the neck cover 202 can surround the entire circumference of the neck of the user. The neck cover 202 includes a main neck part 220 and a protruding part 221. The main neck part 220 is a main part of the neck cover 202. The main neck part 220 includes a straight part 222 positioned at the center in the left-right direction and a pair of tapered parts 223 positioned on both the left and right sides of the main neck part 220. The straight part 222 has constant dimensions in the up-down direction. The dimensions of the tapered parts 223 in the up-down direction gradually decrease with the distance from the straight part 222.

The straight part 222 is provided with a first pocket 230, a second pocket 231, and a third pocket 232 as first to third holding parts. The first pocket 230 is provided in a left part of the straight part 222, the second pocket 231 is provided in a right part of the straight part 222, and the third pocket 232 is provided between the first pocket 230 and the second pocket 231. The first to third pockets 230, 231, and 232 are formed so as to have the same shape and size. The first to third pockets 230, 231, and 232 have a horizontally elongated rectangular shape. The first to third pockets 230, 231, and 232 have accommodation spaces that are independent of each other. Each of the first to third cooling members 500, 501, and 502 is accommodated in one of the first to third pockets 230, 231, and 232. The first to third pockets 230, 231, and 232 occupy almost the entire straight part 222. The first to third pockets 230, 231, and 232 are provided side by side in a row along the left-right direction. Adjacent ones of the first to third pockets 230, 231, and 232 are continuously provided without a gap, but may be provided with a gap. The dimensions of the straight part 222 in the left-right direction are identical to the total length of the first to third pockets 230, 231, and 232 in the left-right direction. The dimensions of the straight part 222 in the up-down direction are slightly smaller than the dimensions of the first to third pockets 230, 231, and 232 in the up-down direction. The first to third cooling members 500, 501, and 502 are respectively stored in the first to third pockets 230, 231, and 232, so that the long side direction of the first to third cooling members 500, 501, and 502 is the left-right direction.

Figure 43:
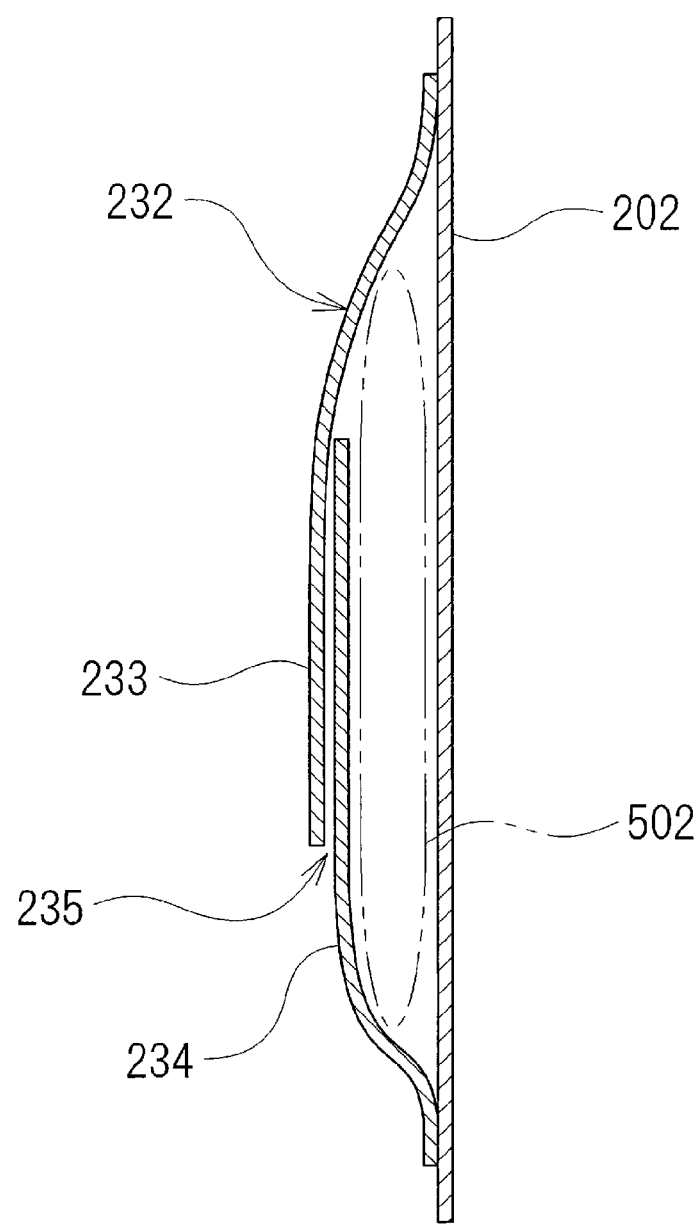
FIG. 43 is an enlarged view illustrating main parts of FIG. 41.
Figure 44:
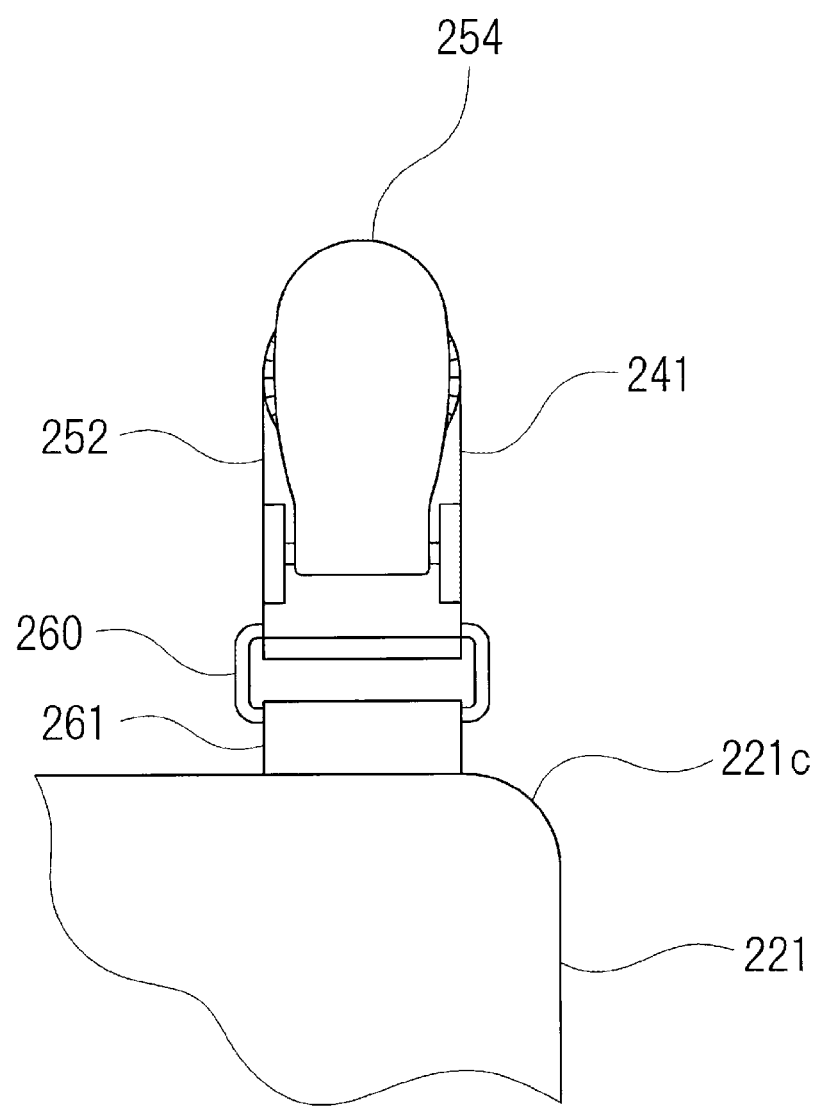
FIG. 44 is a cross-sectional view taken along line F-F in FIG. 41.

The first to third pockets 230, 231, and 232 may have various configurations. In the present embodiment, the first to third pockets 230, 231, and 232 are provided on a front surface of the straight part 222. However, the first to third pockets 230, 231, and 232 may be provided on a back surface of the straight part 222. As illustrated in FIG. 43, the first to third pockets 230, 231, and 232 are composed of an upper piece 233 and a lower piece 234. The upper piece 233 and the lower piece 234 are sewn to the front surface of the neck cover 202. A lower part of the upper piece 233 overlaps a front side of an upper part of the lower piece 234. Opening parts 235 of the first to third pockets 230, 231, and 232 are formed between the lower part of the upper piece 233 and the upper part of the lower piece 234. The first to third cooling members 500, 501, and 502 are introduced and removed through the opening parts 235 of the first to third pockets 230, 231, and 232.

Upper end parts of the tapered parts 223 are inclined. Lower end parts of the tapered parts 223 are arranged in line with a lower end part of the straight part 222. Hook-and-loop fasteners 224 are provided on the tapered parts 223. The hook-and-loop fasteners 224 are coupling parts that detachably couple a left end part and a right end part of the neck cover 202. The left end part and the right end part of the neck cover 202 are coupled by the hook-and-loop fasteners 224 in an overlapping manner.

The protruding part 221 protrudes upward from a center part of the straight part 222 of the main neck part 220 in the left-right direction. The protruding part 221 may have any shape, but in the present embodiment, the protruding part 221 has a horizontally elongated rectangular shape. A length L1 of an upper end part 221a of the protruding part 221 in the left-right direction is longer than lengths L21, L22, and L23 of the first to third pockets 230, 231, and 232 in the left-right direction. In the present embodiment, the lengths L21, L22, and L23 of the first to third pockets 230, 231, and 232 in the left-right direction are all the same. When the lengths L21, L22, and L23 of the first to third pockets 230, 231, and 232 in the left-right direction are different from each other, the length L1 of the upper end part 221a of the protruding part 221 in the left-right direction is longer than the length L23 in the left-right direction of the third pocket 232 positioned in the center. The length L1 of the upper end part 221a of the protruding part 221 in the left-right direction is shorter than a total length L3 of the three lengths of the first to third pockets 230, 231, and 232 in the left-right direction. A left end part 221b of the upper end part 221a of the protruding part 221 is positioned above the first pocket 230 within a range of the first pocket 230 in the left-right direction. The left end part 221b of the upper end part 221a of the protruding part 221 is positioned on the right side within the range of the first pocket 230 in the left-right direction, that is, closer to the center. A right end part 221c of the upper end part 221a of the protruding part 221 is positioned above the second pocket 231 within a range of the second pocket 231 in the left-right direction. The right end part 221c of the upper end part 221a of the protruding part 221 is positioned on the left side within the range of the second pocket 231 in the left-right direction, that is, closer to the center.

The neck cover 202 is provided with first and second attachment tools as first and second attachment parts. The first and second attachment tools may have various configurations. For example, the first and second attachment tools are preferably clips or dot buttons. In the present embodiment, first and second clips 240 and 241 are provided as the first and second attachment tools. The first and second clips 240 and 241 are attached to an upper end part of the neck cover 202. The first and second clips 240 and 241 are attached to the upper end part 221a of the protruding part 221. The first and second clips 240 and 241 protrude upward from the neck cover 202. The first clip 240 and the second clip 241 have the same configuration. The first clip 240 is positioned on the left side and the second clip 241 is positioned on the right side. The first clip 240 is positioned near the left end part 221b of the upper end part 221a of the protruding part 221 and the second clip 241 is positioned near the right end part 221c of the upper end part 221a of the protruding part 221. The first clip 240 is positioned above the first pocket 230 within the range of the first pocket 230 in the left-right direction. The first clip 240 is positioned closer to the third pocket 232 within the range of the first pocket 230 in the left-right direction. The second clip 241 is positioned above the second pocket 231 within the range of the second pocket 231 in the left-right direction. The second clip 241 is positioned closer to the third pocket 232 within the range of the second pocket 231 in the left-right direction. The first clip 240 is positioned to the left of the third pocket 232, and the second clip 241 is positioned to the right of the third pocket 232. A distance L4 between the first clip 240 and the second clip 241 is longer than the opening length L5 of the main body notch part 214 illustrated in FIG. 48.

Figure 45:
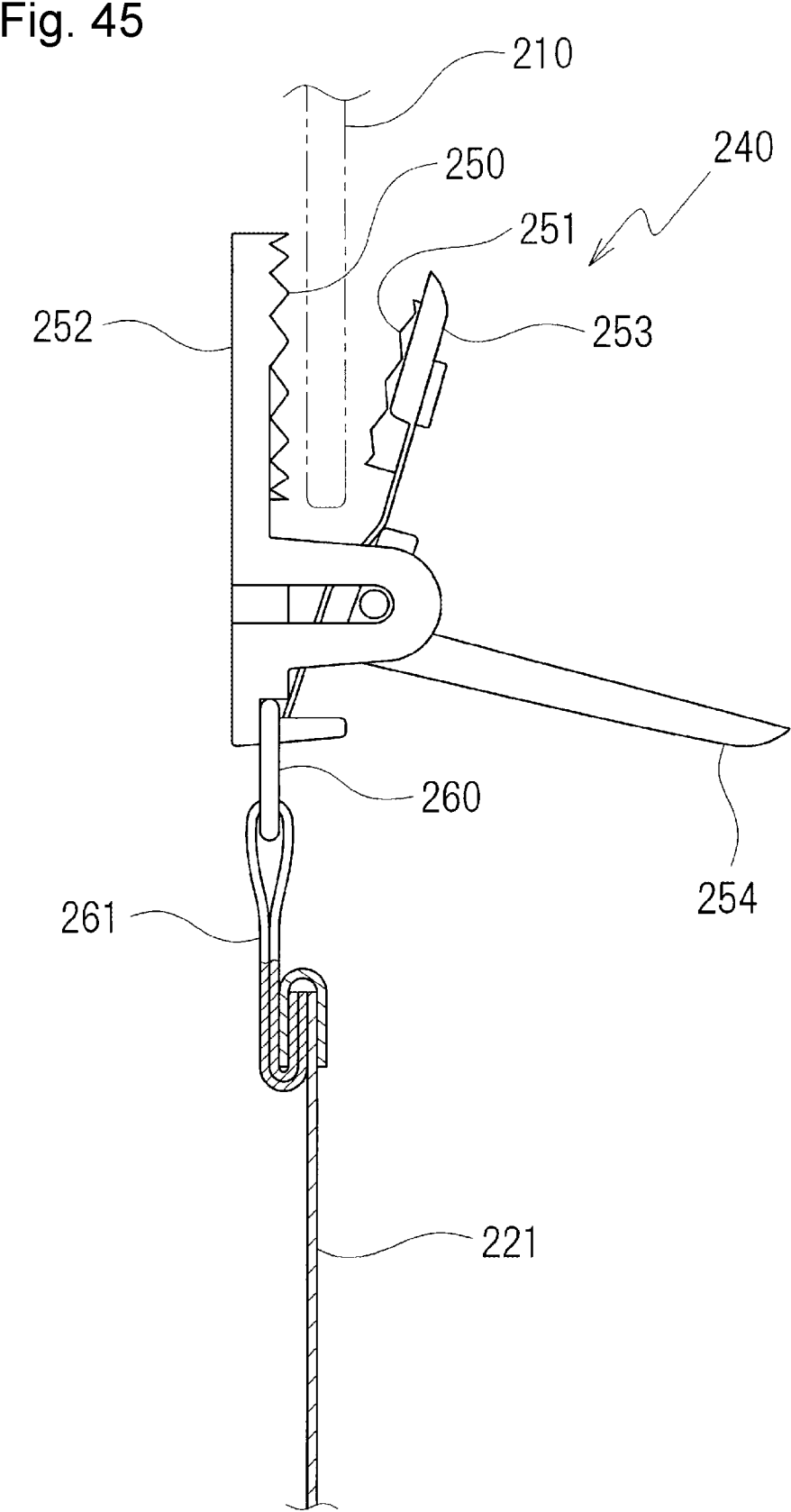
FIG. 45 is a cross-sectional view of a main part of the neck cover, including in part a broken line.
Figure 46:
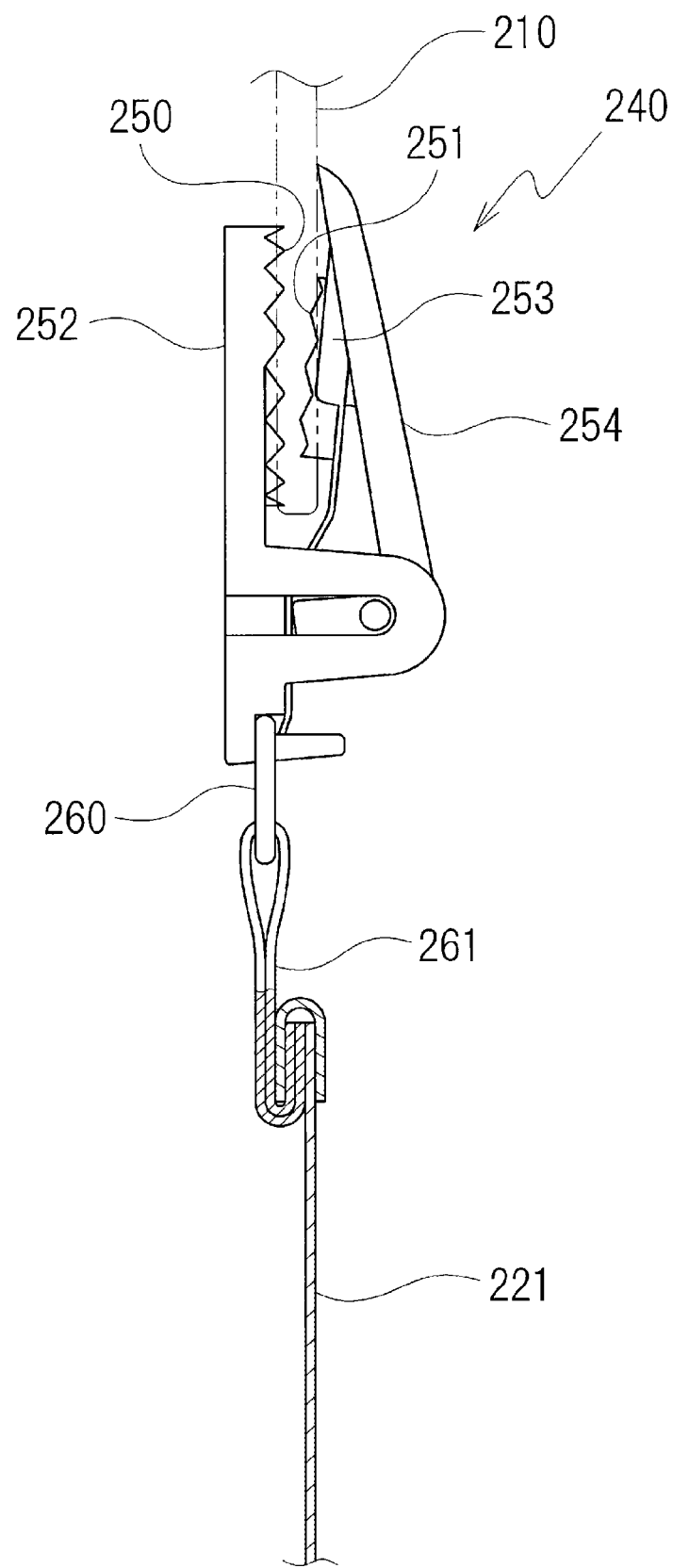
FIG. 46 is a cross-sectional view of a main part of the neck cover, including in part a broken line.

The first and second clips 240 and 241 have the same configuration, and thus, the first clip 240 will be representatively described. FIG. 45 illustrates an open state of the first clip 240, and FIG. 46 illustrates a closed state of the first clip 240. In FIGS. 45 and 46, the headgear main body 201 is illustrated by using a double-dashed line. FIG. 45 illustrates a state where the first clip 240 releases the headgear main body 201, and FIG. 46 illustrates a state where the first clip 240 grasps the headgear main body 201. The first clip 240 may abut against a back surface and a front surface of the lower end part of the headgear main body 201 to sandwich the lower end part of the headgear main body 201 in the front-back direction (inner-outer direction). The first clip 240 includes a first sandwiching part 250 and a second sandwiching part 251. The first sandwiching part 250 and the second sandwiching part 251 face each other. The first sandwiching part 250 and the second sandwiching part 251 sandwich the lower end part of the headgear main body 201. The first sandwiching part 250 is positioned on the front side, and the second sandwiching part 251 is positioned on the rear side. That is, the first sandwiching part 250 is positioned on the back side of the headgear main body 201, and the second sandwiching part 251 is positioned on the front side of the headgear main body 201. The first sandwiching part 250 abuts against the back surface of the headgear main body 201, and the second sandwiching part 251 abuts against the front surface of the headgear main body 201.

The first clip 240 includes a fixed piece 252 positioned on the front side, a movable piece 253 positioned behind the fixed piece 252, and a restraining piece 254 positioned behind the movable piece 253. The movable piece 253 is rotatably coupled to the fixed piece 252. The restraining piece 254 restrains the movable piece 253 from the outside. The movable piece 253 rotates back and forth around a lower end part thereof serving as a fulcrum. The lower end part of the movable piece 253 is attached to a lower end part of the fixed piece 252. The movable piece 253 is elastically deformable. Specifically, the movable piece 253 is a thin metal plate. When the movable piece 253 rotates to the rear side, the first clip 240 is in the open state, and when the movable piece 253 rotates to the front side, the first clip 240 is in the closed state. A normal state of the movable piece 253 is the open state in which the movable piece 253 opens to the rear side, and the movable piece 253 deforms elastically to rotate back and forth to reach the closed state. The restraining piece 254 maintains the movable piece 253 in the closed state. The restraining piece 254 can rotate back and forth. The restraining piece 254 is rotatably supported by the lower end part of the fixed piece 252. As illustrated in FIG. 45, the restraining piece 254 rotates further rearward than the movable piece 253 in the open state.

The fixed piece 252 is provided with the first sandwiching part 250, and the movable piece 253 is provided with the second sandwiching part 251. It is preferable that the first sandwiching part 250 and the second sandwiching part 251 are each formed in a concave-convex shape, so that the frictional force increases and the headgear main body 201 can be firmly sandwiched. The first clip 240 preferably sandwiches the air-permeable part 212 of the headgear main body 201, and can firmly sandwich the headgear main body 201 by a large frictional force. The first and second sandwiching parts 250 and 251 formed in a concave-convex shape are particularly effective. Convex parts of the first and second sandwiching parts 250 and 251 engage with air holes of the air-permeable part 212 of the headgear main body 201, so that a large frictional force is obtained. It is noted that the first clip 240 may be attached to the neck cover 202 in the opposite orientation in the front-rear direction.

A ring 260 is provided in a lower part of the first clip 240. The direction of a center line of the ring 260 is the front-rear direction. However, the direction of the center line of the ring 260 may be the left-right direction. The first clip 240 is rotatably coupled to the ring 260. A lower end part of the first clip 240 is coupled to the ring 260. The first clip 240 can rotate back and forth around the ring 260 serving as a fulcrum.

An attachment piece 261 is sewn to the upper end part 221a of the protruding part 221 of the neck cover 202. The attachment piece 261 protrudes upward from the protruding part 221. The attachment piece 261 passes through the ring 260 and folded around the ring 260. The attachment piece 261 is folded in half by the ring 260 and thus, overlaps in the front-rear direction. Both end parts of the attachment piece 261 are collectively sewn to the upper end part 221a of the protruding part 221. The ring 260 can rotate back and forth with respect to the attachment piece 261, and further, the first clip 240 can rotate back and forth with respect to the ring 260. Thus, the first clip 240 is attached to the neck cover 202 via the ring 260. Furthermore, the first clip 240 is attached to the upper end part 221a of the protruding part 221 via the ring 260 and the attachment piece 261.

<Attached State>

Figure 49:
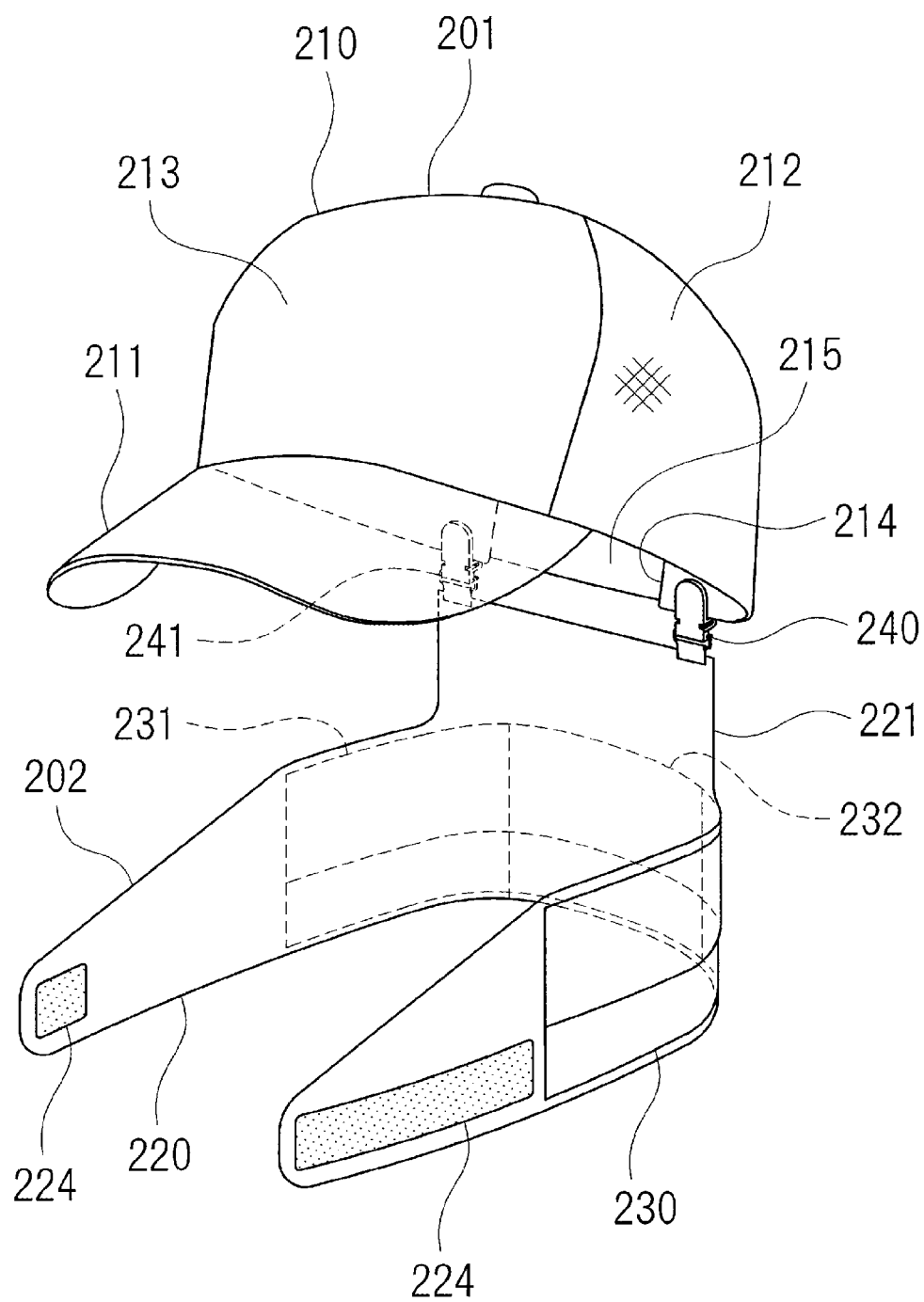
FIG. 49 is a perspective view illustrating a state where the neck cover is attached to the headgear main body.
Figure 50:
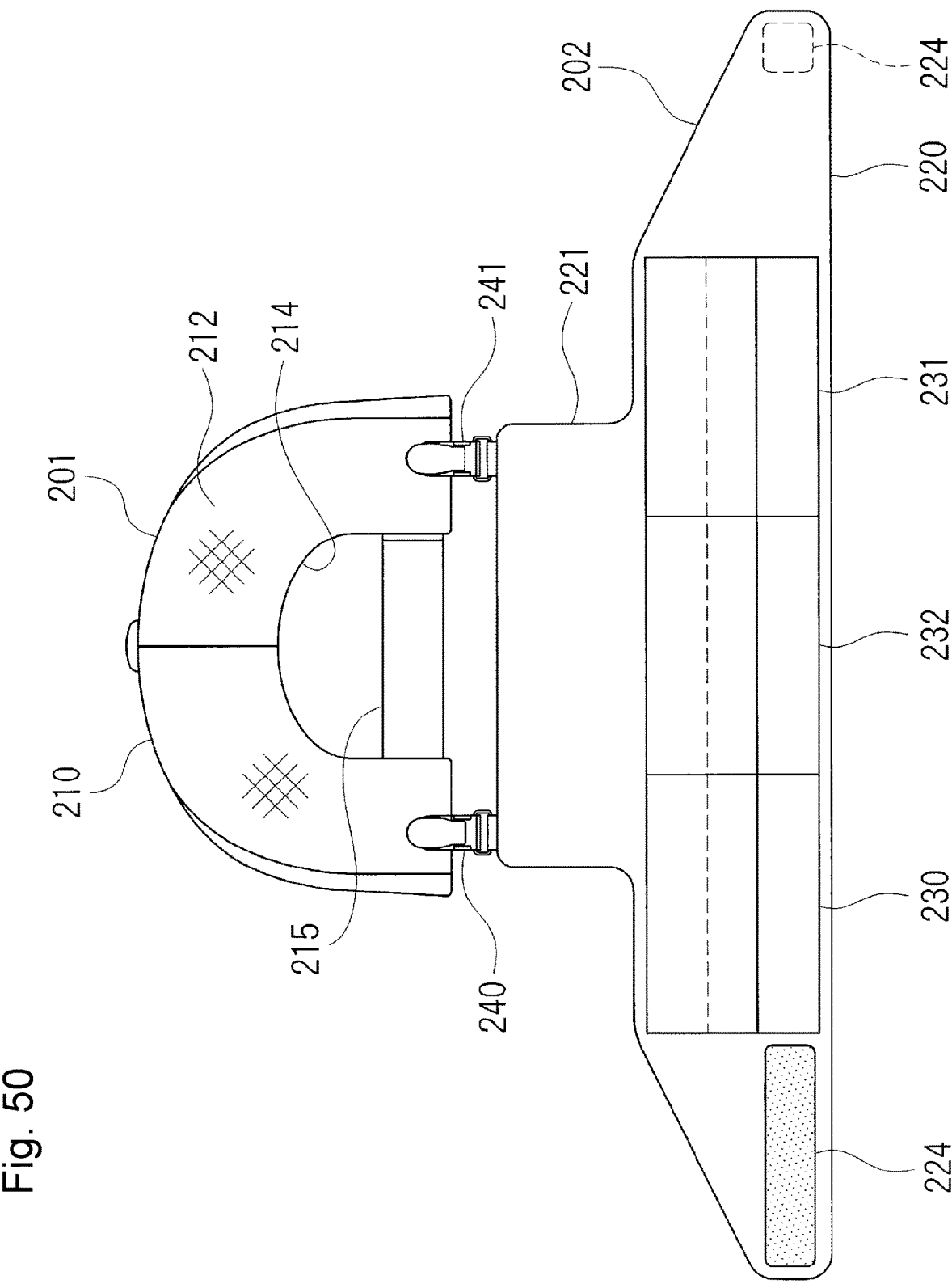
FIG. 50 is a diagram illustrating the state where the neck cover is attached to the headgear main body, seen from the rear side.

FIGS. 49 and 50 illustrate a state where the neck cover 202 is attached to the headgear main body 201. The user can easily attach the neck cover 202 to the headgear main body 201 by the first and second clips 240 and 241 and further, can easily remove the neck cover 202 from the headgear main body 201. The first and second clips 240 and 241 each sandwich the lower end part of the headgear main body 201. The first and second clips 240 and 241 sandwich portions on the left and right sides of the main body notch part 214. The first clip 240 sandwiches a portion on the left side of the main body notch part 214, and the second clip 241 sandwiches a portion on the right side of the main body notch part 214. Both the first and second clips 240 and 241 sandwich the air-permeable part 212 of the headgear main body 201.

<Worn State>

Figure 51:
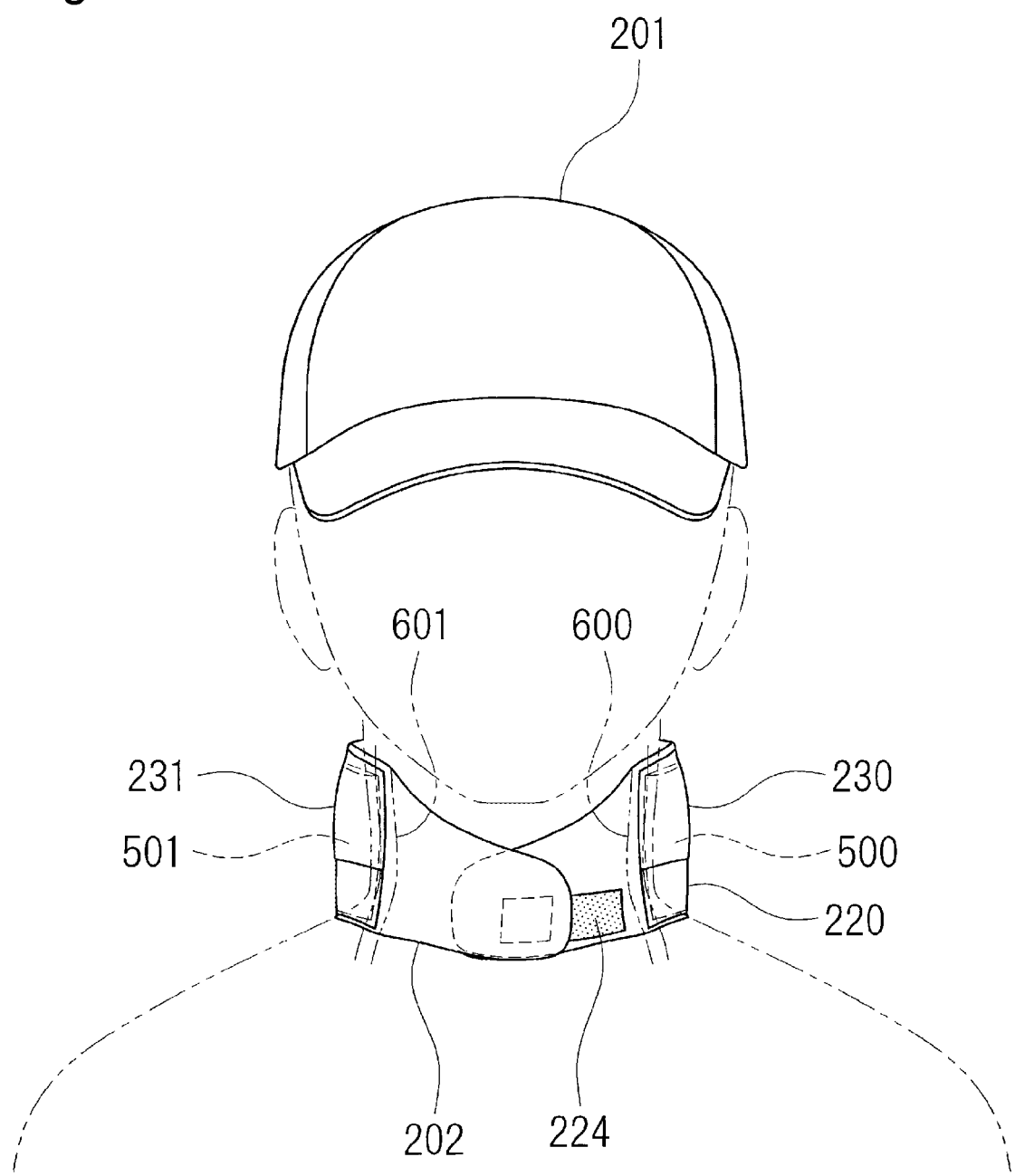
FIG. 51 is a diagram illustrating a worn state of the headgear, seen from the front side.
Figure 52:
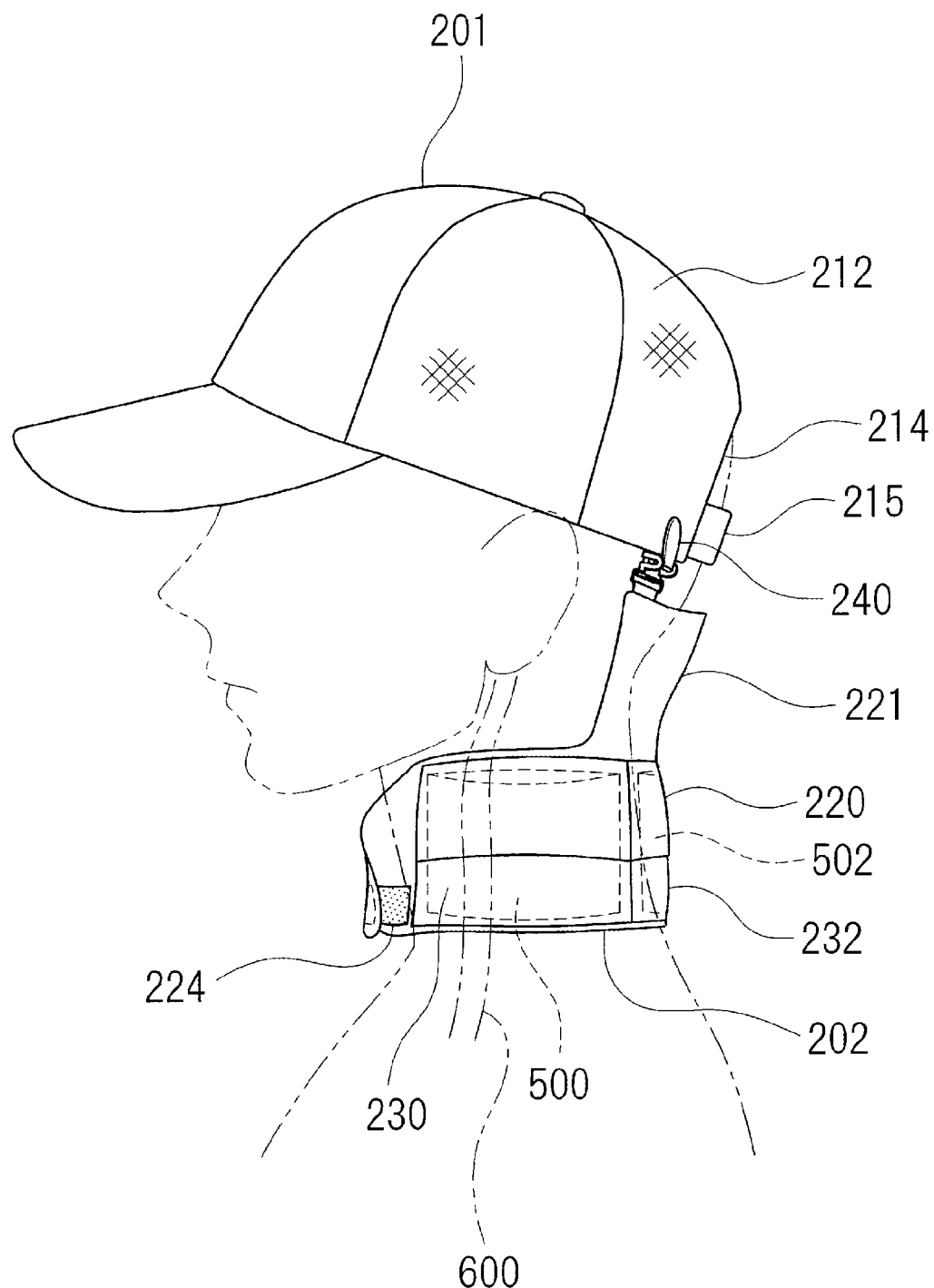
FIG. 52 is a side view illustrating the worn state of the headgear.
Figure 53:
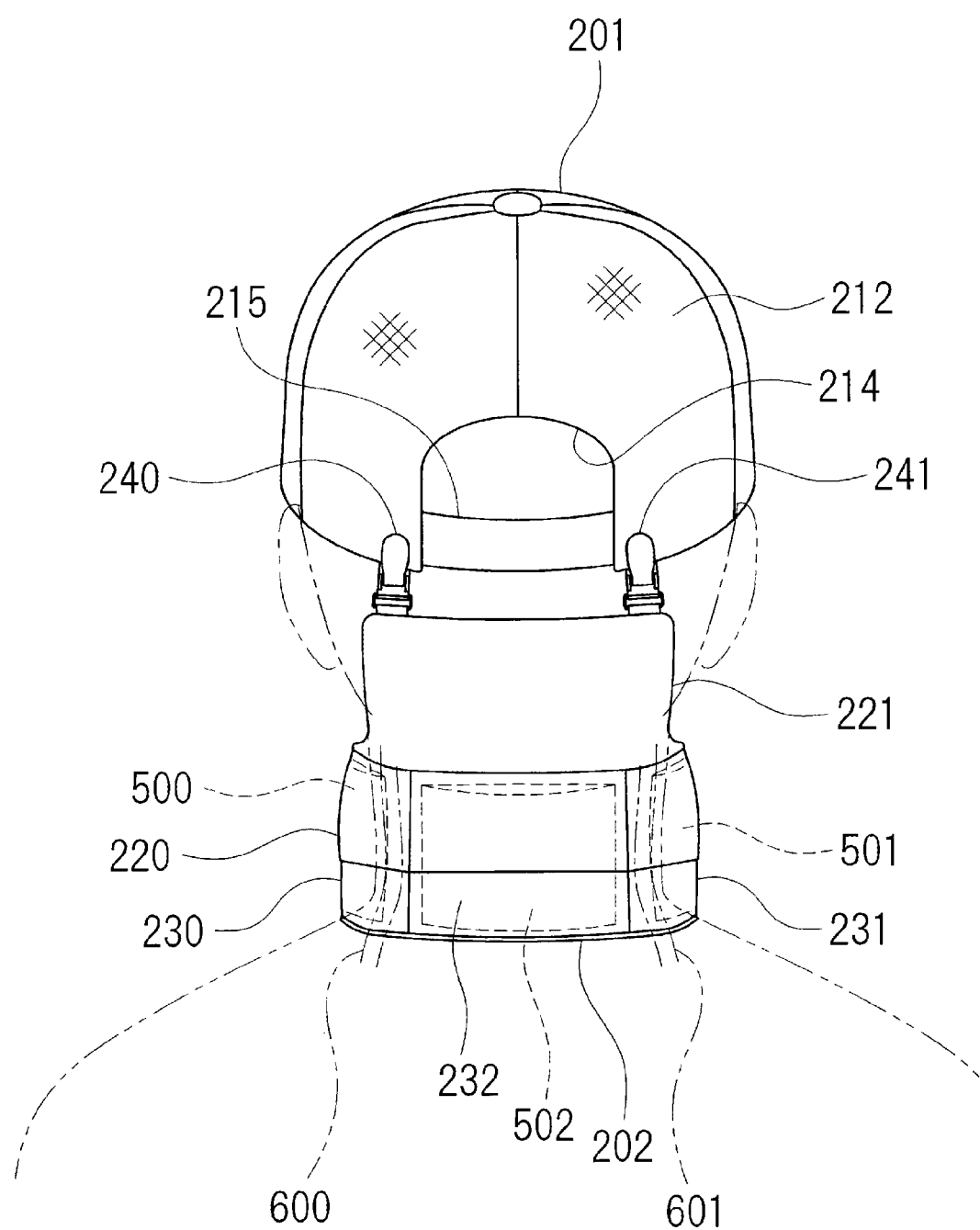
FIG. 53 is a diagram illustrating the worn state of the headgear, seen from the rear side.

FIGS. 51 to 53 illustrate a worn state. The first to third cooling members 500, 501, and 502 are respectively stored in advance in the first to third pockets 230, 231, and 232. The headgear main body 201 is worn on a head of a user and the neck cover 202 is wrapped around a neck of the user. The neck cover 202 is positioned below the ears. The user couples the left end part and the right end part of the neck cover 202 by the hook-and-loop fasteners 224. The left end part and the right end part of the neck cover 202 are coupled at a position in front of the neck. A coupling portion between the left end part and the right end part of the neck cover 202 is positioned below the chin. When the left end part and the right end part of the neck cover 202 are coupled, the neck cover 202 takes an annular shape, and the neck cover 202 surrounds the neck. It is easy for the user to tightly attach the neck cover 202 to the neck by the hook-and-loop fasteners 224.

When the neck cover 202 is wrapped around the neck, the first cooling member 500 is positioned on the left side of the neck, the second cooling member 501 is positioned on the right side of the neck, and the third cooling member 502 is positioned on the rear side of the neck. The band-like shape of the main neck part 220 extending in the left-right direction allows the first to third cooling members 500, 501, and 502 to be in close contact with the neck with the neck cover 202 therebetween. The first cooling member 500 faces a left carotid artery 300, and the second cooling member 501 faces a right carotid artery 300.

As described above, it is possible to effectively cool the left and right carotid arteries 600 and 601 by the first and second cooling members 500 and 501 stored in the first and second pockets 230 and 231. Therefore, heatstroke can be effectively prevented. Furthermore, the third cooling member 502 is stored in the third pocket 232. Therefore, it is possible to simultaneously cool a rear part of the neck, so that the cooling effect increases. The neck cover 202 includes the protruding part 221, and thus, the protruding part 221 can block sunlight shining on the back of the head. It is noted that, in a state where the neck cover 202 is attached to the neck and the neck cover 202 is attached to the headgear main body 201, the user can easily remove only the headgear main body 201 to the rear side, or can easily put the headgear main body 201 on the head.

The neck cover 202 is attached to the headgear main body 201 by the first and second clips 240 and 241, and thus, the neck cover 202 is stabilized. Therefore, when the neck cover 202 is wrapped around the neck, an excellent wearing feeling is obtained. The first and second clips 240 and 241 and the hook-and-loop fasteners 224 stabilize the position of the neck cover 202 in the circumferential direction and the up-down direction. By attaching the neck cover 202 to the headgear main body 201, a displacement of the neck cover 202 in the circumferential direction is prevented. Furthermore, the neck cover 202 is also prevented from being displaced downward. In particular, a center part of the neck cover 202 in the left-right direction is suspended from the rear part of the headgear main body 201 via the first and second clips 240 and 241, and thus, the center part of the neck cover 202 in the left-right direction is not easily displaced downward, and the neck cover 202 can be easily stabilized. Therefore, even if the user does not strongly tighten the neck cover 202 by the hook-and-loop fasteners 224, the neck cover 202 can be easily stabilized.

The left and right end parts 221*b* and 221*c* of the upper end part 221*a* of the protruding part 221 are attached to the headgear main body 201 via the first and second clips 240 and 241, respectively. Therefore, a state where the protruding part 221 is expanded in the left-right direction is maintained. The first and second clips 240 and 241 protrude upward from the protruding part 221, so that the user can easily attach the first and second clips 240 and 241 to the headgear main body 201. Furthermore, the protruding part 221 can be easily maintained in a stretched state in the left-right direction. The first and second clips 240 and 241 are rotatably supported by the ring 260, and thus, the headgear main body 201 easily swings back and forth with respect to the neck cover 202, and further, the neck cover 202 easily swings back and forth with respect to the headgear main body 201.

The first and second clips 240 and 241 are respectively positioned above the first and second pockets 230 and 231 within the ranges of the first and second pockets 230 and 231 in the left-right direction, and thus, it is possible to stabilize the first and second cooling members 500 and 501, which are heavy objects. In particular, it is preferable that the first and second clips 240 and 241 are respectively positioned closer to the center above the first and second pockets 230 and 231 within the ranges of the first and second pockets 230 and 231 in the left-right direction. When the first to third cooling members 500, 501, and 502 are stored in the first to third pockets 230, 231, and 232, the neck cover 202 can be easily stabilized. In particular, the third cooling member 502 prevents the center part of the neck cover 202 in the left-right direction from curving and deforming downward. Therefore, the wearing feeling of the neck cover 202 is improved. The first and second clips 240 and 241 are respectively attached at positions left and right of the main body notch part 214, and thus, a size adjustment by the adjustment band 215 is unlikely to be hindered.

Seventh Embodiment

Figure 54:
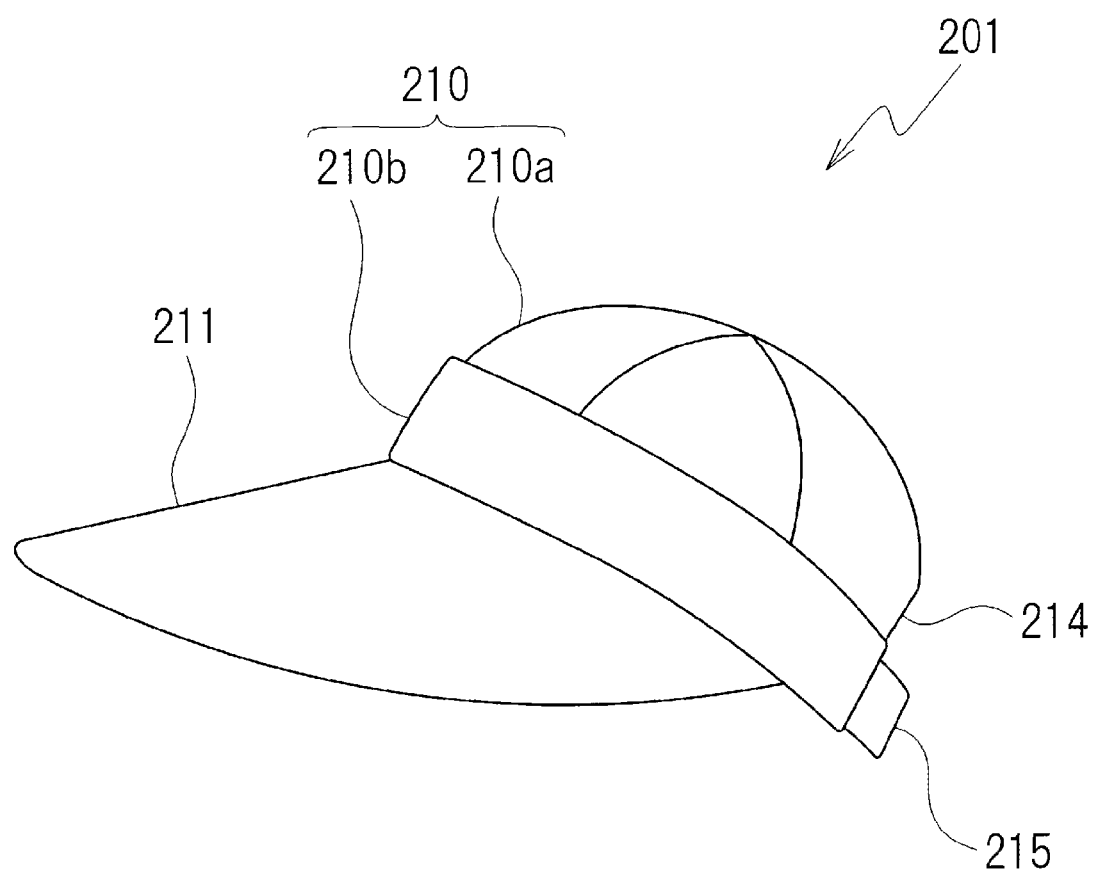
FIG. 54 is a side view illustrating a headgear main body of a headgear according to a seventh embodiment of the present invention.
Figure 55:
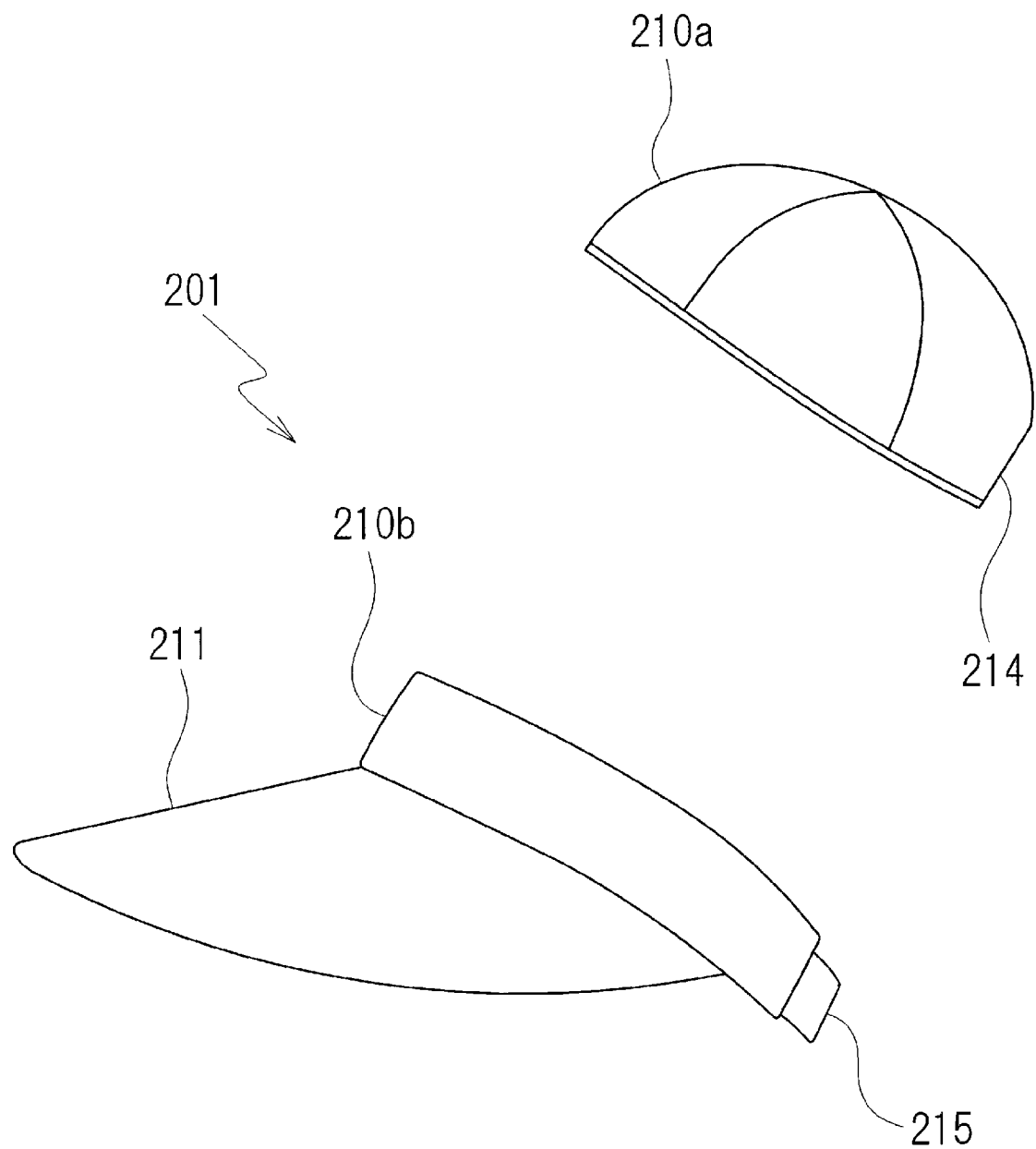
FIG. 55 is a side view illustrating the headgear main body.
Figure 56:
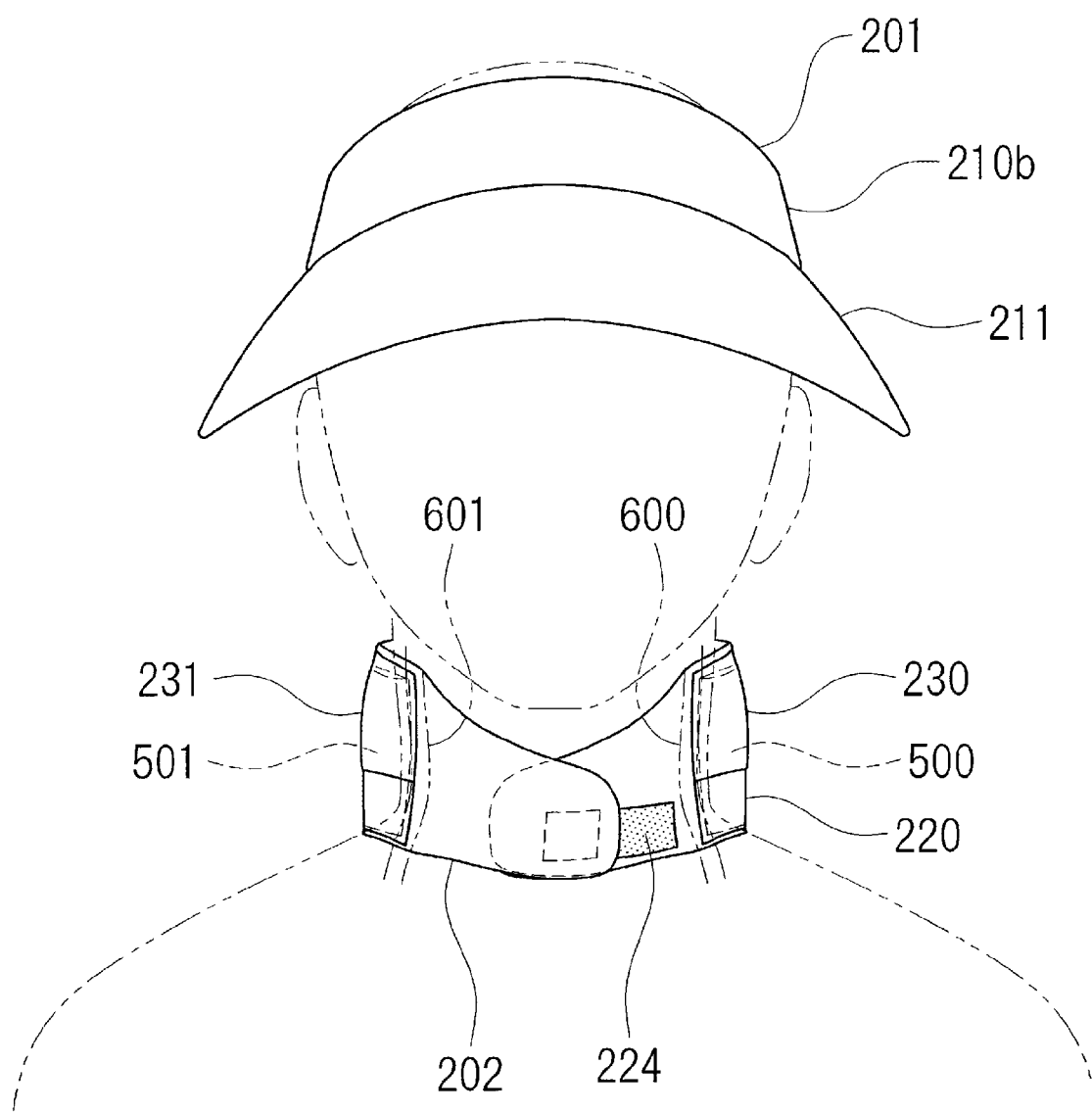
FIG. 56 is a diagram illustrating a worn state of the headgear, seen from the front side.
Figure 57:
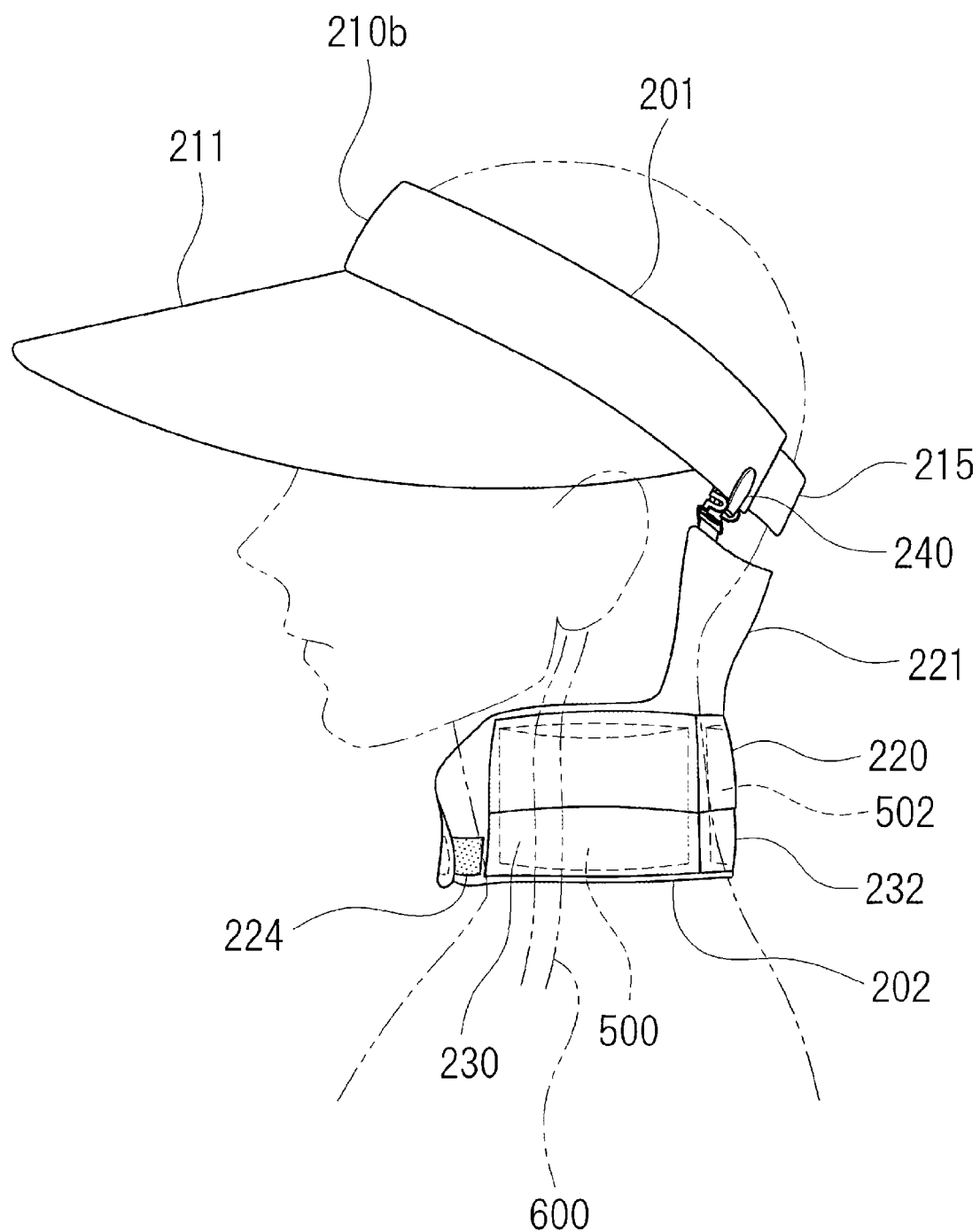
FIG. 57 is a side view illustrating the worn state of the headgear.
Figure 58:
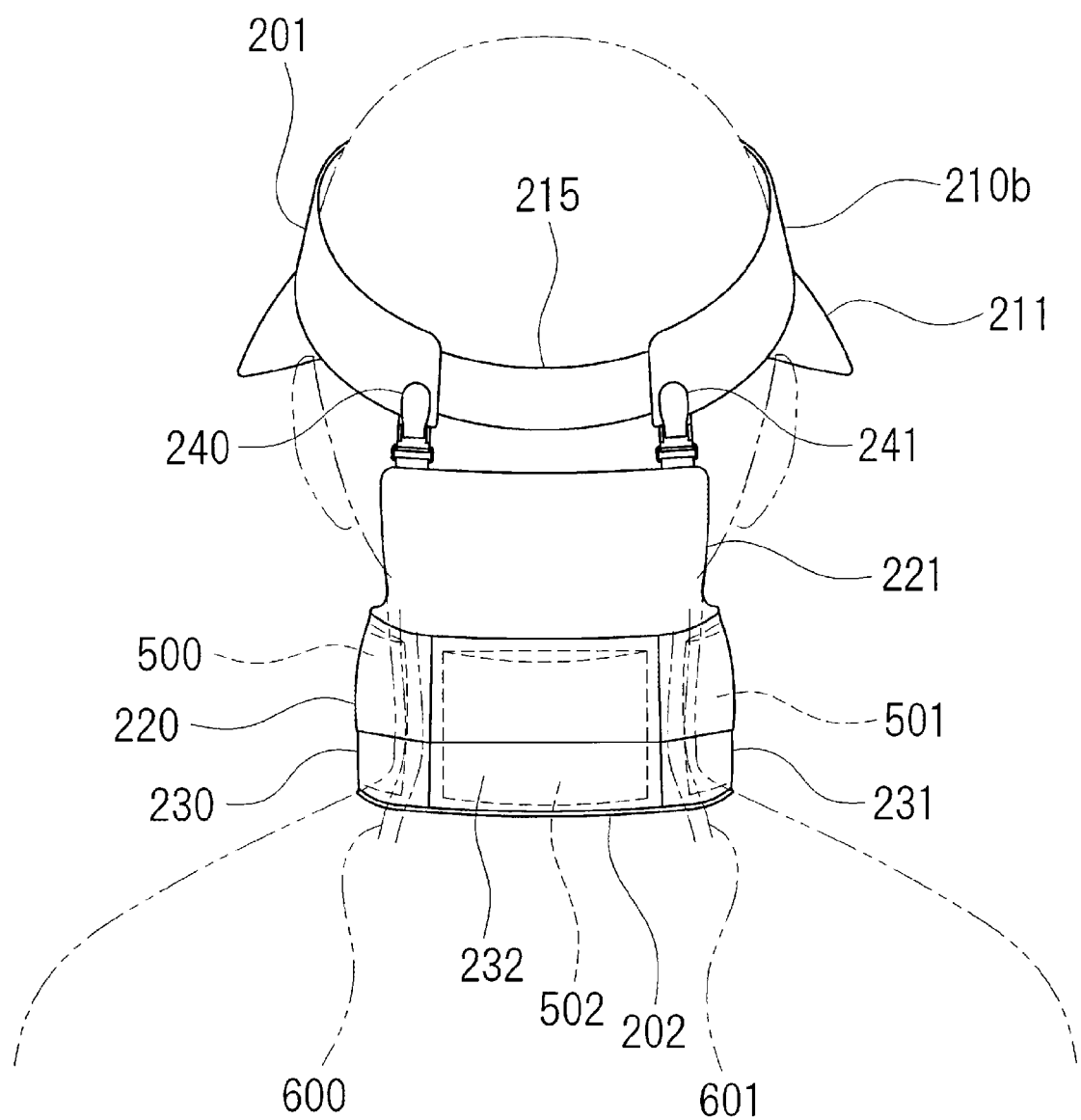
FIG. 58 is a diagram illustrating the worn state of the headgear, seen from the rear side.

It is noted that a case where the neck cover 202 is attached to headgear main body 201 having a cap shape has been described as an example. However, the headgear main body 201 may have the shape of a sun visor, for example. FIGS. 54 and 55 illustrate an example of the headgear main body 201 having the shape of the sun visor. The major main body part 210 of the headgear main body 201 having the shape of the sun visor includes an upper part 210*a* and a lower part 210*b*. The upper part 210*a* of the major main body part 210 can be detachably attached to the lower part 210*b* of the major main body part 210 and can be separated from the lower part 210*b* of the major main body part 210. The upper part 210*a* of the major main body part 210 has a hemispherical shape that opens downward. The lower part 210*b* of the major main body part 210 has an annular shape. The main body notch part 214 is provided in a rear part of the upper part 210*a* of the major main body part 210, and the adjustment band 215 is provided in a rear part of the lower part 210*b* of the major main body part 210. FIG. 54 illustrates a state where the upper part 210*a* is attached to the lower part 210*b*, and FIG. 55 illustrates a state where the upper part 210*a* is removed from the lower part 210*b*. Furthermore, FIGS. 56 to 58 illustrate a worn state where the neck cover 202 is attached to the headgear main body 201 having the shape of the sun visor. It is noted that FIGS. 56 to 58 illustrate a state where the upper part 210*a* is removed as an example. As described above, the headgear main body 201 may have various configurations.

Eighth Embodiment

Figure 59:
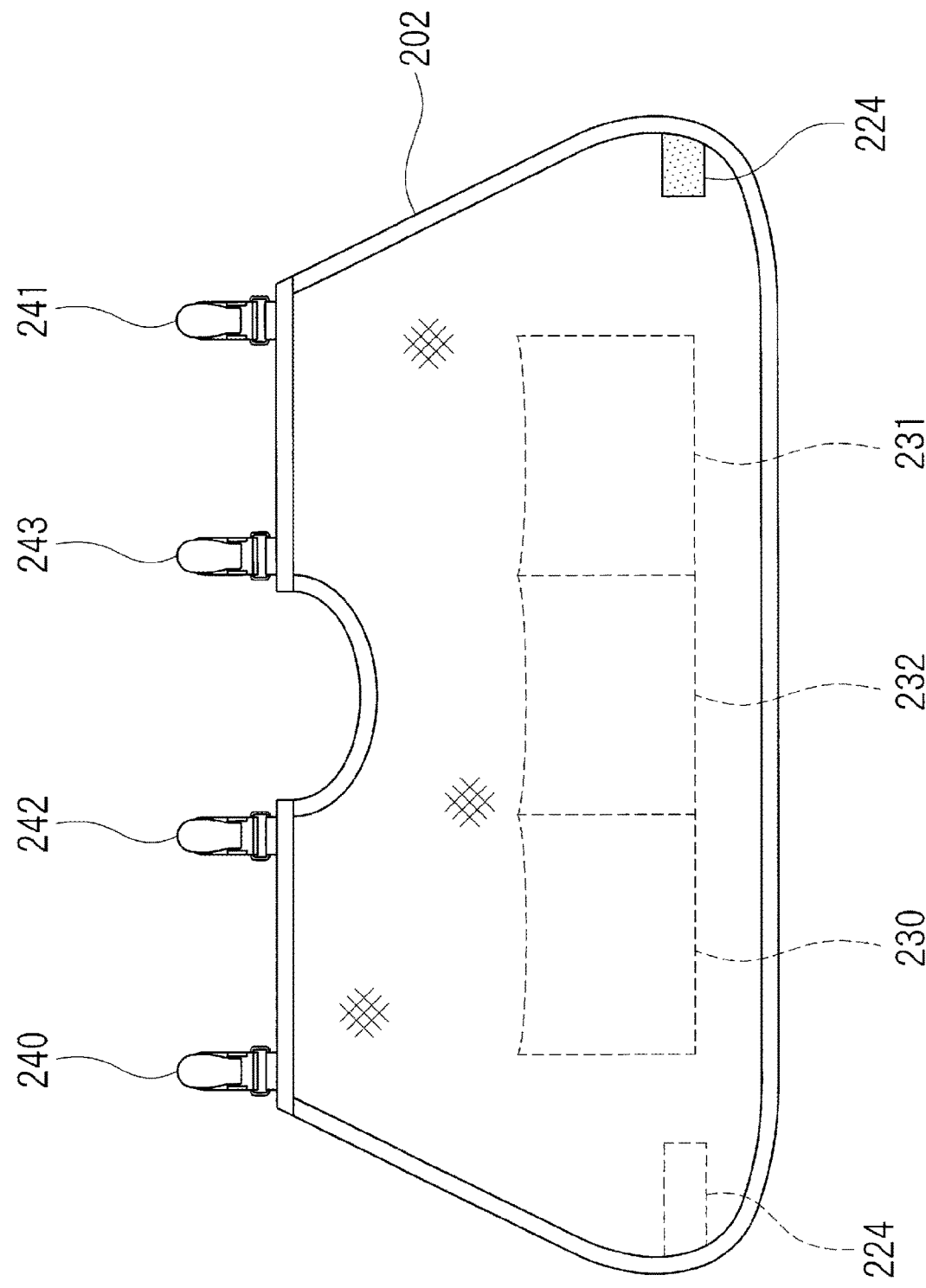
FIG. 59 is a front view of a neck cover of a headgear according to an eighth embodiment of the present invention, seen from a front surface side.
Figure 60:
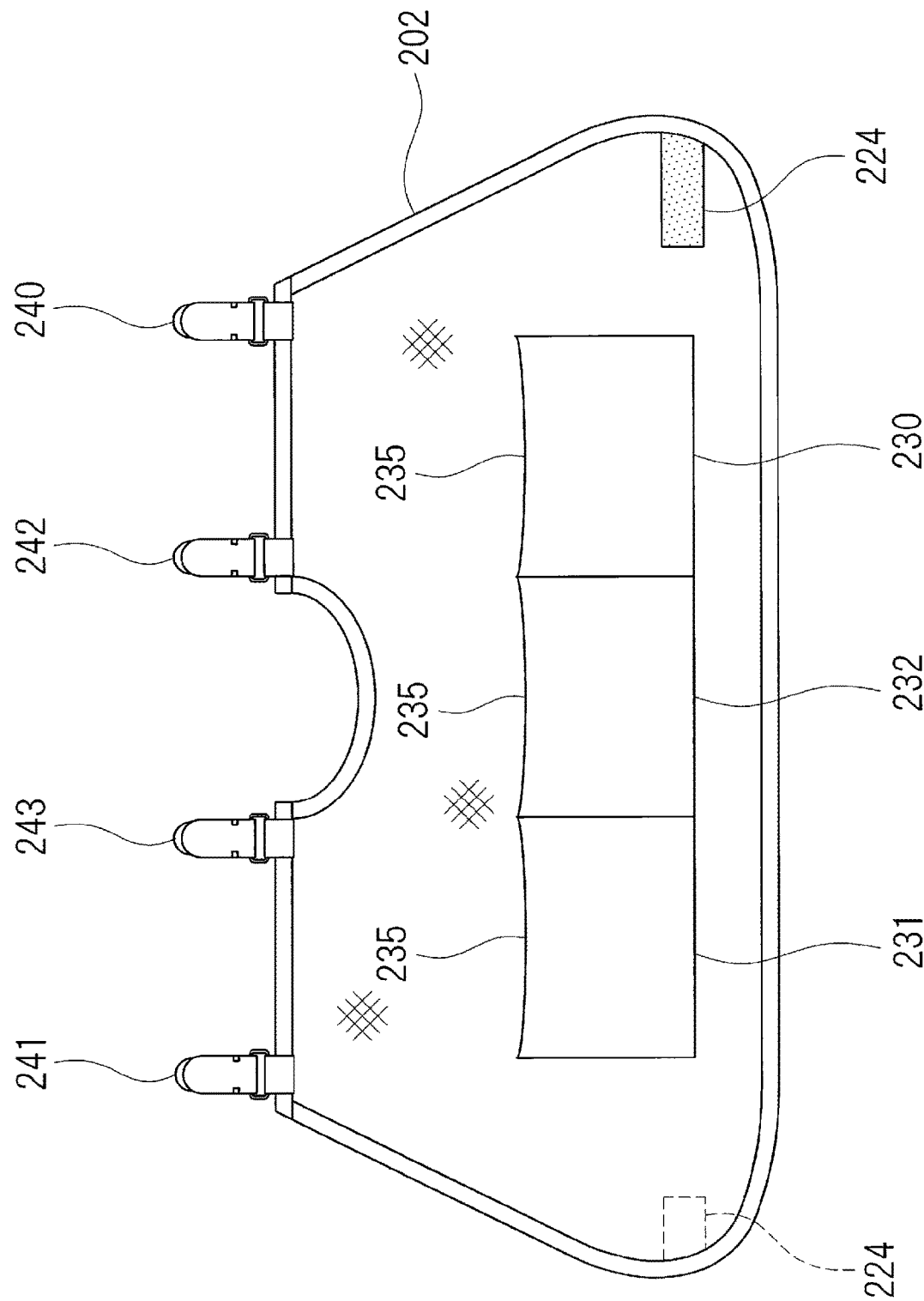
FIG. 60 is a rear view of the neck cover, seen from a back surface side.
Figure 61:
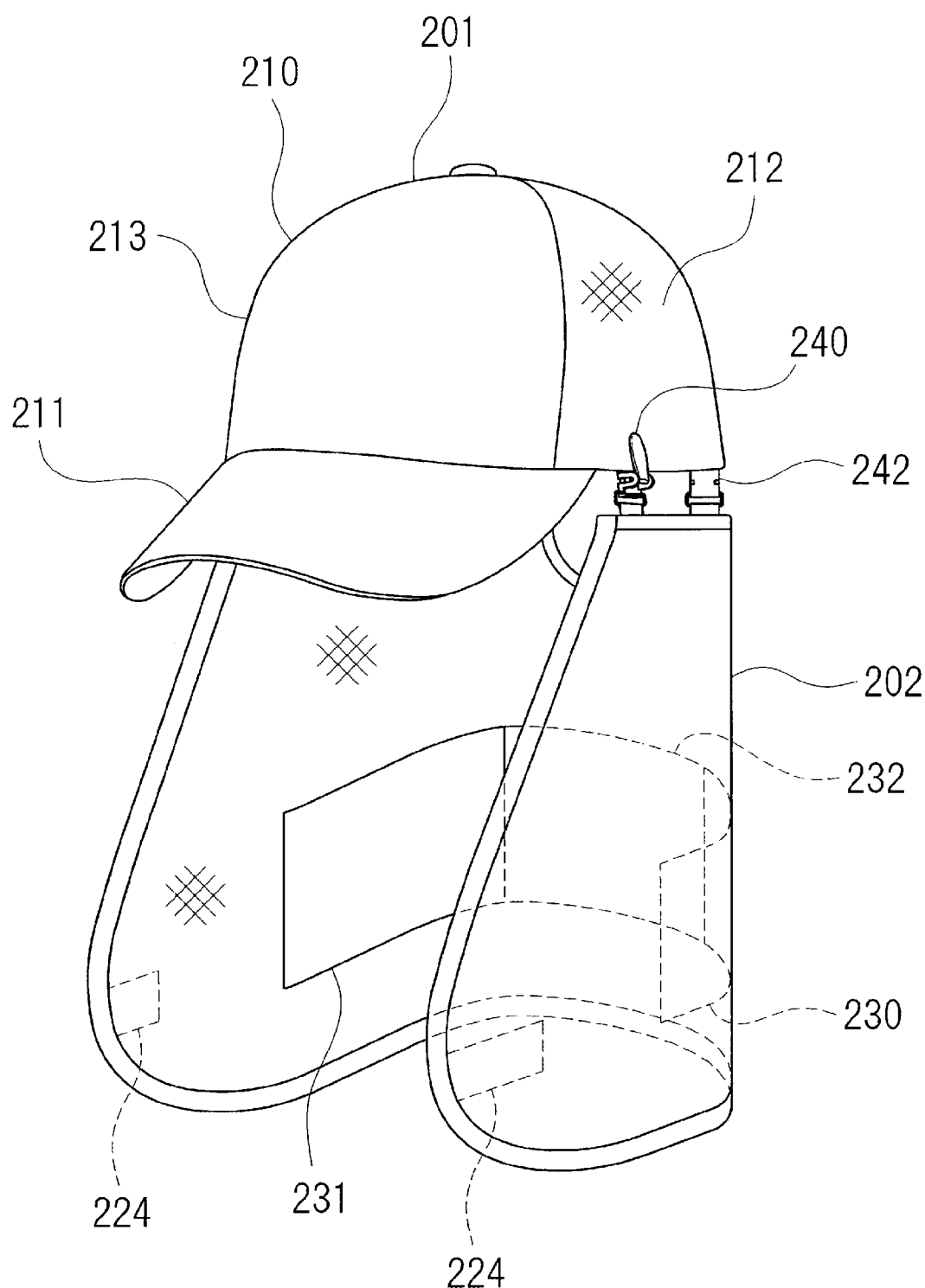
FIG. 61 is a perspective view illustrating a state where the neck cover is attached to the headgear main body.
Figure 62:
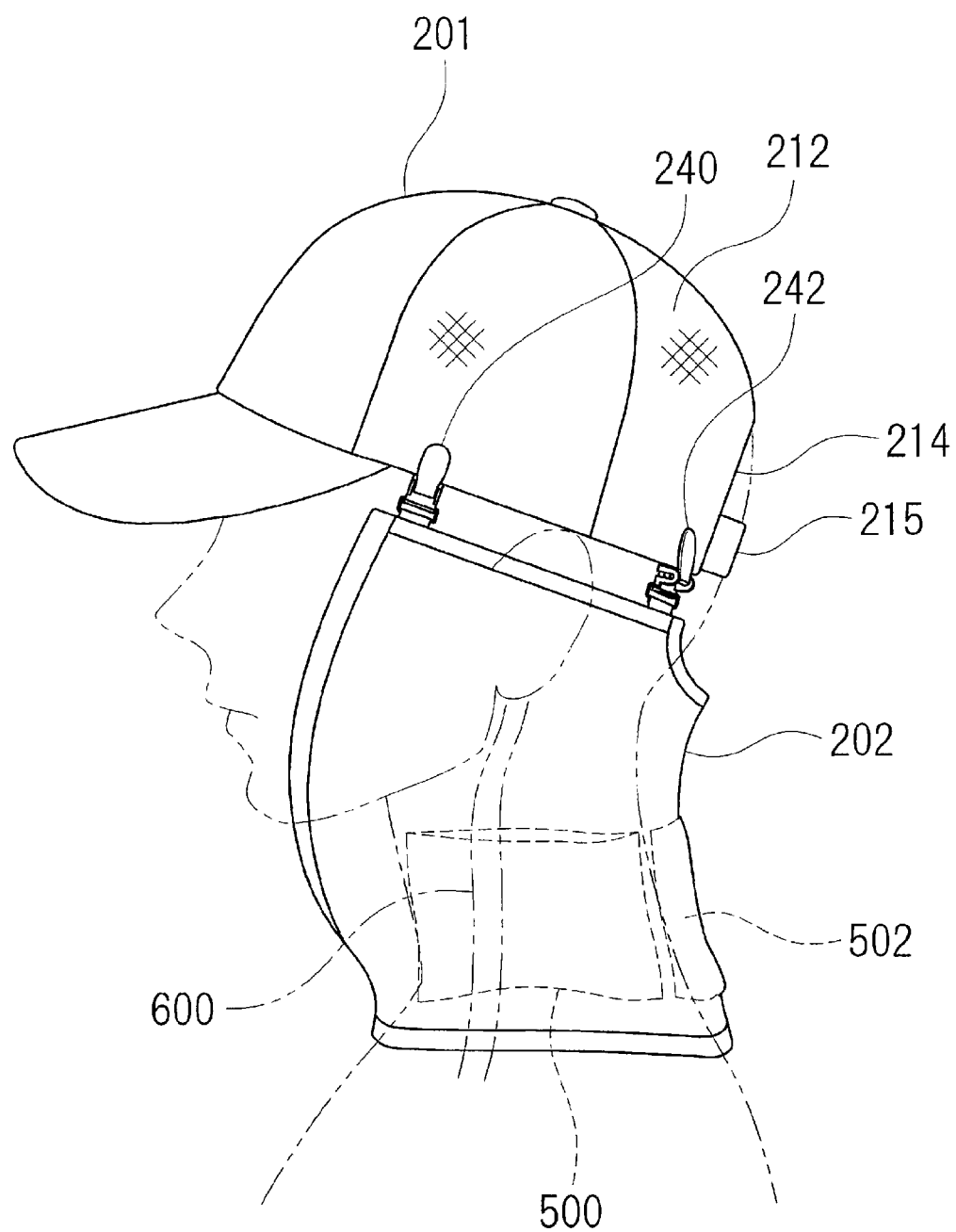
FIG. 62 is a side view illustrating a worn state of the neck cover.
Figure 63:
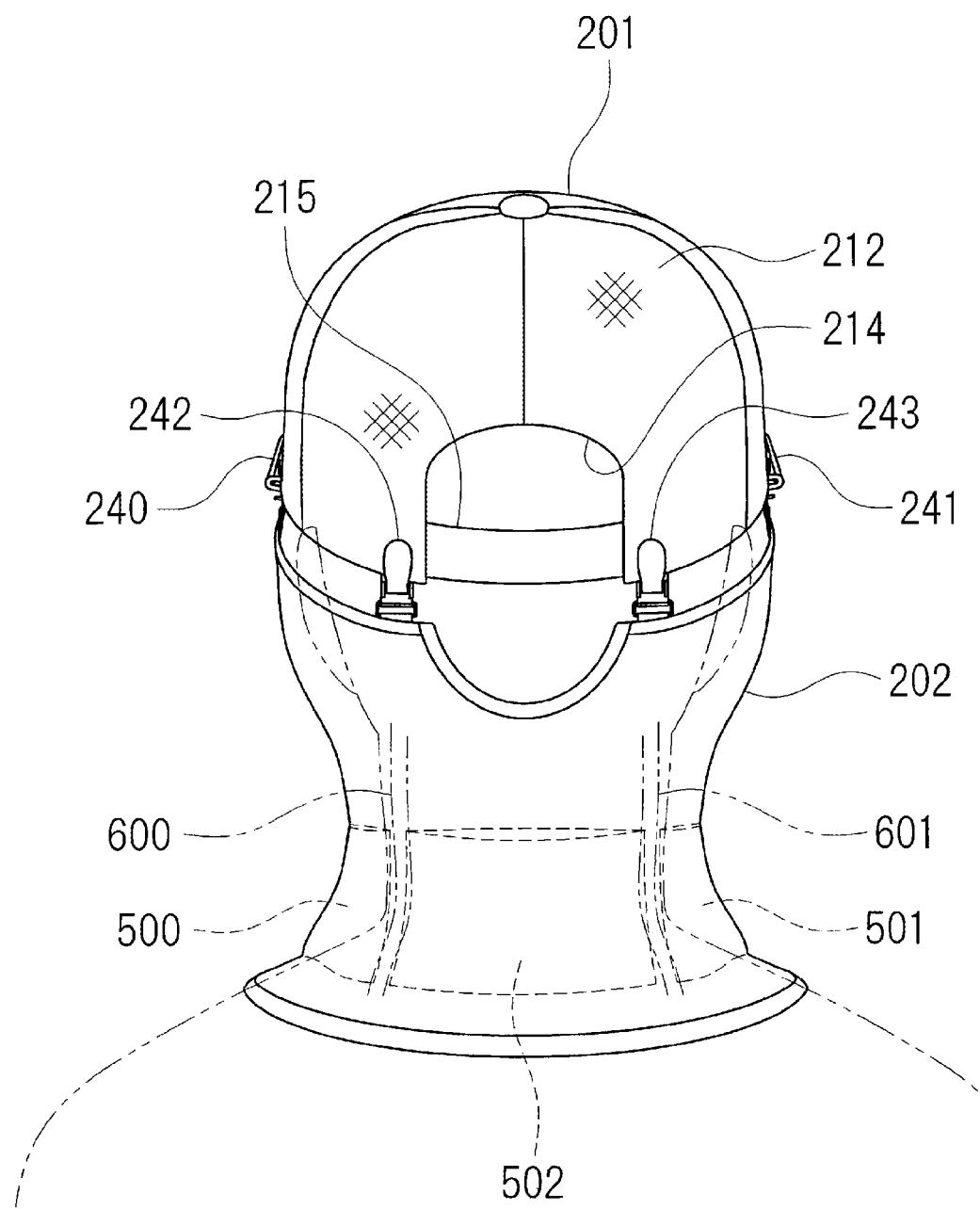
FIG. 63 is a diagram illustrating the worn state of the neck cover, seen from the rear side.

Furthermore, the shape of the neck cover 202 and the arrangement and number of clips may be changed in various ways. For example, as illustrated in FIGS. 59 and 60, the dimensions of the neck cover 202 in the up-down direction may be enlarged. In the present example, the first to third pockets 230, 231, and 232 are provided on the back surface of the neck cover 202. The first to third pockets 230, 231, and 232 include opening parts 235 at upper end parts thereof. First to fourth clips 240, 241, 242, and 243 are attached to the upper end part of the neck cover 202 at intervals in the left-right direction. The first to fourth clips 240, 241, 242, and 243 all have the same configuration, but may also have different configurations. The first and second clips 240 and 241 are respectively attached in the vicinity of the left and right end parts of the upper end part of the neck cover 202. The third and fourth clips 242 and 243 are attached at positions closer to the center part in the left-right direction than the first and second clips 240 and 241, respectively. FIG. 61 illustrates a state where the neck cover 202 is attached to the headgear main body 201 having a cap shape. Furthermore, FIGS. 62 and 63 illustrate a worn state. The third and fourth clips 242 and 243 are provided to the left and right of the main body notch part 214. The first and second clips 240 and 241 are provided in the vicinity of the base part of the brim part 211.

Ninth Embodiment

Figure 64:
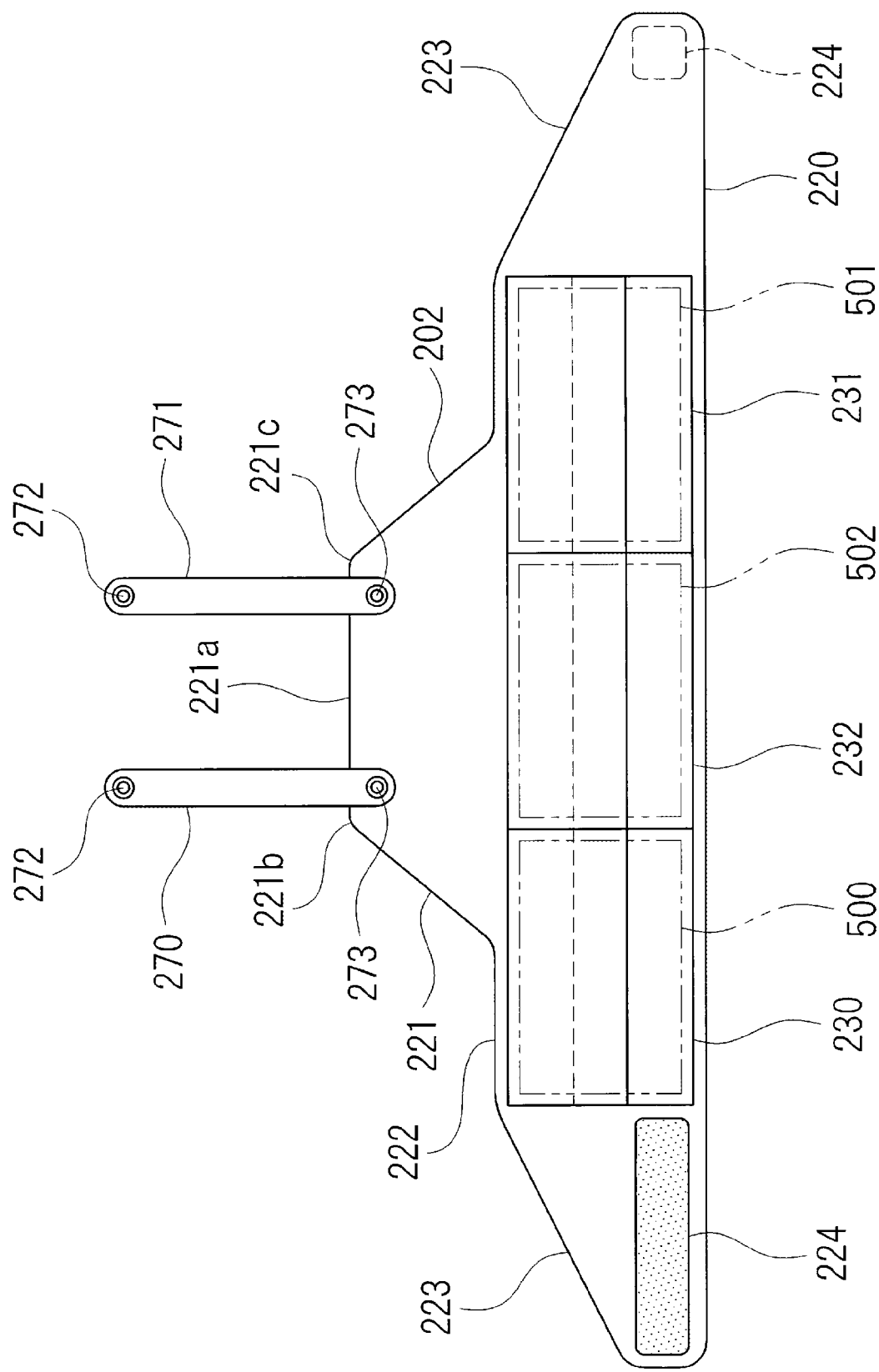
FIG. 64 is a front view of a neck cover of a headgear according to a ninth embodiment of the present invention, seen from a front surface side.
Figure 65:
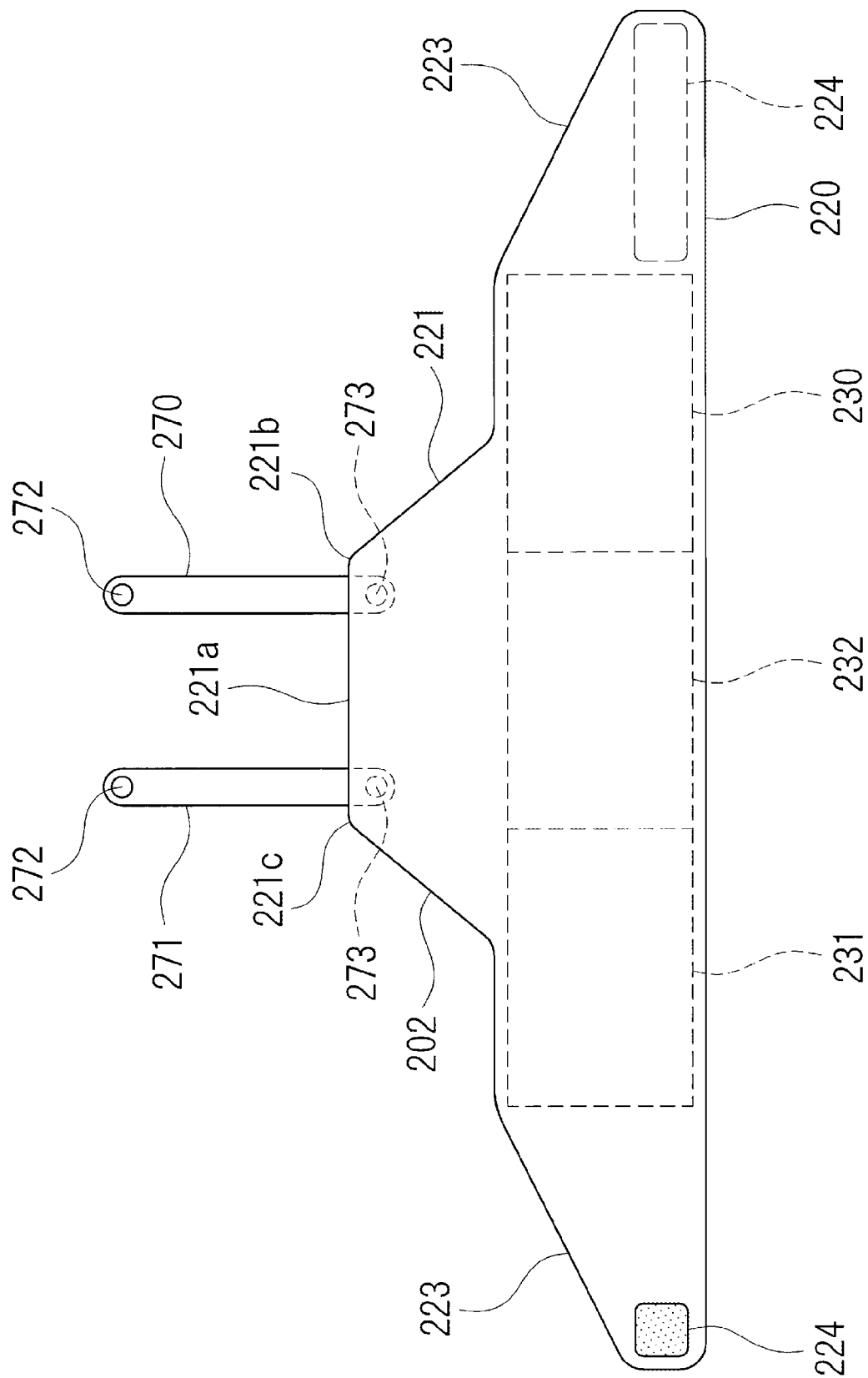
FIG. 65 is a rear view of the neck cover, seen from a back surface side.

It is noted that the clips are illustrated as an example of the attachment tools, but various types of attachment tools may be used. For example, first and second attachment bands 270 and 271 attached to the adjustment band 215 of the headgear main body 201 may be provided as the first and second attachment tools. An example of the first and second attachment bands 270 and 271 is illustrated in FIGS. 64 to 69. The neck cover 202 is illustrated in FIGS. 64 and 65. The first and second attachment bands 270 and 271 are attached to the upper end part 221*a* of the protruding part 221 of the neck cover 202 at intervals in the left-right direction. As in the present embodiment, the protruding part 221 may have a trapezoidal shape in which the length of the upper end part 221*a* is shorter than the length of the lower end part of the protruding part 221. The first and second attachment bands 270 and 271 are attached in the vicinity of the left and right end parts 221*b* and 221*c* of the upper end part 221*a* of the protruding part 221. The first and second attachment bands 270 and 271 have a band shape that is elongated in the up-down direction. Lower end parts of the first and second attachment bands 270 and 271 are sewn to the protruding part 221. The first and second attachment bands 270 and 271 extend upward from the upper end part 221*a* of the protruding part 221. First and second dot buttons 272 and 273 are attached to the upper and lower end parts of each of the first and second attachment bands 270 and 271, respectively.

Figure 66:
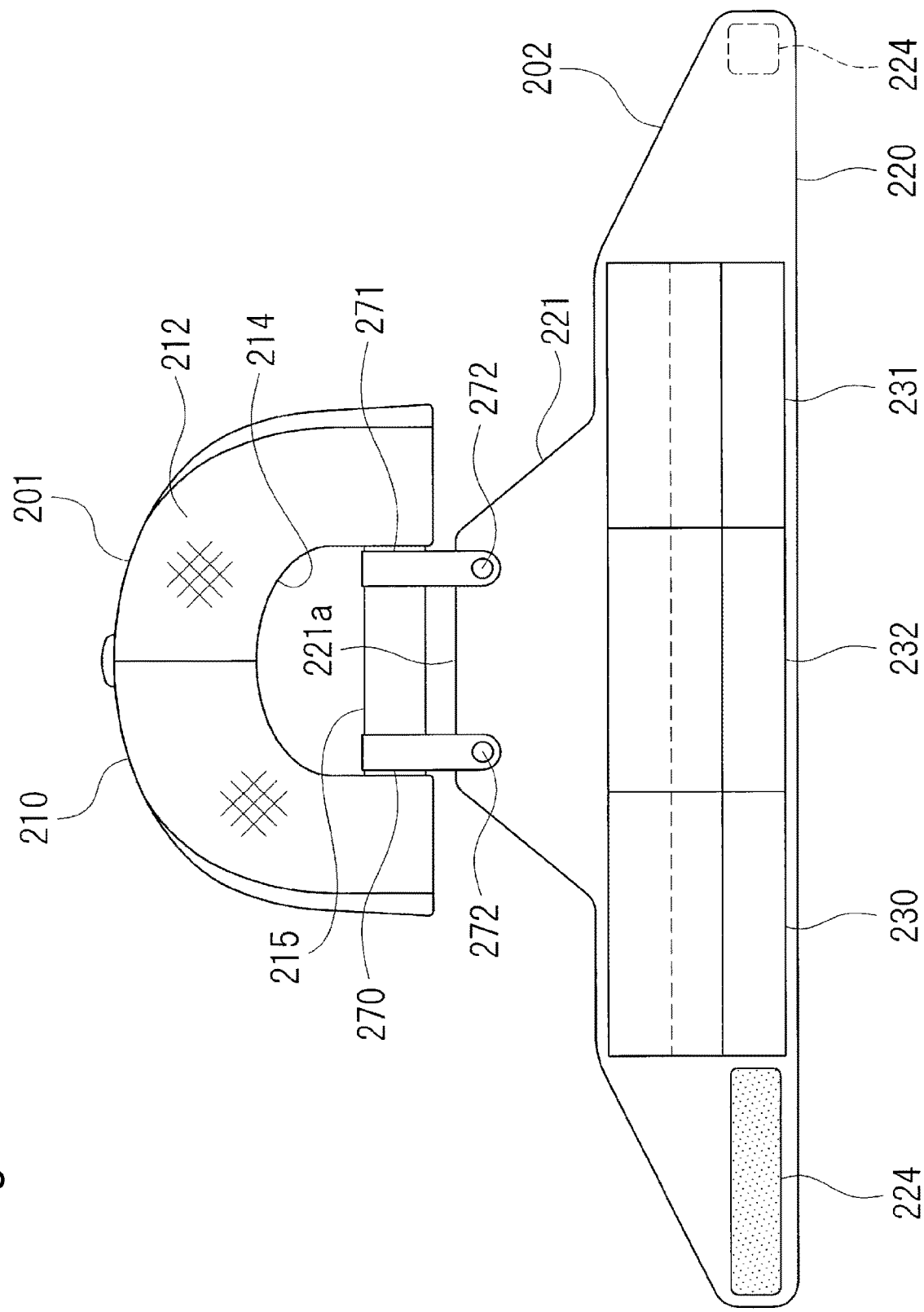
FIG. 66 is a diagram illustrating a state where the neck cover is attached to the headgear main body, seen from the rear side.
Figure 68:
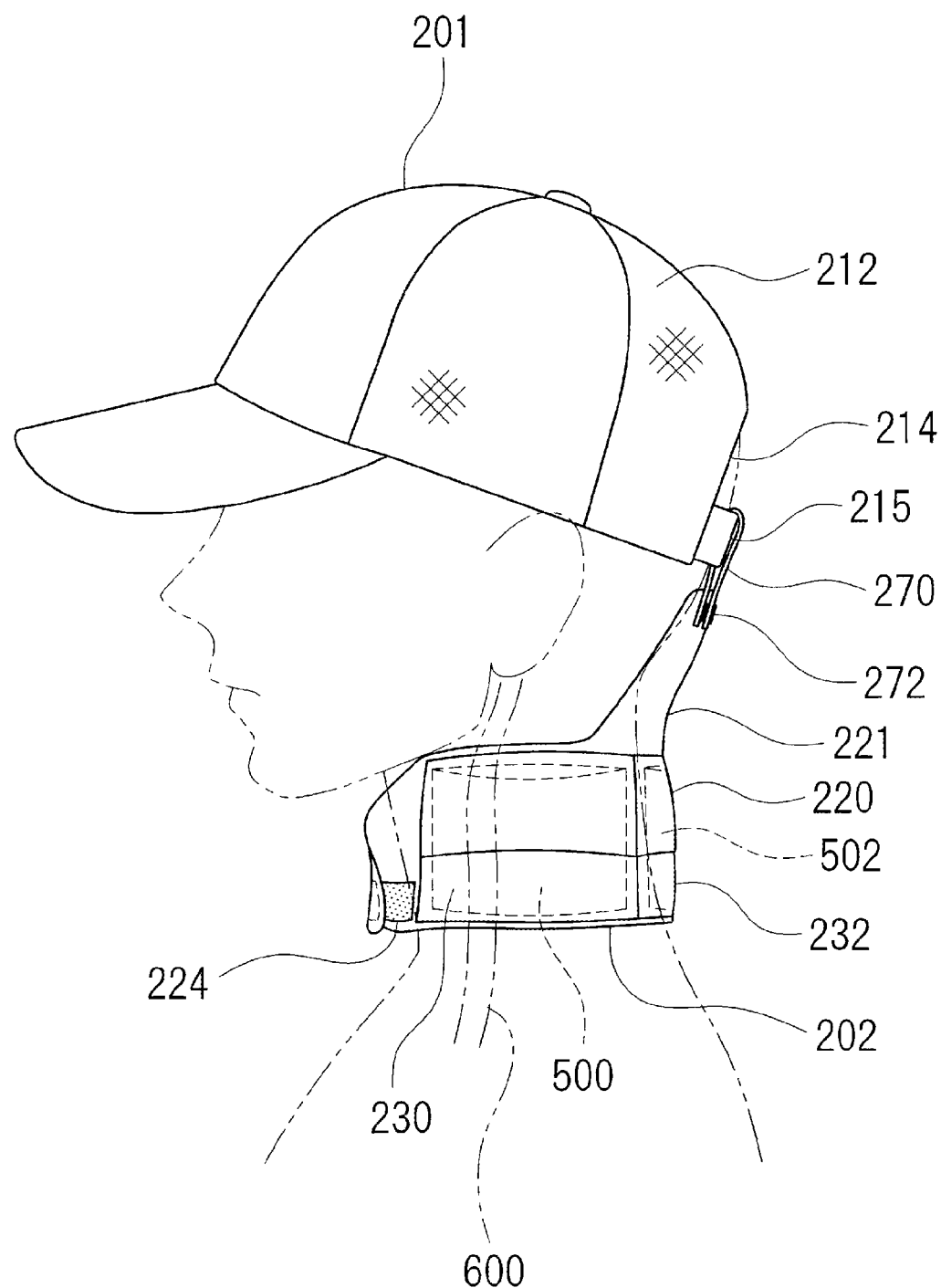
FIG. 68 is a side view illustrating a worn state of the headgear.
Figure 69:
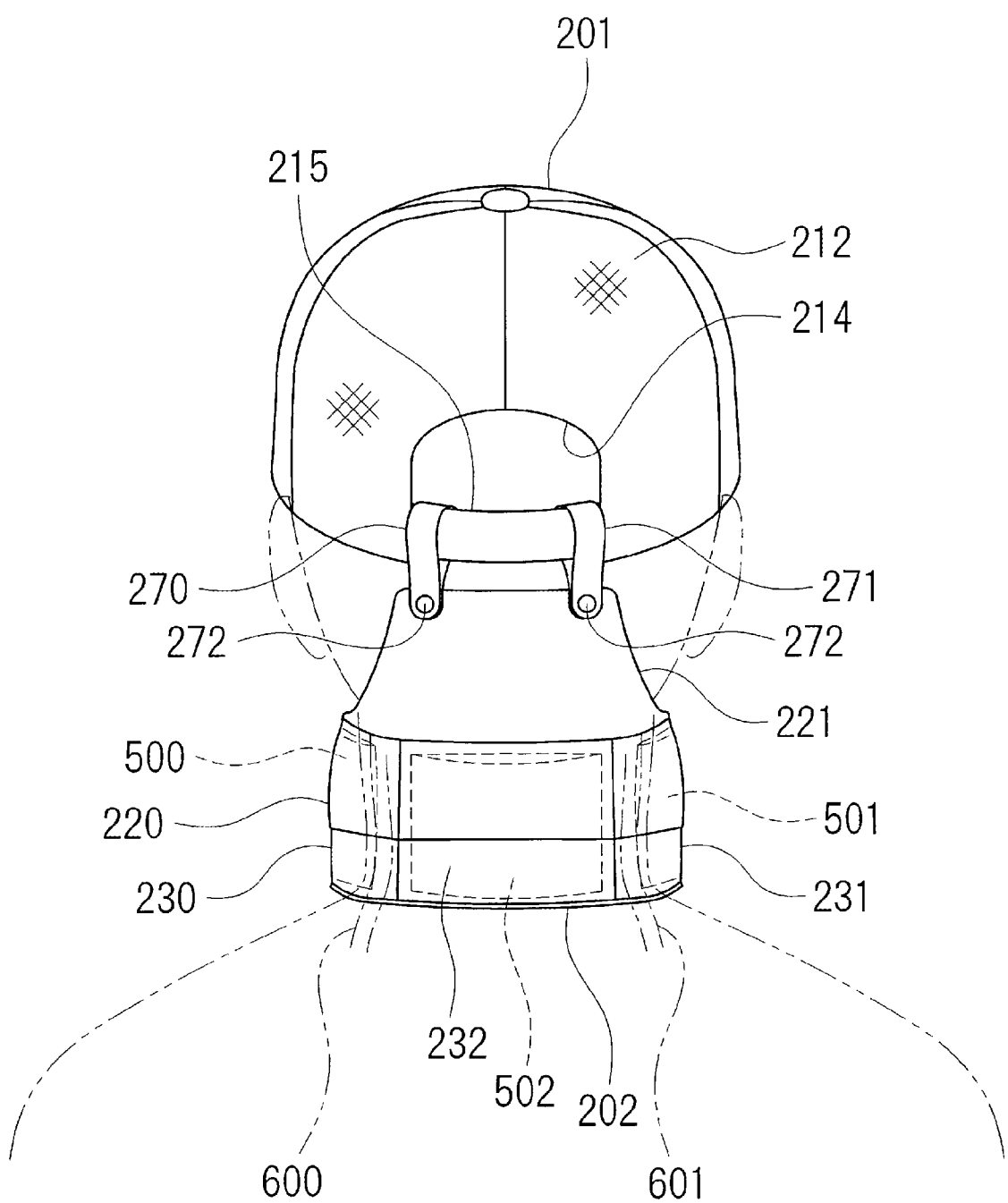
FIG. 69 is a diagram illustrating the worn state of the headgear, seen from the rear side.

FIG. 66 illustrates a state where the neck cover 202 is attached to the headgear main body 201 having the cap shape. The neck cover 202 is detachably attached to the headgear main body 201 by the first and second attachment bands 270 and 271. The first and second attachment bands 270 and 271 surround the adjustment band 215 from the front to the back. FIGS. 67(a) to 67(c) representatively illustrate a process in which the first attachment band 270 is attached to the adjustment band 215. First, as illustrated in FIG. 67(a), a user positions the first attachment band 270 on the back side of the adjustment band 215. After that, the user grips an upper end part of the first attachment band 270 and pulls the upper end part of the first attachment band 270 through the main body notch part 214 to the front side. The first attachment band 270 is passed over the adjustment band 215 to the front side. As illustrated in FIG. 67(b), the upper end part of the first attachment band 270 is folded downward on the upper side of the adjustment band 215. Subsequently, as illustrated in FIG. 67(c), the first attachment band 270 is folded in half, and the first dot button 272 engages with the second dot button 273. Engaging the first dot button 272 with the second dot button 273 makes it possible to maintain a folded state of the first attachment band 270. Thus, the neck cover 202 is suspended from the adjustment band 215 of the headgear main body 201 via the first and second attachment bands 270 and 271. It is noted that only one attachment band may be provided, and the number of attachment bands may be chosen freely. The first dot button 272 and the second dot buttons 273 may be provided as a plurality of dot buttons at each of an upper end part and a lower end part of one attachment band.

In addition, the attachment tool may be a dot button attached to the neck cover 202. When the dot button is attached to the headgear main body 201, the neck cover 202 may be attached to the dot button of the headgear main body 201. Furthermore, the attachment part may be, for example, an incision for a button formed in the neck cover 202. When a button is sewn to the headgear main body 201, the button on the headgear main body 201 may be fixed in the incision of the neck cover 202.

REFERENCE SIGNS LIST

1 Headgear main body
2 Neck cover
10 Major main body part
11 Brim part
12 Main body notch part
13 Adjustment band
14 Dot button
20 Dot button
21 Left end part
21a Upper end part
21b Left extension part
22 Right end part
22a Upper end part
22b Right extension part
23 Hook-and-loop fastener (coupling part)
24 Cover notch part
30 First pocket (first holding part)
30a Opening part
30b Front side edge part
31 Second pocket (second holding part)
31a Opening part
31b Front side edge part
32 Third pocket (third holding part)
32a Opening part
40 First piece
41 Second piece
41a Front piece
41b Back piece
42 Third piece
43 Sewn part
101 Headgear main body
102 Neck cover
110 Major main body part
111 Sweat stopper part
112 Bordering piece
120 Main neck part
121 Protruding part
121a Upper end part (connection part)
122 Straight part
123 Tapered part
124 First pocket (first holding part)
125 Second pocket (second holding part)
126 Third pocket (third holding part)
127 Hook-and-loop fastener (coupling part)
128 Upper piece
129 Lower piece
201 Headgear main body
202 Neck cover
210 Major main body part
210a Upper part
210b Lower part
211 Brim part
212 Air-permeable part
213 Air-impermeable part
214 Main body notch part
215 Adjustment band
220 Main neck part
221 Protruding part
221a Upper end part
221b Left end part
221c Right end part
222 Straight part
223 Tapered part
224 Hook-and-loop fastener
230 First pocket (first holding part)
231 Second pocket (second holding part)
232 Third pocket (third holding part)
233 Upper piece
234 Lower piece
235 Opening part
240 First clip (first attachment part)
241 Second clip (second attachment part)
242 Third clip (third attachment part)
243 Fourth clip (fourth attachment part)
250 First sandwiching part
251 Second sandwiching part
252 Fixed piece
253 Movable piece
254 Restraining piece
260 Ring
261 Attachment piece
270 First attachment band (first attachment part)
271 Second attachment band (second attachment part)
272 First dot button
273 Second dot button
500 First cooling member
501 Second cooling member
502 Third cooling member
600 Left carotid artery
601 Right carotid artery
610 Neck
611 Shoulder
700 Helmet

The invention claimed is:

1. A headgear comprising:
a headgear main body of a hemispherical inner cap, which is configured to be worn on a head, the headgear main body comprising a major main body part being a main portion of the headgear main body and made of a first fabric; and
a neck cover that is configured to cover a neck, the neck cover comprising a main neck part being a main portion of the neck cover and made of a second fabric thinner than the first fabric,
first and second holding parts that respectively hold first and second cooling members, wherein the first and second holding parts are provided in the neck cover,
wherein in a worn state, the first and second holding parts are respectively configured to be positioned laterally to left and right carotid arteries,
wherein a rear part of the headgear main body is connected to the neck cover, and
wherein a front part and left and right side parts of the headgear main body are spaced from the neck cover.

2. The headgear according to claim 1, wherein
the first holding part is a first pocket that stores the first cooling member, and
the second holding part is a second pocket that stores the second cooling member.

3. The headgear according to claim 2, further comprising a coupling part that detachably couples a left end part and a right end part of the neck cover.

4. The headgear according to claim 3, wherein
the neck cover includes a left extension part provided in a lower part of the left end part of the neck cover and extending more to a front side than an upper end part of the left end part of the neck cover, and a right extension part provided in a lower part of the right end part of the neck cover and extending more to the front side than an upper end part of the right end part of the neck cover,
the coupling part is configured to detachably couple the left extension part and the right extension part, and
a front side edge part of the first pocket is positioned near a region vertically below the upper end part of the left end part of the neck cover, and a front side edge part of the second pocket is positioned near a region vertically below the upper end part of the right end part of the neck cover.

5. The headgear according to claim 1, wherein
the neck cover includes a connection part connected to the rear part of the headgear main body, and
a length of the connection part in a left-right direction is shorter than a diameter of the headgear main body.

6. The headgear according to claim 1, wherein
the neck cover is formed separately from the headgear main body,
the neck cover includes a protruding part protruding upward,
first and second attachment parts that detachably attach the neck cover to the headgear main body are provided in an upper end part of the protruding part, and
the first attachment part is provided above the first holding part, and the second attachment part is provided above the second holding part.

7. A headgear comprising:
a headgear main body of a hemispherical inner cap which is configured to be worn on a head;
a neck cover that is configured to cover a neck;
first and second holding parts that respectively hold first and second cooling members, wherein the first and second holding parts are provided in the neck cover, wherein in a worn state, the first and second holding parts is configured to be respectively positioned laterally to left and right carotid arteries;
wherein the headgear main body includes a major main body part being a main portion of the headgear main body and made of a first fabric, and
wherein the neck cover includes a main neck part being a main portion of the neck cover and made of a second fabric having higher elasticity than the first fabric,
wherein a rear part of the headgear main body is connected to the neck cover, and
wherein a front part and left and right side parts of the headgear main body are spaced from the neck cover.

8. The headgear according to claim 7, wherein
the first holding part is a first pocket that stores the first cooling member, and
the second holding part is a second pocket that stores the second cooling member.

9. The headgear according to claim 8, further comprising a coupling part that detachably couples a left end part and a right end part of the neck cover.

10. The headgear according to claim 9, wherein
the neck cover includes a left extension part provided in a lower part of the left end part of the neck cover and extending more to a front side than an upper end part of the left end part of the neck cover, and a right extension part provided in a lower part of the right end part of the neck cover and extending more to the front side than an upper end part of the right end part of the neck cover,
the coupling part is configured to detachably couple the left extension part and the right extension part, and
a front side edge part of the first pocket is positioned near a region vertically below the upper end part of the left end part of the neck cover, and a front side edge part of the second pocket is positioned near a region vertically below the upper end part of the right end part of the neck cover.

11. The headgear according to claim 7, wherein
the neck cover includes a connection part connected to the rear part of the headgear main body, and
a length of the connection part in a left-right direction is shorter than a diameter of the headgear main body.

12. The headgear according to claim 7, wherein
the neck cover is formed separately from the headgear main body,
the neck cover includes a protruding part protruding upward,
first and second attachment parts that detachably attach the neck cover to the headgear main body are provided in an upper end part of the protruding part, and
the first attachment part is provided above the first holding part, and the second attachment part is provided above the second holding part.

13. A headgear comprising:
a headgear main body of a hemispherical inner cap which is configured to be worn on a head;
a neck cover that is configured to cover a neck;
first and second holding parts that respectively hold first and second cooling members, wherein the first and second holding parts are provided in the neck cover, and wherein in a worn state, the first and second holding parts can be respectively positioned laterally to left and right carotid arteries, wherein the headgear main body includes a major main body part being a main portion of the headgear main body and made of a first fabric, and wherein the neck cover includes a main neck part being a main portion of the neck cover and made of a second fabric, and wherein the first fabric has higher air permeability than the second fabric, wherein a rear part of the headgear main body is connected to the neck cover, and wherein a front part and left and right side parts of the headgear main body are spaced from the neck cover.

14. The headgear according to claim 13, wherein
the first holding part is a first pocket that stores the first cooling member, and
the second holding part is a second pocket that stores the second cooling member.

15. The headgear according to claim 14, further comprising a coupling part that detachably couples a left end part and a right end part of the neck cover.

16. The headgear according to claim 15, wherein
the neck cover includes a left extension part provided in a lower part of the left end part of the neck cover and extending more to a front side than an upper end part of the left end part of the neck cover, and a right extension part provided in a lower part of the right end part of the neck cover and extending more to the front side than an upper end part of the right end part of the neck cover,
the coupling part is configured to detachably couple the left extension part and the right extension part, and
a front side edge part of the first pocket is positioned near a region vertically below the upper end part of the left end part of the neck cover, and a front side edge part of the second pocket is positioned near a region vertically below the upper end part of the right end part of the neck cover.

17. The headgear according to claim 16, wherein
the neck cover includes a connection part connected to the rear part of the headgear main body, and
a length of the connection part in a left-right direction is shorter than a diameter of the headgear main body.

18. The headgear according to claim 13, wherein
the neck cover is formed separately from the headgear main body,
the neck cover includes a protruding part protruding upward,
first and second attachment parts that detachably attach the neck cover to the headgear main body are provided in an upper end part of the protruding part, and
the first attachment part is provided above the first holding part, and the second attachment part is provided above the second holding part.

* * * * *